United States Patent
Jennings et al.

(10) Patent No.: US 9,605,175 B2
(45) Date of Patent: Mar. 28, 2017

(54) POLYMER COATING COMPOSITIONS AND COATED PRODUCTS

(71) Applicant: ARISTE MEDICAL, LLC, Memphis, TN (US)

(72) Inventors: Lisa Jennings, Memphis, TN (US); Jonathan McCanless, Memphis, TN (US); Brian Best, Oakland, CA (US); Timothy Fabian, Memphis, TN (US); Michael Cole, Boulder, CO (US)

(73) Assignee: ARISTE MEDICAL, LLC, Memphis, TN (US)

( * ) Notice: Subject to any disclaimer, the term of this patent is extended or adjusted under 35 U.S.C. 154(b) by 0 days.

(21) Appl. No.: 14/439,650

(22) PCT Filed: Oct. 29, 2013

(86) PCT No.: PCT/US2013/067341
§ 371 (c)(1),
(2) Date: Apr. 29, 2015

(87) PCT Pub. No.: WO2014/070792
PCT Pub. Date: May 8, 2014

(65) Prior Publication Data
US 2015/0275026 A1    Oct. 1, 2015

Related U.S. Application Data

(60) Provisional application No. 61/719,934, filed on Oct. 29, 2012, provisional application No. 61/755,440, (Continued)

(51) Int. Cl.
*A61K 47/32* (2006.01)
*C08L 33/06* (2006.01)
(Continued)

(52) U.S. Cl.
CPC .......... *C09D 133/10* (2013.01); *A61K 31/436* (2013.01); *A61K 31/496* (2013.01); (Continued)

(58) Field of Classification Search
CPC .... C09D 133/10; A61K 31/496; A61K 31/65; A61K 45/06; A61K 47/32; A61K 31/436
(Continued)

(56) References Cited

U.S. PATENT DOCUMENTS 3,998,715 A    12/1976 Bohm et al.
4,016,306 A    4/1977 Miyagawa et al.
(Continued)

FOREIGN PATENT DOCUMENTS

| CN | 101198659 A | | 6/2008 |
|---|---|---|---|
| JP | 05170705 | * | 7/1993 |
| JP | H07101904 A | | 4/1995 |
| JP | 2007101904 A | | 4/2007 |
| WO | WO-9112779 A1 | | 9/1991 |
| WO | WO-2012012865 A1 | | 2/2012 |

OTHER PUBLICATIONS

International search report and written opinion dated Dec. 20, 2013 for PCT Application No. US2013/067341.

*Primary Examiner* — T. Victor Oh
(74) *Attorney, Agent, or Firm* — Wilson Sonsini Goodrich & Rosati

(57) ABSTRACT

Described herein are coating compositions for consumer and/or medical products. The coating compositions can be used to confer desirable properties to the consumer and/or medical products.

12 Claims, 16 Drawing Sheets

A

B

Related U.S. Application Data filed on Jan. 22, 2013, provisional application No. 61/791,188, filed on Mar. 15, 2013.

(51) Int. Cl.

| | | |
|---|---|---|
| *C09D 133/10* | (2006.01) | |
| *C09D 4/00* | (2006.01) | |
| *A61K 31/436* | (2006.01) | |
| *A61K 31/496* | (2006.01) | |
| *A61K 31/65* | (2006.01) | |
| *A61K 45/06* | (2006.01) | |
| *C08F 220/14* | (2006.01) | |
| *C08F 222/10* | (2006.01) | |

(52) U.S. Cl.
CPC .............. *A61K 31/65* (2013.01); *A61K 45/06* (2013.01); *A61K 47/32* (2013.01); *C09D 4/00* (2013.01); *C08F 220/14* (2013.01); *C08F 222/1006* (2013.01); *C08F 2222/102* (2013.01)

(58) Field of Classification Search
USPC .... 514/152, 254.11, 291, 772.4; 522/33, 64; 524/560
See application file for complete search history.

(56) References Cited

U.S. PATENT DOCUMENTS

| | | |
|---|---|---|
| 4,368,300 A | 1/1983 | Nakano et al. |
| 4,886,062 A | 12/1989 | Wiktor |
| 5,176,692 A | 1/1993 | Wilk et al. |
| 5,217,493 A | 6/1993 | Raad et al. |
| 5,290,217 A | 3/1994 | Campos |
| 5,320,886 A | 6/1994 | Bowen |
| 5,348,988 A | 9/1994 | Suh et al. |
| 5,356,432 A | 10/1994 | Rutkow et al. |
| 5,569,273 A | 10/1996 | Titone et al. |
| 5,624,704 A | 4/1997 | Darouiche et al. |
| 5,767,170 A | 6/1998 | Ibsen et al. |
| 5,824,082 A | 10/1998 | Brown |
| 5,902,283 A | 5/1999 | Darouiche et al. |
| 6,166,286 A | 12/2000 | Trabucco |
| 6,558,686 B1 | 5/2003 | Darouiche |
| 6,780,497 B1 | 8/2004 | Walter |
| 6,800,082 B2 | 10/2004 | Rousseau |
| 7,666,496 B2 | 2/2010 | Duran |
| 2006/0052471 A1 | 3/2006 | Ashman et al. |

\* cited by examiner

A   B

POLYMER COATING COMPOSITIONS AND COATED PRODUCTS

CROSS-REFERENCE

This application claims the benefit of U.S. Provisional Application No. 61/719,934, filed Oct. 29, 2012, U.S. Provisional Application No. 61/755,440, filed Jan. 22, 2013, and U.S. Provisional Application No. 61/791,188, filed Mar. 15, 2013, which applications are incorporated herein by reference.

BACKGROUND OF THE INVENTION

Biocompatible coatings for implantable medical devices are becoming increasingly important throughout the medical device industry. For example, lubricious coatings such as polyvinylpyrrolidone (PVP), polyurethane, polyester, vinyl resin, fluorocarbons, silicone, rubber and combinations thereof have been applied to medical devices such as stents. Many of these coated medical devices suffer from drawbacks. For example, the coatings may suffer from poor adhesion to medical device surfaces, poor lubricity, poor drug releasing properties, and/or poor biocompatibility. Thus, there is a need in the art for a medical device coating that confers improved biocompatibility to the device and/or confers desired drug elution kinetics.

Poor biocompatibility can be a major drawback in some medical devices. When medical devices have non-biocompatible surfaces, they can initiate a reaction by the human or animal body or its blood, fluids or other biologic membranes which may result in serious patient complications such as inflammation and/or rejection. Medical devices have, therefore, conventionally been made of relatively inert plastic or elastomeric materials. These materials, however, still have varying degrees of biocompatibility.

Infections associated with medical devices also represent a major health care problem. Hospital acquired infections (nosocomial infections) are the 11th leading cause of death in the US and cost over $2 billion annually. A significant percentage of these infections are related to microbe colonization of implanted medical implants such as Foley catheters (urinary tract infections), endotracheal and tracheostomy tubes (respiratory tract infections), vascular infusion catheters (bloodstream infections), and hernia patches. Common infectious agents that can infect medical implants include, e.g., catheters. Staphylococci (*S. aureus, S. epidermidis, S. pyogenes*), Enterococci (*E. coli*), Gram Negative Aerobic Bacilli, and *Pseudomonas aeruginosa* are common pathogens. Once a medical implant becomes colonized by bacteria, it must frequently be replaced resulting in increased morbidity for the patient and increased cost to the healthcare system. Often the infected device serves as a source for a disseminated infection, which can lead to significant morbidity or even death.

A ventral hernia is a bulge or a tear forming in the surrounding tissue of the abdominal muscles. Tens of thousands of ventral hernia repairs are performed in the United States each year. A common procedure for repairing a hernia may involve implanting a hernia patch, either over the hernial opening or inside the ventral wall opening. The hernia patches can irritate the intestines due to poor biocompatibility. Placement and fixation of the hernia patch (e.g., by sutures) often cause significant pain to the subject. Further, the patches have been reported to have a likelihood of harboring bacteria, thereby leading to infections, such as surgical site infections.

Handheld objects such as touchscreen phones, iPods, GPS devices, computers and tablets can demonstrate significant amounts of microorganisms, viruses or agents that can be easily transferred to the mouth, nose, ears, or wounded areas of users, leading to infection or inflammation or both. Recent studies have demonstrated "abnormally high numbers of coliforms, a bacteria indicating fecal contamination, with about 2,700-4,200 units of bacteria" on each phone tested. Given the recent increase in use of handheld technology, both in terms of penetration within populations and in the number of times accessed per hour, it is desirable to reduce the risk of infection or inflammation or both associated with the use of such devices.

SUMMARY OF THE INVENTION

The invention provides for a composition for preparing a polymer coating comprising a therapeutic agent, comprising an aromatic dimethacrylate component or salt thereof, a monomethacrylate component or salt thereof, a solvent, and the therapeutic agent.

The invention also provides for a composition for preparing a polymer coating comprising an odorant, comprising an aromatic dimethacrylate component or salt thereof, a monomethacrylate component or salt thereof, a solvent, and the odorant In some embodiments, the therapeutic agent is present in an amount of 0.01-1000 mg/ml by weight/volume of the composition. In some embodiments, the therapeutic agent is present in an amount of 0.1-100 mg/ml by weight/volume of the composition. In some embodiments, the therapeutic agent is present in an amount of 0.4-40 mg/ml by weight/volume of the composition. In some embodiments, the therapeutic agent is selected from the group consisting of antiplatelets, antithrombins, cytostatic agents, antiproliferative agents, vasodilators, alkylating agents, antimicrobials, antibiotics, antimitotics, anti-infective agents, antisecretory agents, anti-inflammatory agents, immunosuppressive agents, antimetabolite agents, growth factor antagonists, free radical scavengers, antioxidants, radiotherapeutic agents, anesthetic agents, radiopaque agents, radiolabeled agents, nucleotides, cells, proteins, glycoproteins, hormones, odor-emitting agents, anti-stenosis agents, isolates, enzymes, monoclonal antibodies, ribonucleases and any combinations thereof. In some embodiments, an invention composition comprises two or more therapeutic agents.

In some embodiments, an invention composition comprises an odorant.

In some embodiments, an invention composition further comprises a polymerization initiator. In some embodiments, the polymerization initiator comprises camphorquinone.

In some embodiments, the solvent is selected from the group consisting of water, acetone, methanol, ethanol, ethyl acetate, dichloromethane, dimethylformamide, methyl acetate, heptane(s), tetrachloroethane, tetrahydrofuran, toluene, trichloroethylene, xylene(s), and mixtures thereof. In some embodiments, upon formulation the solvent accounts for at least 80 wt % of the initial volume of the composition.

In some embodiments, the composition comprises 4-20% of the aromatic dimethacrylate component by wt/wt or wt/vol, 0.25-20% mono-methacrylate component by wt/wt or wt/vol, 60-96% solvent by wt/wt or wt/vol, and 0.05-5% polymerization initiator by wt/wt or wt/vol. In some embodiments, the composition comprises 8% of the aromatic dimethacrylate component by wt/wt or wt/vol, 0.25-1% mono-methacrylate component by wt/wt or wt/vol, 90-92% solvent by wt/wt or wt/vol, and 0.05-1% polymerization initiator by wt/wt or wt/vol. In some embodiments, the composition comprises 12% of the aromatic dimethacrylate component by wt/wt or wt/vol, 0.25-2% mono-methacrylate component by wt/wt or wt/vol, 80-88% solvent by wt/wt or wt/vol, and 0.05-1% polymerization initiator by wt/wt or wt/vol. In some embodiments, the composition comprises 7% of the aromatic dimethacrylate component by wt/wt or wt/vol, 0.25-2% mono-methacrylate component by wt/wt or wt/vol, 90-93% solvent by wt/wt or wt/vol, and 0.05-1% polymerization initiator by wt/wt or wt/vol.

The invention also provides a polymerized coating, comprising a copolymer of an aromatic dimethacrylate and a mono-methacrylate, and a therapeutic agent. The invention also provides a polymerized coating, comprising a copolymer of an aromatic dimethacrylate and a mono-methacrylate, and an odorant.

In any of the foregoing compositions and polymer coatings, the aromatic dimethacrylate component comprises a dimethacrylate or salt thereof selected from the group consisting of

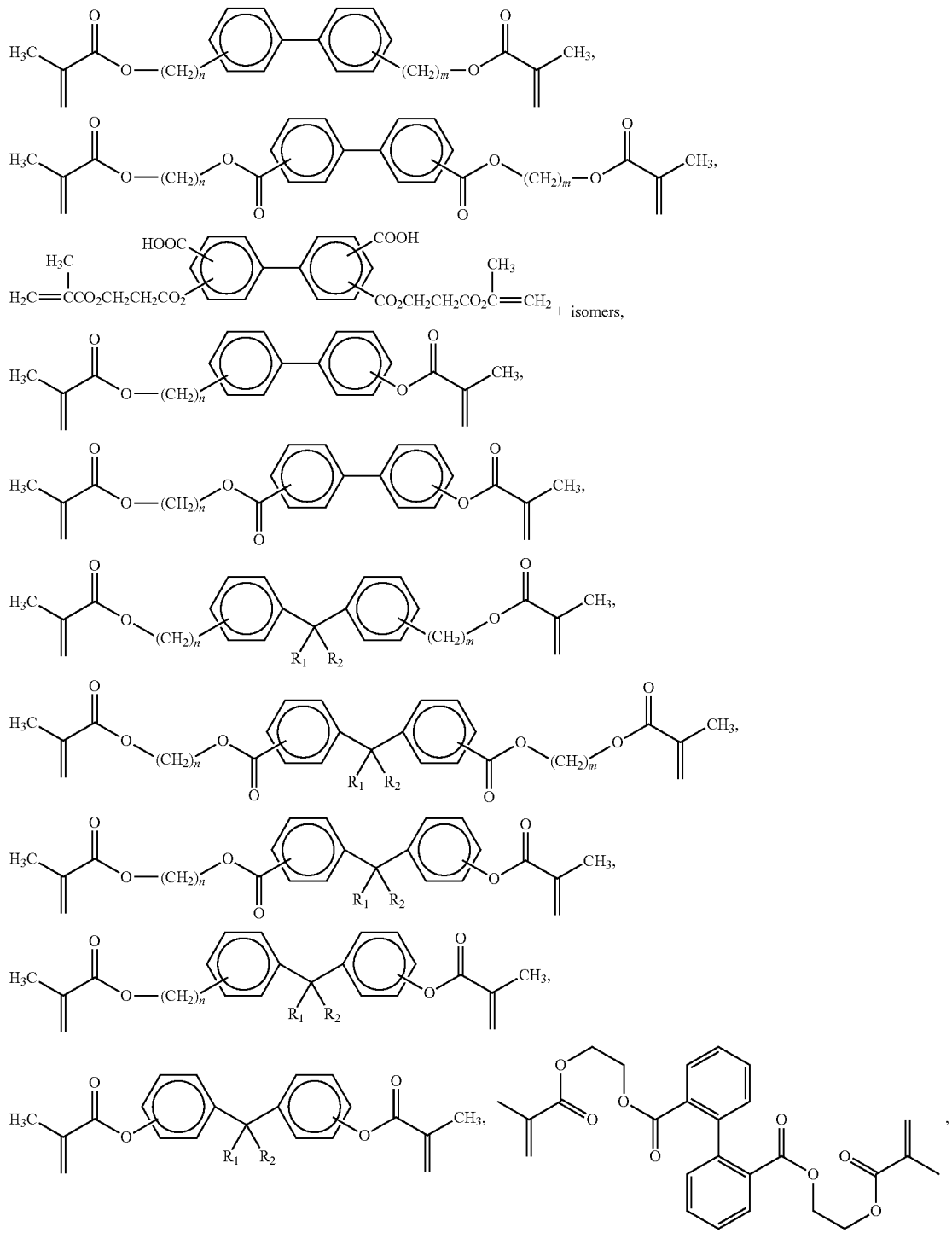

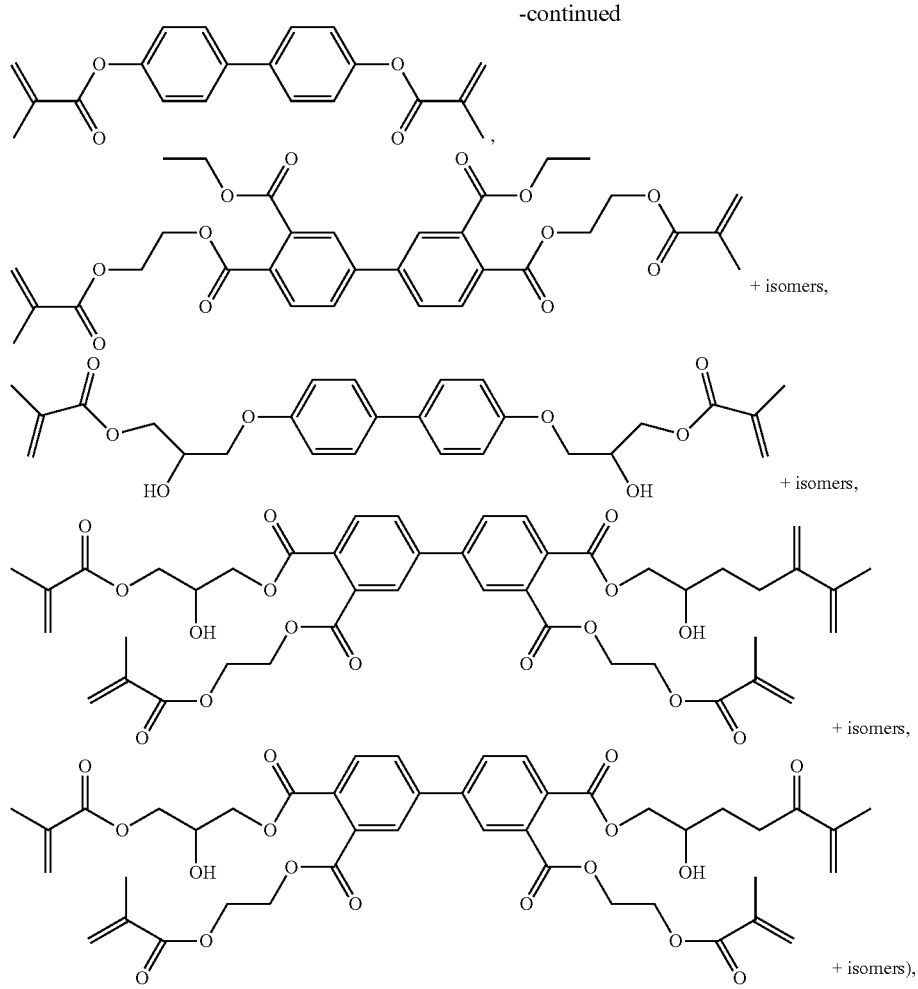

and combinations thereof, wherein each n is independently 2-10, each m is independently 2-10, and wherein each R1 and each R2 is independently selected from the group consisting of H, C1-C10 alkyl, aryl, and heteroaryl, wherein said C1-C10 alkyl, aryl, heteroaryl, when present, is optionally substituted with halo, aryl, heteroaryl, —NR21R22, OR23, SR24, —S(O)R25, —S(O)2R26, —PR27R28, —NR29(C=O)R30, —NR31S(=O)2R32, or —C(=O) NR33R34, or R1 and R2 in combination with the carbon to which they are attached form a C3-C8 cycloalkyl or C3-C8 heterocycloalkyl, each R21, R22, R23, R24, R25, R26, R27, R28, R29, R30, R31, R32, R33, and R34 is independently selected from the group consisting of H, C1-C6 alkyl, —C(=O)R40, aryl, and heteroaryl, R40 is C1-C6 alkyl.

In some embodiments, the dimethacrylate is selected from

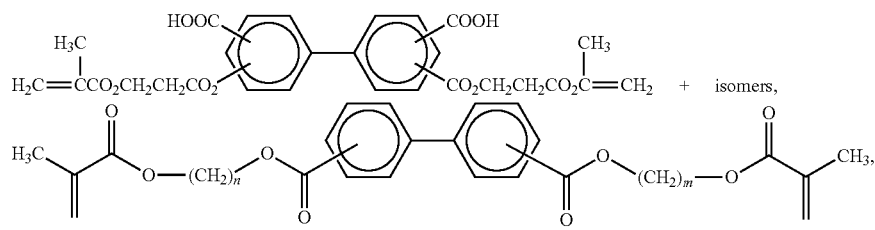

and salts thereof. In particular embodiments the dimethacrylate is selected from

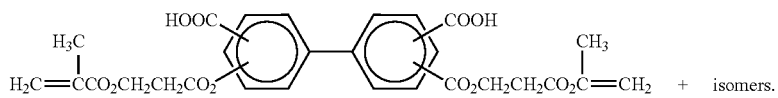

In some embodiments, the dimethacrylate is selected from

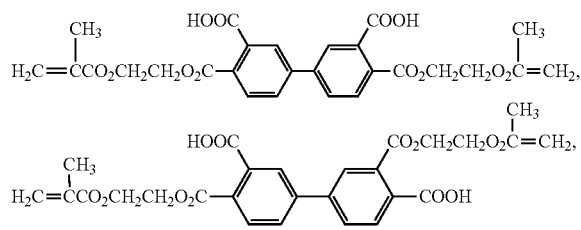

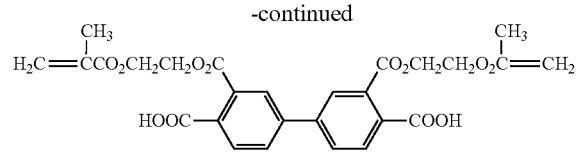

and salts thereof.

In particular embodiments, the dimethacrylate is

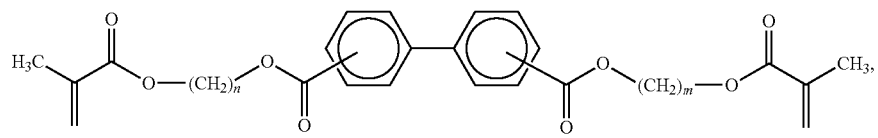

wherein n and m are each independently 2-10.

In some embodiments, dimethacrylate is

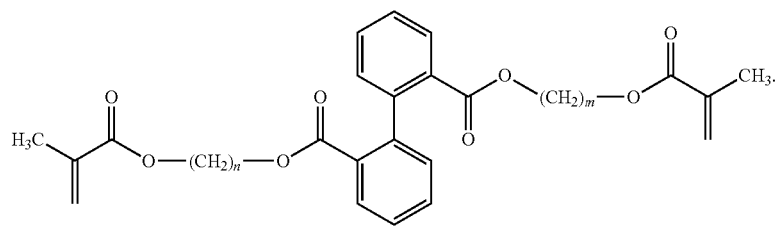

In some embodiments, n and m are each independently 2, 3, 4, 5, or 6. In particular embodiments, n is 2 and m is 2. E.g., the dimethacrylate is

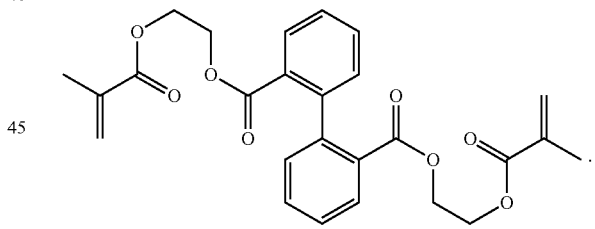

In some embodiments, the dimethacrylate is selected from:

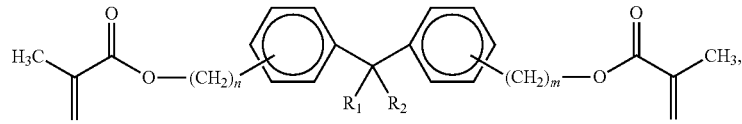

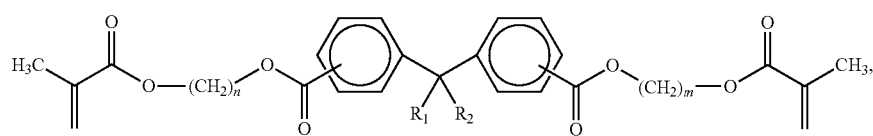

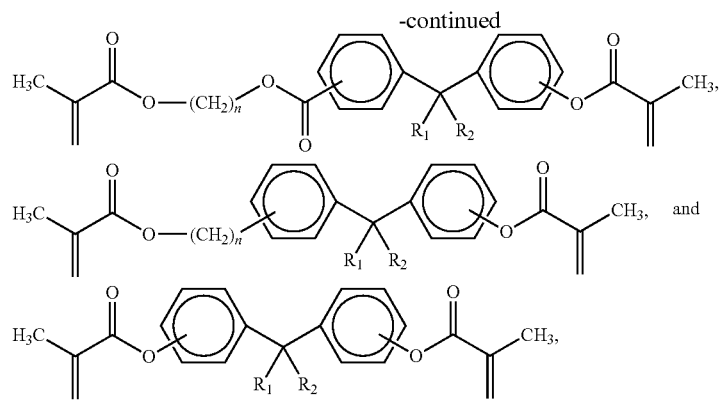

wherein each n is independently 2-10, each m is independently 2-10, and wherein each R1 and each R2 is independently selected from the group consisting of H, C1-C10 alkyl, aryl, and heteroaryl, wherein said C1-C10 alkyl, aryl, heteroaryl, when present, is optionally substituted with halo, aryl, heteroaryl, —NR21R22, OR23, SR24, —S(O)R25, —S(O)2R26, —PR27R28, —NR29(C=O)R30, —NR31S(=O)2R32, or —C(=O)NR33R34, or R1 and R2 in combination with the carbon to which they are attached form a C3-C8 cycloalkyl or C3-C8 heterocycloalkyl, each R21, R22, R23, R24, R25, R26, R27, R28, R29, R30, R31, R32, R33, and R34 is independently selected from the group consisting of H, C1-C6 alkyl, —C(=O)R40, aryl, and heteroaryl, R40 is C1-C6 alkyl. In some embodiments, each R1 and each R2 is independently selected from the group consisting of H, C1-C10 alkyl, aryl, and heteroaryl. In some embodiments, each R1 and each R2 is independently selected from the group consisting of H, C1-C10 alkyl. In some embodiments, n and m are each independently 2, 3, 4, 5, or 6. In particular embodiments, n is 2 and m is 2.

In some embodiments, the dimethacrylate is

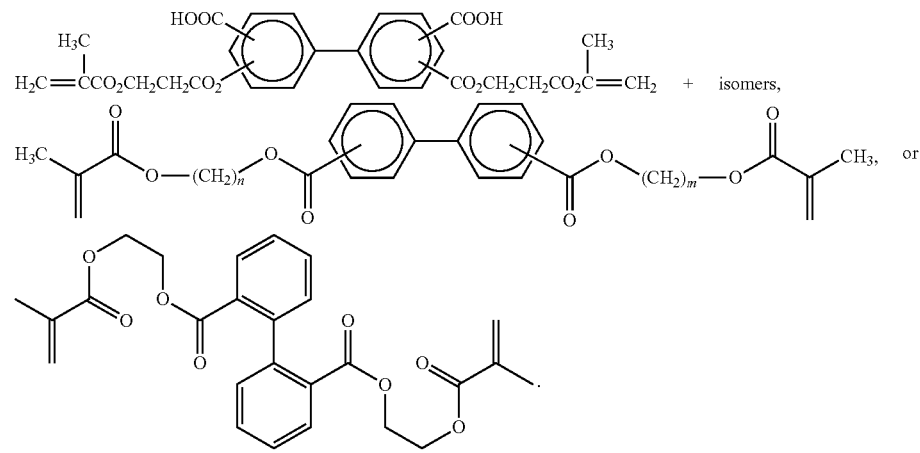

In some embodiments, the dimethacrylate is

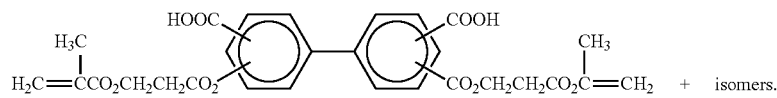

In some embodiments, the dimethacrylate is

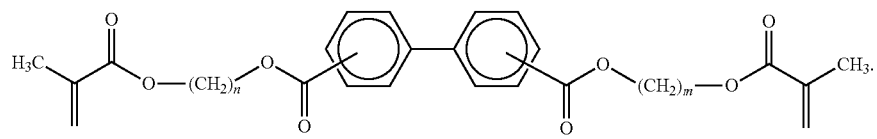

In some embodiments, the dimethacrylate is

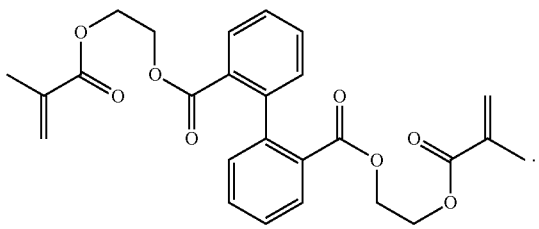 [SMILES: C=C(C)C(=O)OCCOC(=O)c1ccccc1-c1ccccc1C(=O)OCCOC(=O)C(=C)C]

In any of the foregoing compositions and polymerized coatings, the monomethacrylate can comprise a tertiary amine. In any of the foregoing compositions and polymer coatings, the monomethacrylate can be selected from the group consisting of methyl methacrylate, N-tolylglycine-glycidylmethacrylate (NTG-GMA), hydroxyethyl methacrylate (HEMA), and salts thereof. In some embodiments, the monomethacrylate is N-tolylglycine-glycidylmethacrylate (NTG-GMA), and salts thereof. In some embodiments, the monomethacrylate is methyl methacrylate.

In some embodiments, the aromatic dimethacyrlate and the monomethacrylate in the copolymer are present in a ratio of 100:1-1:1. In some embodiments, the aromatic dimethacyrlate and the monomethacrylate in the copolymer are present in a ratio of 50:1-2:1. In some embodiments, the aromatic dimethacyrlate and the monomethacrylate in the copolymer are present in a 20:1-5:1 ratio. In particular embodiments, the aromatic dimethacyrlate and the monomethacrylate in the copolymer are present in a 8:1 ratio. In particular embodiments, the aromatic dimethacyrlate and the monomethacrylate in the copolymer are present in a 12:1 ratio. In particular embodiments, the aromatic dimethacyrlate and the monomethacrylate in the copolymer are present in a 7:1 ratio. In particular embodiments, the aromatic dimethacyrlate and the monomethacrylate in the copolymer are present in a 14:1 ratio. In particular embodiments, the aromatic dimethacyrlate and the monomethacrylate in the copolymer are present in a 16:1 ratio. In particular embodiments, the aromatic dimethacyrlate and the monomethacrylate in the copolymer are present in a 1:1 ratio.

In any of the foregoing polymerized coatings, the therapeutic agent can be present in an amount of 0.01-1000 mg/g by wt/wt of the polymerized coating. In some embodiments, the therapeutic agent is present in an amount of 0.1-100 mg/ml by wt/wt of the polymerized coating. In some embodiments, the therapeutic agent is present in an amount of 0.4-40 mg/ml by wt/wt of the polymerized coating. In any of the foregoing polymerized coatings, the therapeutic agent can be selected from the group consisting of antiplatelets, antithrombins, cytostatic agents, antiproliferative agents, vasodilators, alkylating agents, antimicrobials, antibiotics, antimitotics, anti-infective agents, antisecretory agents, anti-inflammatory agents, immunosuppressive agents, antimetabolite agents, growth factor antagonists, free radical scavengers, antioxidants, radiotherapeutic agents, anesthetic agents, radiopaque agents, radiolabeled agents, nucleotides, cells, proteins, glycoproteins, hormones, odor-emitting agents, anti-stenosis agents, isolates, enzymes, monoclonal antibodies, ribonucleases and any combinations thereof. In some embodiments, the polymerized coating is configured to elute the therapeutic agent at a controlled rate when placed inside a subject. In some embodiments, the polymerized coating further comprises a polymerization initiator. In some embodiments, the polymerization initiator comprises camphorquinone.

The invention also provides a method of preparing a coated man-made product, comprising: combining a first solution comprising an aromatic dimethacrylate and a solvent with a second solution comprising a monomethacrylate and a solvent, wherein the combining results in a formulation for preparing a polymerized coating, applying the formulation to a surface of a man-made product, and polymerizing the formulation to create a layer of polymerized coating adhered to the surface of the man-made product, wherein a therapeutic agent or odorant is added to either the first solution, the second solution, or to the formulation prior to said applying.

The invention also provides a method of preparing a coated man-made product, comprising: admixing into a solvent an aromatic dimethacrylate and a monomethacrylate, wherein the admixing results in a formulation for preparing a polymerized coating, applying the formulation to a surface of a man-made product, and polymerizing the formulation to create a layer of polymerized coating adhered to the surface of the man-made product, wherein a therapeutic agent or odorant is added to the formulation before or after the polymerizing. In practicing any of the foregoing methods, the aromatic dimethacrylate can be any of the foregoing aromatic dimethacrylates herein. In practicing any of the foregoing methods, the monomethacrylate can be any of the foregoing monomethacrylates herein.

In some embodiments, the first solution, second solution, and/or formulation further comprises a solvent. In some embodiments, the solvent is selected from the group consisting of water, acetone, methanol, ethanol, ethyl acetate, dichloromethane, dimethylformamide, methyl acetate, heptane(s), tetrachloroethane, tetrahydrofuran, toluene, trichloroethylene, xylene(s), and mixtures thereof. In some embodiments, the first solution, second solution, and/or formulation further comprises a polymerization initiator. In some embodiments, the polymerization initiator is a photoinitiator. In some embodiments, the photoinitiator is camphorquinone, 2-hydroxy-1-[4-(2-hydroxyethoxyl)phenyl]-2-methyl-1-propanone (Igracure 2959), phenylbis(2,4,6-trimethylbenzoyl)phosphine oxide (PTPO), or diphenyl(2,4,6-trimethylbenzoyl)phosphine oxide. In some embodiments, the photoinitiator is 2-hydroxy-1-[4-(2-hydroxyethoxyl)phenyl]-2-methyl-1-propanone. In some embodiments, the photoinitiator is camphorquinone. In some embodiments, the method further comprises adding one or more solvents to the formulation prior to step (b).

In some embodiments, the method further comprises contacting the surface with a solvent prior to applying the formulation to the surface of the man-made product. In some embodiments, the solvent is acetone.

In some embodiments, the polymerizing comprises curing the formulation on the surface of the man-made product. In some embodiments, the curing comprises subjecting the product to an artificial light source. In some embodiments, the polymerized coating is evenly coated on the surface. In some embodiments, the surface of the man-made product comprises a porous structure, and the polymerized coating penetrates the porous structure without occluding pores of the porous structure. In some embodiments, the method further comprises roughening the surface prior to applying the formulation to the surface of the man-made coating. In some embodiments, the method comprises evaporating solvent from the formulation prior to the polymerizing.

The invention also provides a system for coating a man-made product, comprising: a first solution comprising an aromatic dimethacrylate and a solvent, a second solution comprising a monomethacrylate and a solvent, the man-made product, and an apparatus for curing a formulation onto a surface of a man-made product. In some embodiments, the first solution, second solution, none, or both comprise a therapeutic agent and/or an odorant. The invention also provides a system for coating a man-made product, comprising: (a) a formulation comprising an aromatic dimethacrylate, a monomethacrylate, a therapeutic agent or odorant, and a solvent, (b) the man-made product, and (c) an apparatus for curing a formulation onto a surface of a man-made product. In practicing the invention, the aromatic dimethacrylate of the foregoing systems can be any of the aromatic dimethacrylates herein. In practicing the invention, the monomethacrylate of the foregoing systems can be any of the foregoing monomethacrylates herein. In some embodiments, the system comprises a therapeutic agent. In some embodiments, the therapeutic agent is dissolved in the first solution. In some embodiments, the therapeutic agent is dissolved in the second solution. In some embodiments, the therapeutic agent is dissolved in the formulation. In some embodiments, the therapeutic agent is not dissolved in either the first solution, second solution, or formulation prior to polymerization of the formulation. In some embodiments, the therapeutic agent is selected from the group consisting of antiplatelets, antithrombins, cytostatic agents, antiproliferative agents, vasodilators, alkylating agents, antimicrobials, antibiotics, antimitotics, anti-infective agents, antisecretory agents, anti-inflammatory agents, immunosuppressive agents, antimetabolite agents, growth factor antagonists, free radical scavengers, antioxidants, radiotherapeutic agents, anesthetic agents, radiopaque agents, radiolabeled agents, nucleotides, cells, proteins, glycoproteins, hormones, odor-emitting agents, anti-stenosis agents, isolates, enzymes, monoclonal antibodies, ribonucleases and any combinations thereof. In some embodiments, the system further comprises an additional therapeutic agent. In some embodiments, the system comprises an odorant. In some embodiments, the odorant dissolved in the first solution. In some embodiments, the odorant is dissolved in the second solution. In some embodiments, the odorant is dissolved in the formulation. In some embodiments, the odorant is not dissolved in either the first solution, second solution, or formulation prior to polymerization of the formulation.

In some embodiments, the system further comprises a polymerization initiator. In some embodiments, the polymerization initiator is dissolved in the first solution. In some embodiments, the polymerization initiator is dissolved in the second solution. In some embodiments, the polymerization initiator is dissolved in the second solution. In some embodiments, the polymerization initiator is a photoinitiator. In some embodiments, the photoinitiator is camphorquinone, 2-hydroxy-1-[4-(2-hydroxyethoxy)phenyl]-2-methyl-1-propanone (Igracure 2959), phenylbis(2,4,6-trimethylbenzoyl)phosphine oxide (PTPO), or diphenyl(2,4,6-trimethyl-benzoyl)phosphine oxide. In some embodiments, the photoinitiator is 2-hydroxy-1-[4-(2-hydroxyethoxy)phenyl]-2-methyl-1-propanone. In some embodiments, the photoinitiator is camphorquinone.

In some embodiments, the apparatus comprises a degassing chamber. In some embodiments, the degassing chamber is a nitrogen degassing chamber. In some embodiments, the apparatus comprises a light source. In some embodiments, the light source is a UV light source. In some embodiments, the light source comprises an LED light. In some embodiments, the light source is configured to emit a light comprising wavelengths between 280-400 nm.

The invention also provides a compound of Formula (II):

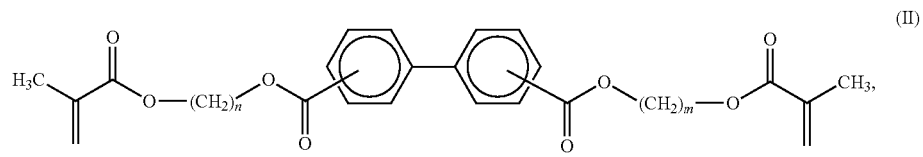

wherein each n is independently 1-10, and wherein each m is independently 1-10, and wherein the compound is in liquid form at 25° C.

In some embodiments, the compound is

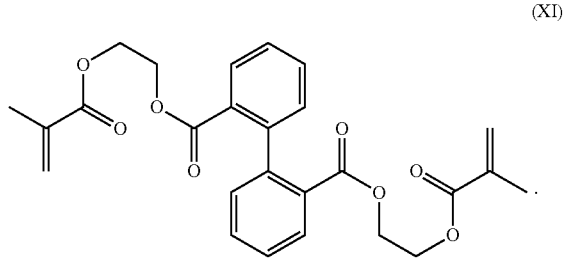 [SMILES: C=C(C)C(=O)OCCOC(=O)c1ccccc1-c1ccccc1C(=O)OCCOC(=O)C(=C)C]

The invention also provides a composition for the preparation of a polymer coating, comprising upon formulation, the compound of Formula II and a solvent. In some embodiments, the solvent is selected from the group consisting of water, acetone, methanol, ethanol, ethyl acetate, dichloromethane, dimethylformamide, methyl acetate, heptane(s), tetrachloroethane, tetrahydrofuran, toluene, trichloroethylene, xylene(s), and mixtures thereof. In some embodiments, the solvent accounts for at least 50% wt/wt of the composition upon formulation. In some embodiments, the solvent accounts for at least 80% wt/wt of the composition upon formulation. In some embodiments, the solvent accounts for at least 90% wt/wt of the composition upon formulation.

In some embodiments, the compound of Formula II accounts for 5-50% wt/wt of the composition upon formulation. In some embodiments, the compound of Formula II accounts for 5-30% wt/wt of the composition upon formulation. In some embodiments, the compound of Formula II accounts for 20% wt/wt of the composition upon formulation. In some embodiments, the compound of Formula II accounts for 10% wt/wt of the composition upon formulation. In some embodiments, the compound of Formula II accounts for 5% wt/wt of the composition upon formulation.

In some embodiments, the composition further comprises an additional methacrylate. In some embodiments, the additional methacrylate is a methyl methacrylate. In some embodiments, the methyl methacrylate is In some embodiments, the compound and the additional methacrylate are present in a ratio that is between 1:10-10:1. In some embodiments, the compound and the additional methacrylate are present in a ratio that is between 1:5-5:1. In some embodiments, the compound and the additional methacrylate are present in a ratio that is between 1:2-2:1. In some embodiments, the compound and the additional methacrylate are present in a 1:1 ratio. In some embodiments, the compound and the additional methacrylate together account for 10% of the composition by weight upon formulation. In some embodiments, the compound and the additional methacrylate together account for 20% of the composition by weight upon formulation.

In some embodiments, the composition further comprises a polymerization initiator. In some embodiments, the polymerization initiator is 2-hydroxy-1-[4-(2-hydroxyethoxyl) phenyl]-2-methyl-1-propanone, phenylbis(2,4,6-trimethylbenzoyl)phosphine oxide, or diphenyl(2,4,6-trimethylbenzoyl)phosphine oxide. In some embodiments, the polymerization initiator accounts for 0.1% wt/wt of the composition upon formulation. In some embodiments, the polymerization initiator accounts for 0.5% wt/wt of the composition upon formulation. In some embodiments, the polymerization initiator accounts for 1% wt/wt of the composition upon formulation. In some embodiments, the composition comprises upon formulation, by weight: 0.1%-50% of the compound, 50-99.9% of the solvent, and 0.001-10% of the polymerization initiator. In some embodiments, the composition comprises upon formulation, by weight: 1%-20% of the compound, 75%-99.9% of the solvent, and 0.01%-5% of the polymerization initiator. In some embodiments, the composition comprises upon formulation, by weight: 5%-15% of the compound, 80%-95% of the solvent, and 0.05%-1% of the polymerization initiator. In some embodiments, the composition comprises upon formulation, by weight: 9%-11% of the compound, 88%-92% of the solvent, and 0.08%-2% of the polymerization initiator. In some embodiments, the composition comprises upon formulation, by weight: 10% of the compound, 89-90% of the solvent, and 0.1-1% of the polymerization initiator. In some embodiments, the composition comprises upon formulation, by weight: 5% of the compound, 5% of the additional methacrylate, 89% of the solvent, and 1% of the polymerization initiator. In some embodiments, the solvent is acetone or dichloromethane. In some embodiments, the solvent is acetone. In some embodiments, the polymerization initiator is 2-hydroxy-1-[4-(2-hydroxyethoxyl)phenyl]-2-methyl-1-propanone, phenylbis(2,4,6-trimethylbenzoyl) phosphine oxide, or diphenyl(2,4,6-trimethylbenzoyl) phosphine oxide. In some embodiments, the composition further comprises a therapeutic agent. In some embodiments, the therapeutic agent is selected from the group consisting of antiplatelets, antithrombins, cytostatic agents, antiproliferative agents, vasodilators, alkylating agents, antimicrobials, antibiotics, antimitotics, anti-infective agents, antisecretory agents, anti-inflammatory agents, immunosuppressive agents, antimetabolite agents, growth factor antago-
nists, free radical scavengers, antioxidants, radiotherapeutic agents, anesthetic agents, radiopaque agents, radiolabeled agents, nucleotides, cells, proteins, glycoproteins, hormones, odor-emitting agents, anti-stenosis agents, isolates, enzymes, monoclonal antibodies, ribonucleases and any combinations thereof. In some embodiments, the composition comprises two or more therapeutic agents. In some embodiments, the composition comprises an odorant. In some embodiments, the composition comprises an odorant does not comprise a therapeutic agent. In some embodiments, the compound is

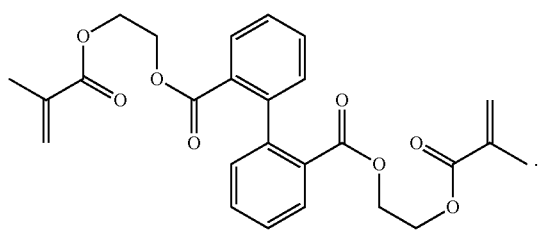 [SMILES: C=C(C)C(=O)OCCOC(=O)c1ccccc1-c1ccccc1C(=O)OCCOC(=O)C(=C)C]

The invention also provides a polymerized coating, comprising a polymer of an aromatic dimethacrylate of Formula (II):

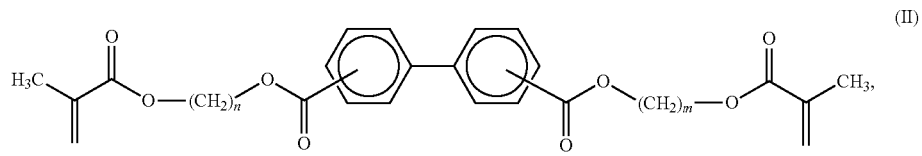

wherein each n is independently 1-10, and wherein each m is independently 1-10.

In some embodiments, the aromatic dimethacrylate is

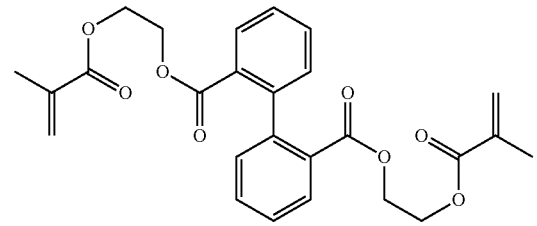 [SMILES: C=C(C)C(=O)OCCOC(=O)c1ccccc1-c1ccccc1C(=O)OCCOC(=O)C(=C)C]

In some embodiments, the polymerized coating further comprises a therapeutic agent. In some embodiments, the therapeutic agent is selected from the group consisting of antiplatelets, antithrombins, cytostatic agents, antiproliferative agents, vasodilators, alkylating agents, antimicrobials, antibiotics, antimitotics, anti-infective agents, antisecretory agents, anti-inflammatory agents, immunosuppressive agents, antimetabolite agents, growth factor antagonists, free radical scavengers, antioxidants, radiotherapeutic agents, anesthetic agents, radiopaque agents, radiolabeled agents, nucleotides, cells, proteins, glycoproteins, hormones, odor-emitting agents, anti-stenosis agents, isolates, enzymes, monoclonal antibodies, ribonucleases and any combinations thereof. In some embodiments, the polymerized coating comprises two or more therapeutic agents. In some embodiments, the polymerized coating comprises an odorant. In some embodiments, the polymerized coating comprising an odorant does not comprise a therapeutic agent.

In some embodiments, the polymer further comprises an additional methacrylate. In some embodiments, the additional methacrylate is a methyl methacrylate. In some embodiments, the methyl methacrylate is of the following structure:

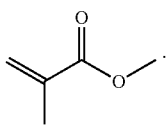

In some embodiments, the compound and the additional methacrylate are present in a ratio that is between 1:10-10:1. In some embodiments, the compound and the additional methacrylate are present in a ratio that is between 1:5-5:1. In some embodiments, the compound and the additional methacrylate are present in a ratio that is between 1:2-2:1. In particular embodiments, the compound and the additional methacrylate are present in a 1:1 ratio.

The invention also provides a method of preparing a coated man-made product, comprising: (a) dissolving an aromatic dimethacrylate into a solvent to create a formulation for preparing a polymerized coating; (b) applying the formulation to a surface of a man-made product, and (c) polymerizing the formulation to create the polymerized coating adhered to the surface of the man-made product. In such a method, the aromatic dimethacrylate is a compound of Formula II, described herein. In some embodiments, step (a) comprises dissolving the aromatic dimethacrylate and a therapeutic agent into the solvent. In some embodiments, the therapeutic agent is selected from the group consisting of antiplatelets, antithrombins, cytostatic agents, antiproliferative agents, vasodilators, alkylating agents, antimicrobials, antibiotics, antimitotics, anti-infective agents, antisecretory agents, anti-inflammatory agents, immunosuppressive agents, antimetabolite agents, growth factor antagonists, free radical scavengers, antioxidants, radiotherapeutic agents, anesthetic agents, radiopaque agents, radiolabeled agents, nucleotides, cells, proteins, glycoproteins, hormones, odor-emitting agents, anti-stenosis agents, isolates, enzymes, monoclonal antibodies, ribonucleases and any combinations thereof. In some embodiments, step (a) comprises dissolving the compound and two or more therapeutic agents into the solvent. In some embodiments, step (a) comprises dissolving the aromatic dimethacrylate and an odorant into the solvent. In some embodiments, an odorant nor therapeutic agent is dissolved into the solvent.

In some embodiments, the method further comprises adding a polymerization initiator to the formulation. In some embodiments, the polymerization initiator is 2-hydroxy-1-[4-(2-hydroxyethoxyl)phenyl]-2-methyl-1-propanone, phenylbis(2,4,6-trimethylbenzoyl)phosphine oxide, or diphenyl (2,4,6-trimethylbenzoyl)phosphine oxide. In some embodiments, the method comprises adding 0.1% wt/vol of the polymerization initiator to the formulation.

In some embodiments, the solvent is selected from the group consisting of water, acetone, methanol, ethanol, ethyl acetate, dichloromethane, dimethylformamide, methyl acetate, heptane(s), tetrachloroethane, tetrahydrofuran, toluene, trichloroethylene, xylene(s), and mixtures thereof. In some embodiments, the solvent accounts for at least 50% wt/wt of the formulation. In some embodiments, the solvent accounts for at least 80% wt/wt of the formulation.

In some embodiments, the formulation comprises, by weight: 0.1%-50% of the compound, 50-99.9% of the solvent, and 0.001-10% of the polymerization initiator. In some embodiments, the formulation comprises, by weight: 1%-20% of the compound, 75%-99.9% of the solvent, and 0.01%-5% of the polymerization initiator. In some embodiments, the formulation comprises, by weight: 5%-15% of the compound, 80%-95% of the solvent, and 0.05%-1% of the polymerization initiator. In some embodiments, the formulation comprises, by weight: 9%-11% of the compound, 88%-92% of the solvent, and 0.08%-0.2% of the polymerization initiator. In some embodiments, the formulation comprises, by weight: 10% of the compound, 89.9% of the solvent, and 0.1% of the polymerization initiator. In some embodiments, the compound is

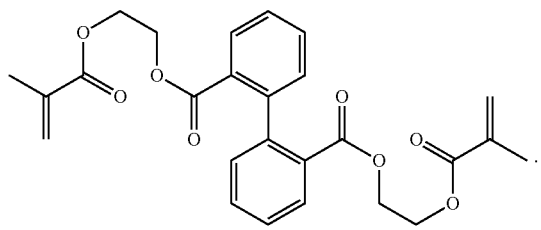 [SMILES: C=C(C)C(=O)OCCOC(=O)c1ccccc1-c1ccccc1C(=O)OCCOC(=O)C(=C)C]

In some embodiments, the method further comprises contacting the surface with a solvent prior to step (b). In some embodiments, the solvent is acetone. In some embodiments, the polymerizing comprises curing the formulation on the surface of the man-made product. In some embodiments, the curing comprises exposing the man-made product to an artificial light. In some embodiments, the artificial light emits wavelengths of 280-400 nm.

The invention also provides a system for coating a man-made product, comprising: a composition described herein, the man-made product, and an apparatus for curing the formulation onto a surface of a man-made product. In some embodiments, the apparatus comprises a degassing chamber. In some embodiments, the degassing chamber is a nitrogen degassing chamber. In some embodiments, the apparatus comprises a light source. In some embodiments, the light source is a UV light source. In some embodiments, the light source comprises light of wavelengths between 280-400 nm.

The invention also provides a man-made product comprising a surface, wherein at least a portion of the surface of the man-made product is coated with a layer of polymerized coating. In practicing the invention, the polymerized coating can be any polymerized coating described herein. In some embodiments, the surface comprises PTFE, ePTFE, compressed PTFE, or polypropylene. In some embodiments, the surface comprises ePTFE. In some embodiments, the polymerized coating comprises a copolymer of an aromatic dimethacrylate and a mono-methacrylate, and a therapeutic agent or odorant. Such polymerized coatings are described herein. In some embodiments, the polymerized coating comprises a polymer of a compound of Formula II, described herein. In some embodiments, the polymerized coating comprises a therapeutic agent. In some embodiments, the coating elutes a therapeutic agent upon contact with the subject. In some embodiments, the coating elutes the therapeutic agent for at least 30 days. In some embodiments, the coating elutes the therapeutic agent at a controlled rate. In some embodiments, the controlled rate is characterized by first order kinetics. In some embodiments, the polymerized coating reduces microbial colonization on the surface as compared to a corresponding surface which is uncoated. In some embodiments, the polymerized coating reduces microbial colonization for at least 30 days. In some embodiments, the product comprises two or more layers of the coating. In some embodiments, a layer has a thickness of 0.02-75 microns. In some embodiments, the layer has a thickness of 0.02-10 microns. In some embodiments, the layer has a thickness of 0.02-1 microns.

In some embodiments, the man-made product is not a dental product, and the polymerized coating comprises a copolymer of an aromatic dimethacrylate and a monomethacrylate, and a therapeutic agent or odorant.

In some embodiments, the man-made product is a medical device. In some embodiments, the medical device is configured for implantation into a live subject. In some embodiments, the live subject is a human. In some embodiments, the live subject is a rodent. In some embodiments, the rodent is a mouse.

In some embodiments, the product comprising a soft tissue mesh. In some embodiments, the soft tissue mesh comprises a flexible material. In some embodiments, the soft tissue mesh comprises pores. In some embodiments, the pores comprise an average diameter of 3-22 µm. In some embodiments, the coating does not occlude the pores. In some embodiments, the soft tissue mesh comprises filaments. In some embodiments, the filaments comprise a synthetic material. In some embodiments, the synthetic material is selected from the group consisting of PTFE, ePTFE, compressed PTFE, and polypropylene. In some embodiments, the synthetic material is ePTFE. In some embodiments, the synthetic material is polypropylene.

In some embodiments, the product comprises a first surface and a second surface. In some embodiments, the first surface and second surface are on opposite sides of the man-made product. In some embodiments, the first surface is a textured surface and the second surface is a smooth surface. In some embodiments, the textured surface is configured to enhance integration of a tissue from a subject. In some embodiments, the textured surface comprises a polymeric structure comprising expanded PTFE (ePTFE). In some embodiments, the polymeric structure comprises nodes, fibrils, pores and/or ablated structures. In some embodiments, the therapeutic agent is selected from the group consisting of antiplatelets, antithrombins, cytostatic agents, antiproliferative agents, vasodilators, alkylating agents, antimicrobials, antibiotics, antimitotics, anti-infective agents, antisecretory agents, anti-inflammatory agents, immunosuppressive agents, antimetabolite agents, growth factor antagonists, free radical scavengers, antioxidants, radiotherapeutic agents, anesthetic agents, radiopaque agents, radiolabeled agents, nucleotides, cells, proteins, glycoproteins, hormones, odor-emitting agents, anti-stenosis agents, isolates, enzymes, monoclonal antibodies, ribonucleases and any combinations thereof. In some embodiments, the smooth surface is configured to minimize integration or adhesion of a tissue from a subject. In some embodiments, the smooth surface is coated with a coating that comprises a therapeutic agent. In some embodiments, the therapeutic agent is selected from the group consisting of antiplatelets, antithrombins, cytostatic agents, antiproliferative agents, vasodilators, alkylating agents, antimicrobials, antibiotics, antimitotics, anti-infective agents, antisecretory agents, anti-inflammatory agents, immunosuppressive agents, antimetabolite agents, growth factor antagonists, free radical scavengers, antioxidants, radiotherapeutic agents, anesthetic agents, radiopaque agents, radiolabeled agents, nucleotides, cells, proteins, glycoproteins, hormones, odor-emitting agents, anti-stenosis agents, isolates, enzymes, monoclonal antibodies, ribonucleases and any combinations thereof In some embodiments, the soft tissue mesh is a hernia patch. In some embodiments, the hernia patch is a ventral hernia patch. In some embodiments, the ventral hernia patch elutes an antimicrobial agent. In some embodiments, the hernia patch is an inguenal hernia patch. In some embodiments, the inguenal hernia patch elutes an analgesic agent.

In some embodiments, the medical product is a catheter. In some embodiments, the catheter is a dialysis catheter, a venous catheter, or a urinary catheter. In some embodiments, the dialysis catheter is a tunneled dialysis catheter. In some embodiments, the venous catheter is a central venous catheter. In some embodiments, the catheter reduces occurrence of thrombosis upon implantation into a subject population. In some embodiments, the catheter is a urinary catheter. In some embodiments, the urinary catheter reduces occurrence of infection upon implantation into a subject population.

In some embodiments, the medical product is a graft. In some embodiments, the medical product is an Implantable Cardioverter Defibrillator. In some embodiments, the medical product is a pacemaker. In some embodiments, the medical product is an artificial joint replacement. In some embodiments, the artificial joint replacement is an artificial hip replacement. In some embodiments, the artificial joint replacement is an artificial knee replacement. In some embodiments, the medical product is a spinal fusion or bone fracture hardware device. In some embodiments, the spinal fusion or bone fracture hardware device is a spine screw, rod, pin, plate, or artificial disc. In some embodiments, the medical product is an Intrauterine device (IUD). In some embodiments, the medical product is a stent. In some embodiments, the stent elutes an anti-thrombotic agent. In some embodiments, the medical product is an ear tube. In some embodiments, the medical product is a wound dressing In some embodiments, the medical product is a scaffold. In some embodiments, the medical product is an angioplasty balloon. In some embodiments, the medical product is an implantable pump configured for chronic drug delivery. In some embodiments, the implantable pump is an osmotic minipump. In some embodiments, the man-made product is a medical device accessory. In some embodiments, the medical device accessory is configured for removable attachment to a medical device. In some embodiments, the medical device accessory is a catheter accessory. In some embodiments, the catheter accessory is a ring. In some embodiments, the ring is configured for removable attachment to a catheter entry point. In some embodiments, the ring elutes a therapeutic agent. In some embodiments, the catheter accessory is a plug configured for sealing a catheter port when the catheter is not in use. In some embodiments, the plug elutes a therapeutic agent. In some embodiments, the medical device accessory is a tube.

In some embodiments, the man-made product is an electronic device. In some embodiments, the electronic device is a hand-held electronic device. In some embodiments, the electronic device is a phone. In some embodiments, the electronic device is an electronic tablet. In some embodiments, the electronic device is a computer. In some embodiments, the electronic device is a laptop. In some embodiments, the man-made product is an electronic device accessory. In some embodiments, the electronic device accessory is a cover for the electronic device.

The invention also provides a method of reducing microorganism growth on a product, comprising applying a composition described herein to the product. In some embodiments, microorganism growth is reduced. In some embodiments, microorganism growth is reduced by at least 50%. In some embodiments, the applying reduces microorganism growth for a period of time. In some embodiments, the period of time is at least 7 days. In some embodiments, the coating does not significantly affect flexibility or pliability of the product.

The invention also provides a method of reducing pain resulting from implantation of a medical device in a subject, comprising: implanting a medical device coated with a polymerized coating as described herein in the subject, wherein the polymerized coating comprises an analgesic agent, and eluting the analgesic agent from the polymerized coating in the subject.

The invention also provides a method of reducing or preventing infection resulting from implantation of a medical device in a subject, comprising: implanting a medical device coated with a polymerized coating as described herein in the subject, wherein the polymerized coating comprises an antimicrobial agent, and eluting the antimicrobial agent from the polymerized coating in the subject.

The invention also provides a method of treating a hernia in a subject in need thereof, comprising: implanting a soft tissue mesh coated with a polymerized coating as described herein in the subject at the hernia site, wherein the polymerized coating comprises a therapeutic agent, and eluting the therapeutic agent from the polymerized coating at the hernia site in the subject.

The invention also provides a method of reducing adhesion to a surface of a medical device upon implantation in a subject, comprising: implanting a medical device comprising a surface coated thereon a polymerized coating coated with a polymerized coating in the subject, wherein the polymerized coating comprises an anti-adhesion agent, and eluting the anti-adhesion agent from the polymerized coating in the subject. In some embodiments, the anti-adhesion agent is an anti-thrombotic agent. In some embodiments, the anti-adhesion agent is ocriplasmin The invention also provides kits. In some embodiments, the kit comprising a product in a sterile packaging. The product can be any of the man-made products described herein. In some embodiments, the kit further comprises instructions for use.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
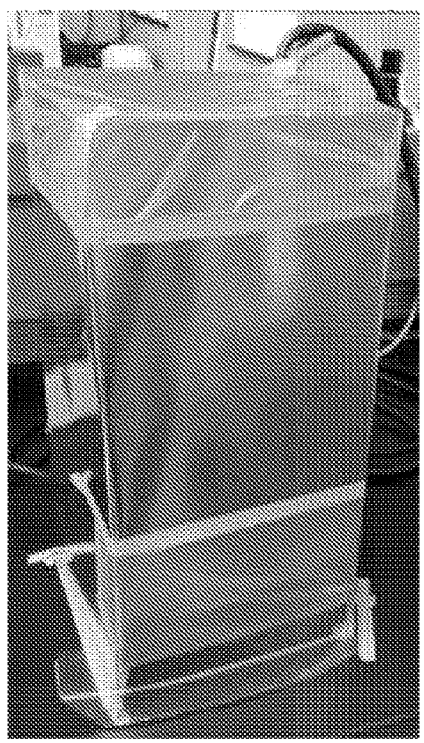
FIGS. 1A and 1B depict an exemplary curing chamber.
Figure 1:
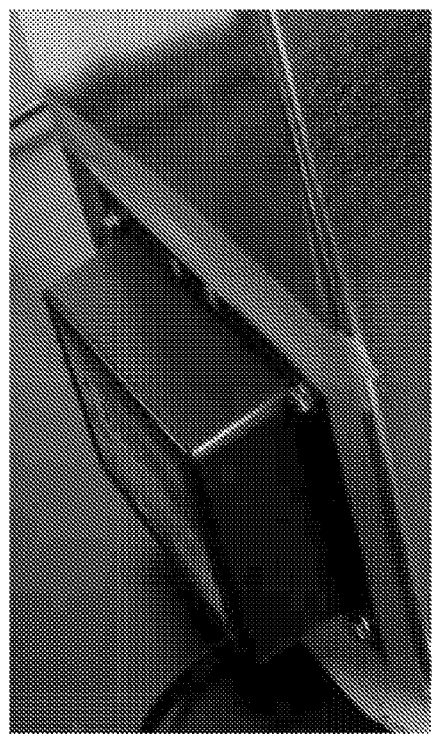

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

DEFINITIONS

As used in the specification and claims, the singular forms "a", "an" and "the" include plural references unless the context clearly dictates otherwise. For example, the term "a cell" includes a plurality of cells, including mixtures thereof.

"Medical device" as used herein can refer to any instrument, apparatus, appliance, material or other article, whether used alone or in combination, including any software necessary for its proper application intended by the manufacturer to be used for human beings for the purpose of: diagnosis, prevention, monitoring, treatment or alleviation of disease, alleviation of pain, diagnosis, monitoring, treatment, alleviation of or compensation for an injury or handicap, investigation, replacement or modification of the anatomy or of a physiological process, control of conception, and which does not achieve its principal intended action in or on the human body by pharmacological, immunological or metabolic means, but which may be assisted in its function by such means.

A medical device may be permanently implantable, temporarily implantable, entirely implantable (such as, for example, an implantable defibrillator), partially implantable (such as, for example, a sensing drainage catheter).

As used herein, the term "biocompatible", when referring to a surface, generally means a surface which causes either no or a minimal reaction when it comes into contact with a human or animal body or its blood, fluids or other biological membranes.

Substantially uniform, as used herein, generally refers to a characteristic of a coating that deviates by no more than 10%, no more than 5%, no more than 1%, no more than 0.5%, no more than 0.1%, no more than 0.05%, or no more than 0.01%. For example, a substantially uniform layer of coating on a surface can mean that the coating on the surface has a thickness at any point of the surface that deviates no more than 10%, no more than 5%, no more than 1%, no more than 0.5%, no more than 0.1%, no more than 0.05%, or no more than 0.01% of the average thickness of the coating on the surface.

Controlled release: As used herein "controlled release" refers to the release of a bioactive compound from a medical device surface at a predetermined rate. Controlled release implies that the bioactive compound does not come off the medical device surface sporadically in an unpredictable fashion and does not "burst" off of the device upon contact with a biological environment (also referred to herein a first order kinetics) unless specifically intended to do so. However, the term "controlled release" as used herein does not preclude a "burst phenomenon" associated with deployment. In some embodiments of the present invention an initial burst of drug may be desirable followed by a more gradual release thereafter. The release rate may be steady state (commonly referred to as "timed release" or zero-order kinetics), that is the drug is released in even amounts over a predetermined time (with or without an initial burst phase) or may be a gradient release. A gradient release implies that the amount of drug released from the device surface changes over time.

As used herein, the term "compatible" generally refers to a composition possessing the optimum, or near optimum combination of physical, chemical, biological and drug release kinetic properties suitable for a controlled release coating made in accordance with the teachings of the present invention. Physical characteristics include durability and elasticity/ductility, chemical characteristics include solubility and/or miscibility and biological characteristics include biocompatibility. The drug release kinetics may be either near zero-order or a combination of first and zero-order kinetics.

As used herein, when any variable occurs more than one time in a chemical formula, its definition on each occurrence is independent of its definition at every other occurrence.

As used herein, a dash ("-") that is not between two letters or symbols is used to indicate a point of attachment for a substituent. For example, —CONH2 is attached through the carbon atom.

As used herein, "optional" or "optionally" is meant that the subsequently described event or circumstance may or may not occur, and that the description includes instances wherein the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, "alkyl" refers to straight chain and branched chain having the indicated number of carbon atoms, usually from 1 to 10 carbon atoms, for example 1 to 8 carbon atoms, such as 1 to 6 carbon atoms. For example C1-C6 alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to six carbons. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is a subset of alkyl, referring to the same residues as alkyl, but having two points of attachment. Alkylene groups will usually have from 2 to 10 carbon atoms, for example 2 to 8 carbon atoms, such as from 2 to 6 carbon atoms. For example, C0 alkylene indicates a covalent bond and C1 alkylene is a methylene group. Hydrocarbon groups containing one or more double bonds such as alkene groups and alkyne groups are each a subset of alkyl.

As used herein, "cycloalkyl" refers to a non-aromatic carbocyclic ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

As used herein, "heterocycloalkyl" refers to a single, non-aromatic ring, usually with 3 to 8 ring atoms, containing at least 2 carbon atoms in addition to 1-3 heteroatoms independently chosen from oxygen, sulfur, and nitrogen, as well as combinations comprising at least one of the foregoing heteroatoms. The ring may be saturated or have one or more carbon-carbon double bonds. Suitable heterocycloalkyl groups include but are not limited to, for example, pyrrolidinyl, morpholinyl, piperidinyl, piperazinyl, azetidinyl, diazepanyl, diazocanyl, pyrrolidinyl, morpholinyl, piperidinyl, piperazinyl, imidazolidinyl, pyrazolidinyl, dihydrofuranyl, and tetrahydrofuranyl. Substituted heterocycloalkyl can also include ring systems substituted with one or more oxo (=O) or oxide (—O—) substituents, such as piperidinyl N-oxide, morpholinyl-N-oxide, 1-oxo-1-thiomorpholinyl and 1,1-dioxo-1-thiomorpholinyl.

"Heterocycloalkyl" also includes bicyclic ring systems wherein one non-aromatic ring, usually with 3 to 7 ring atoms, contains at least 2 carbon atoms in addition to 1-3 heteroatoms independently chosen from oxygen, sulfur, and nitrogen, as well as combinations comprising at least one of the foregoing heteroatoms; and the other ring, usually with 3 to 7 ring atoms, optionally contains 1-3 heteroatoms independently chosen from oxygen, sulfur, and nitrogen and is not aromatic.

As used herein, "aryl" refers to: 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 6-membered carbocyclic aromatic rings fused to a 4- to 8-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g. a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

As used herein, "halo" refers to fluoro, chloro, bromo, and iodo, and the term "halogen" includes fluorine, chlorine, bromine, and iodine.

As used herein, "haloalkyl" refers to alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

As used herein, "heteroaryl" refers to: 5- to 7-membered aromatic, monocyclic rings containing one or more, for example, from 1 to 4, or in certain embodiments, from 1 to 3, heteroatoms chosen from N, O, and S, with the remaining ring atoms being carbon; bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring; and tricyclic heterocycloalkyl rings containing one or more, for example, from 1 to 5, or in certain embodiments, from 1 to 4, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 4- to 8-membered cycloalkyl or heterocycloalkyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, pyridyl, pyrazinyl, pyrimidinyl, pyrazolinyl, imidazolyl, isoxazolyl, oxazolyl, thiazolyl, thiadiazolyl, tetrazolyl, thienyl, benzothiophenyl, furanyl, pyrrolyl, benzofuranyl, benzoimidazolyl, indolyl, pyridazinyl, triazolyl, quinolinyl, quinoxalinyl, pyrazolyl, and 5,6,7,8-tetrahydroisoquinolinyl. Bivalent radicals derived from univalent heteroaryl radicals whose names end in "-yl" by removal of one hydrogen atom from the atom with the free valence are named by adding "-idene" to the name of the corresponding univalent radical, e.g. a pyridyl group with two points of attachment is a pyridylidene.

Substituted heteroaryl also includes ring systems substituted with one or more oxide (—O—) substituents, such as pyridinyl N-oxides.

As used herein, "substituted" refers to any one or more hydrogens on the designated atom or group is replaced with a selection from the indicated group, provided that the designated atom's normal valence is not exceeded. When a substituent is oxo (i.e. =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility.

The term "aromatic" is used in its usual sense, including unsaturation that is essentially delocalized across multiple bonds, such as around a ring.

The term "substituent" refers to an atom, radical or chemical group which replaces a hydrogen in a substituted chemical group, radical, molecule, moiety or compound.

Unless otherwise stated, the term "radical", as applied to any molecule or compound, is used to refer to a part, fragment or group of the molecule or compound rather than to a "free radical". A radical may be linked to another moiety through a covalent bond.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds include Z- and E-forms (or cis- and trans-forms) of compounds with carbon-carbon double bonds. Where compounds described herein exist in various tautomeric forms, the term "compound" is intended to include all tautomeric forms of the compound.

Additionally, useful compositions also, optionally, include one or more salts in an amount required to bring solubility of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

A "polymer" as used herein, can refer to a series of monomers that have been cross-linked or polymerized. The polymer can be a homopolymer or a copolymer. A "copolymer" can refer to a macromolecule produced by the simultaneous or step-wise polymerization of two or more distinct monomers. A homopolymer can refer to a macromolecule produced by the polymerization of a single repeating monomer unit.

"Polymerization", as used herein, generally refers to a process of combining monomers into a covalently bonded chain or network. During the polymerization process, some chemical groups may or may not be lost from each monomer.

As used herein, "treatment" or "treating," or "palliating" or "ameliorating" is used interchangeably herein. These terms refer to an approach for obtaining beneficial or desired results including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made.

A "therapeutic effect", as used herein, refers to a physiologic effect, including but not limited to the cure, mitigation, amelioration, or prevention of disease, or treatment of a symptom of a disease in humans or other animals. Determination of a therapeutically effective amount is well within the capability of those skilled in the art, especially in light of the detailed disclosure provided herein.

Overview

The invention provides products comprising a coating. The coatings described herein can confer improved characteristics to the coated product as compared to a corresponding non-coated product. For example, the coated product can have improved biocompatibility when implanted into a live subject as compared to a corresponding non-coated product. The coating can be non-degradable, which can prevent leaching of the coating components into the surrounding area. Alternatively, the coating can be biodegradable. Further, the coating can be sufficiently durable to withstand the rigors of device implantation and operation (e.g., expansion), without significant degradation. In some cases, the coating is sufficiently lubricious to provide for effective medical device delivery.

Coatings of the present invention can have eluting properties. The coated product can elute one or more therapeutic agents from the product coating. The elution kinetics of the therapeutic agent can be manipulated by controlling the composition and/or structure of the invention coating. For example, the coating can provide for extended release of the one or more therapeutic agents over time. The elution of the one or more therapeutic agents can follow zero order kinetics, e.g., the coating can release the one or more therapeutic agents at a steady rate until the agent(s) are depleted. The elution of the one or more therapeutic agents can follow first order kinetics, wherein the rate of elution can depend in part on the concentration of the therapeutic agent in the coating. Coatings of the invention can elute a therapeutic agent for any duration. For example, invention coatings can elute a therapeutic agent for 0.5 hours, 1 hour, 2 hours, 4 hours, 12 hours, 24 hours (1 day), 2 days, 3 days, 4 days, 5 days, 6 days, 7 days (1 week), 1.5 weeks, 2 weeks, 4 weeks, 1 month, 1.5 months 2 months, 3 months, 4 months, 5 months, 6 months, 7 months 8 months, 9 months, 10 months, 11 months, 12 months (1 year), 1.5 years, 2 years, 5 years, 10 years, or over 10 years. The invention coatings can elute a therapeutic agent for over 1 day, over 1 week, over 2 weeks, over 4 weeks, over 1 month, over 2 months, over 3 months, over 6 months, over 1 year. The coating can elute the one or more therapeutic agents for an unlimited duration. The coated product can elute the one or more therapeutic agents for as long as the product remains implanted in the subject.

The coatings can confer onto the product a wide range of desirable properties, depending on the selection of therapeutic agent to be incorporated into the coatings. The coated product can have, for example, improved antimicrobial properties. The coating on the product can, for example, inhibit or reduce microorganism growth on the product. Inhibition or reduction of microorganism growth on a coating or product can be determined by any method known in the art. For example, a coated surface can be incubated with a microorganism under conditions that are conducive to microorganism growth for a period of time. Microorganism growth on the coated surface can then be detected, visualized (e.g., by microscopy), or evaluated by any means known in the art, and compared to a corresponding uncoated surface incubated with the microorganism. By way of other example, the ability of a coating to inhibit microorganism growth can be assayed via a Kirby-Bauer assay (e.g., KB testing or disk diffusion antibiotic sensitivity testing). The Kirby-Bauer assay can involve swabbing a microorganism culture uniformly across a culture dish. Small pieces of coated materials comprising a therapeutic-eluting coating can be placed on the culture dish. The culture dish can be incubated in an environment conducive to microorganism growth. The antibiotic or anti-infective agent can elute from the coating into the surrounding area, creating a zone of microorganismal growth inhibition which can be readily detected by eye. The size of the zone of inhibition can be positively correlated to the ability of the coating to reduce microorganism growth. The coatings of the invention can inhibit or reduce microorganism growth on the product for 1-30 days, 10-60 days (2 months), 1-6 months, 4-12 months, 0.5-2 years, or longer than 2 years. The coatings can prevent or inhibit the growth of microorganisms such as, e.g., *Escherichia coli, Pseudomonoas aeruginosa, Klebsiella pneumonia, Staphylococcus epidermidis, Candida albicans, Staphylococcus aureus*, Methicilllin resistant Vancomycin-resistant *Staphylococcus aureus* (MRSA), *Enterococcus faecalis* (VRE), Group A *Streptococcus Acinetobacter* baumann. The coated products can prevent development of complications arising from microorganismal growth, e.g., sepsis. Thus, contemplated in the invention are methods for reducing or preventing infection resulting from implantation of a medical device in a subject. The method can comprise implanting a medical device coated with a coating of the invention, wherein the coating comprises an antimicrobial, antiseptic, or anti-infective agent, and eluting the agent in the subject.

The coated product can suppress an inflammatory response upon implantation into a subject. For instance, one common problem associated with device implantation relates to the growth of scar tissue at the site of implantation. By way of example only, vascular grafts commonly induce restenosis, e.g., thickening of the vessel wall, possibly obstructing the vessel. Restenosis is often a significant factor in device failure. A product coated as described herein can prevent or reduce scar tissue growth and can prevent or reduce vessel wall thickening. A coated product as described herein can reduce inflammatory tissue growth, e.g., scar tissue growth or vessel wall thickening, by at least 25%, 30%, 35%, 40%, 45%, 50%, 55%, 60%, 65%, 70%, 75%, 80%, 85%, 90%, 95%, 96%, 97%, 98%, 99%, or 100%. The coated product can minimize inflammatory tissue growth for part or all of the duration of product implantation.

The coated product can minimize pain associated with implantation of the product. For example, the coating of the product can elute an anesthetic, thereby minimizing postoperative pain.

The coating of the product can improve the lifetime of the product. For example, the improved antimicrobial and anti-inflammatory properties of the coating can delay or prevent failure of the product upon implantation. By way of example only, a coated ventral hernia patch comprising a coating of the invention can have an extended lifetime that is at least 10% or 50% longer than a lifetime of a non-coated ventral hernia patch. The coating of the product can reduce the incidence of surgical site infections associated with implantation of a product. By way of example only, surgical implantation of hernia patches are associated with 10-40% incidence of surgical site infection. A coated product of the invention, e.g., a coated hernia patch, can reduce the incidence of surgical site infection as compared to a non-coated hernia patch. For example, a coated hernia patch may reduce the risk of surgical site infection as compared to a non-coated patch by at least 10%, 20%, 30%, 40%, 50%, 60%, 70%, 70%, 80%, 90%, 95%, or more than 95%. A coated hernia patch may reduce the risk of surgical site infection as compared to a non-coated patch by 10-30%, 20-50%, 40-70%, 60-80%, 70-95%, or more than 95%.

The polymerized coatings of the invention can adhere stably to surfaces, without flaking off of the surface. The polymerized coatings of the invention can have minimal or no impact on functionality of the product. Some medical products comprise surfaces that are textured, wherein the textured surface imparts a desired function to the product. For example, soft tissue meshes can comprise a textured surface characterized by nodes, fibrils, filaments, and/or pores. The textured surface can promote integration of tissue from a subject into the mesh. Such nodes, fibrils, filaments, and pores can have submicron dimensions, which may be difficult to coat without occluding the structure of the surface. The polymerized coatings of the invention can be formulated to provide a uniformly thin layer of coating which preserves the dimensions of the textured surface and does not occlude the structure of the surface. Some medical products have a flexibility. The polymerized coatings of the invention can adhere stably to a surface of a flexible medical product, without reducing the flexibility of the product. For example, a product coated with an invention coating can be flexibly bent or distorted without impedance, e.g., mechanical impedance and without cracking or flaking of the coating. By way of other example, the coating can have minimal or no impact on transfer or relay of radiation, electric potential, and/or mechanical forces coating to and from an underlying object, allowing user interface with the underlying object.

Coating Compositions

The invention provides numerous compositions for the preparation of polymer coatings. Such compositions can be referred to herein as "coating compositions". The compositions generally comprise a monomer component and a solvent. The various coating compositions of the invention can be as described herein.

Exemplary Monomers

The monomer component of the invention compositions can comprise at least one monomer. The monomer component can, upon formulation, account for 0.01-50% of an invention composition by wt/wt or wt/vol. The monomer component can account for 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% of the composition upon formulation. The monomer component can account for 0.01-0.5%, 0.1-2%, 1-5%, 5-10%, 10-15%, 15-20%, 20-25%, 25-30%, 30-35%, 35-40%, 40-45%, or 45-50% of the composition upon formulation.

The monomer component can comprise one monomer or more than one monomer. In some cases the monomer component does not comprise more than one monomer. Any monomer that is capable of forming a polymer is contemplated in the invention. The monomer component can comprise a dimethacrylate. The dimethacrylate can be an aromatic dimethacrylate. The aromatic dimethacrylate can be, e.g., any compound of Formulas I-XII:

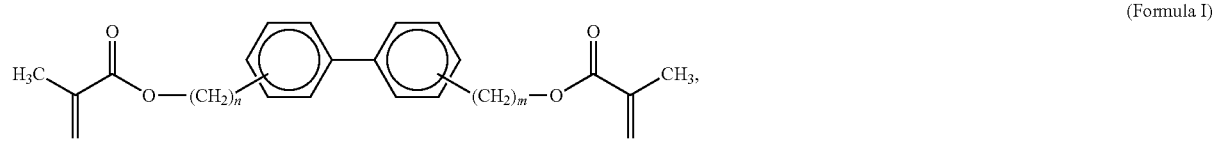

(Formula I)

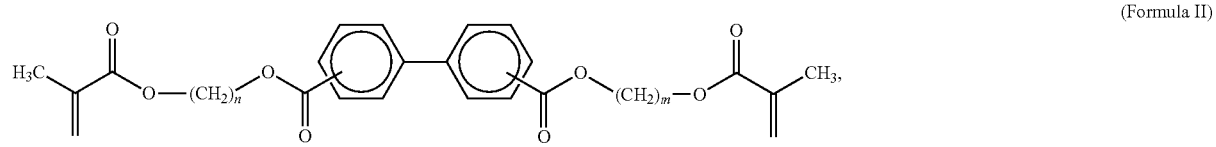

(Formula II)

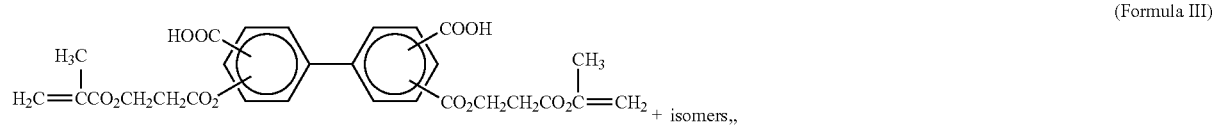

(Formula III)

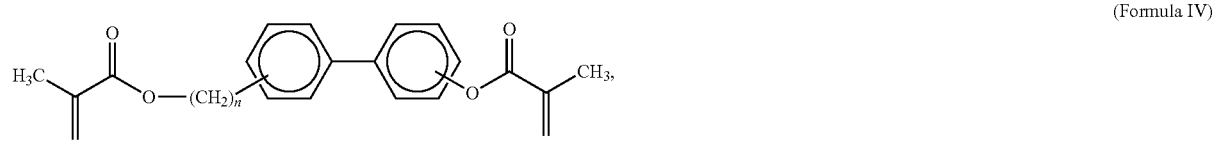

(Formula IV)

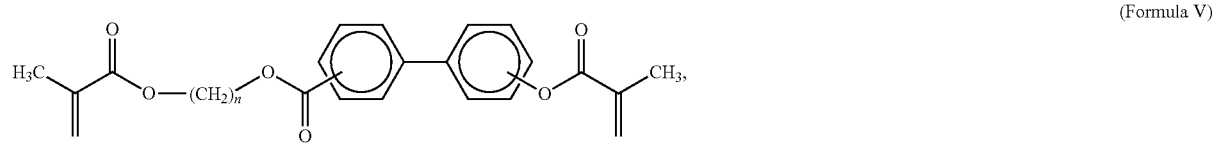

(Formula V)

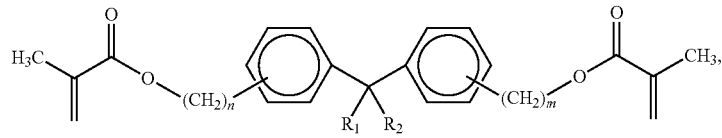

(Formula VI)

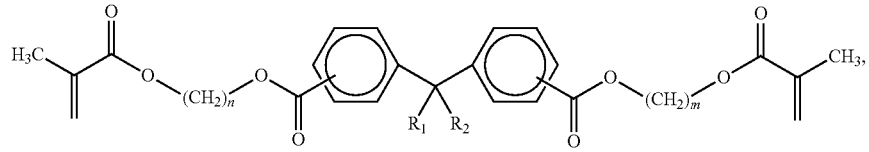

(Formula VII)

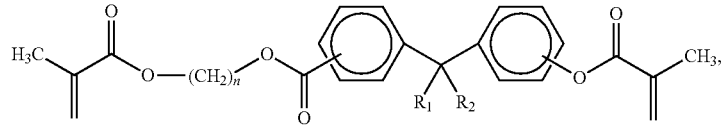

(Formula VIII)

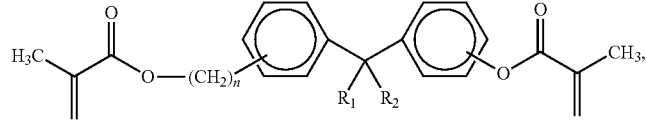

(Formula IX)

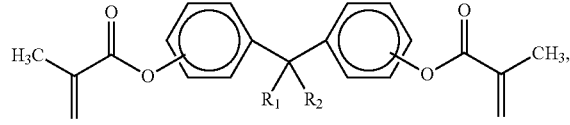

(Formula X)

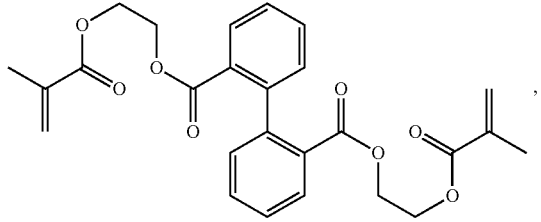 [SMILES: C=C(C)C(=O)OCCOC(=O)c1ccccc1-c1ccccc1C(=O)OCCOC(=O)C(=C)C]

(Formula XI)

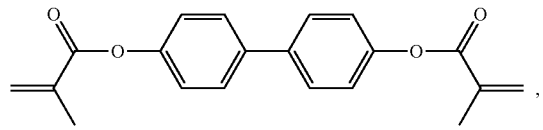

(Formula XII)

and any combinations and/or salts thereof;
wherein each n is independently 1-10;
each m is independently 1-10;
and wherein each $R_1$ and each $R_2$ is independently selected from the group consisting of H, $C_1$-$C_{10}$ alkyl, aryl, and heteroaryl, wherein said $C_1$-$C_{10}$ alkyl, aryl, heteroaryl, when present, is optionally substituted with halo, aryl, heteroaryl, —$NR_{21}R_{22}$, $OR_{23}$, $SR_{24}$, —$S(O)R_{25}$, —$S(O)_2R_{26}$, —$PR_{27}R_{28}$, —$NR_{29}(C=O)R_{30}$, —$NR_{31}S(=O)_2R_{32}$, or —$C(=O)NR_{33}R_{34}$; or $R_1$ and $R_2$ in combination with the carbon to which they are attached form a $C_3$-$C_8$ cycloalkyl or $C_3$-$C_8$ heterocycle; each $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, and $R_{34}$ is independently selected from the group consisting of H, $C_1$-$C_6$ alkyl, —$C(=O)R_{40}$, aryl, and heteroaryl; $R_{40}$ is $C_1$-$C_6$ alkyl. The aromatic dimethacrylate can be biphenyldimethacrylate, bisphenyldimethacrylate, biphenol-dimethacrylate, bisphenol-dimethacrylate, triethyleneglycol dimethacrylate (TEGDMA), urethane dimethacrylate (UDMA), bisphenol-glycidyldimethacrylate (Bis-GMA). The composition can, in some cases, comprise two or more dimethacrylates.

In particular embodiments, the aromatic dimethacrylate is

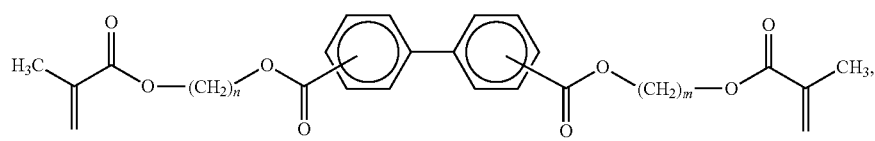

(Formula II)

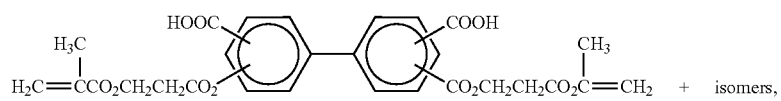

(Formula III)

(Formula XI)
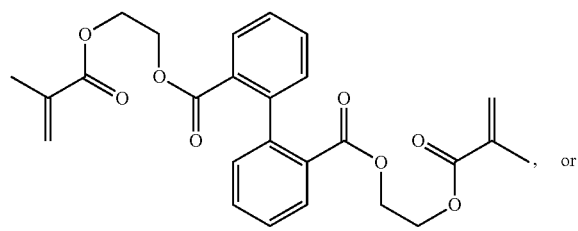
, or (Formula XII)
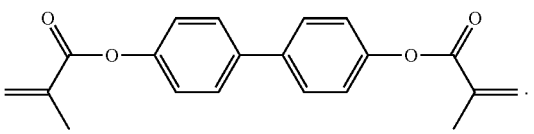

In some embodiments, the compound of Formula II is:

(Formula XIII)
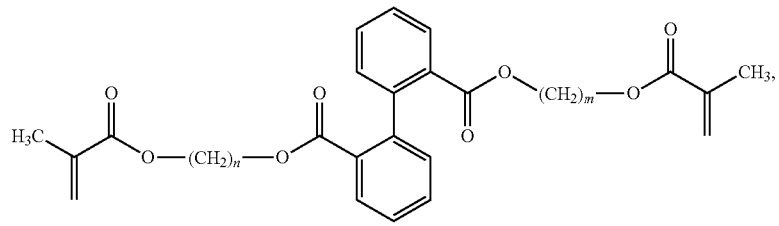

wherein n and m are each independently 2-10. In some embodiments, n and m are each independently 2, 3, 4, 5, or 6. I particular embodiments, at least one of n and m is 2. In more particular embodiments, both n and m are 2. For example, the aromatic dimethacrylate is

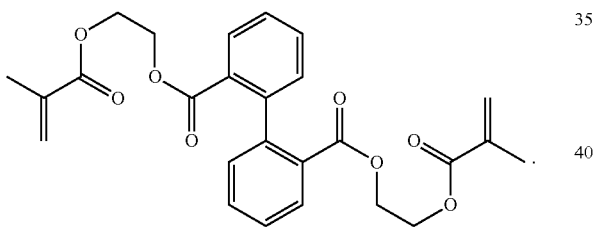

In some embodiments, the monomer is (Formula XIV)
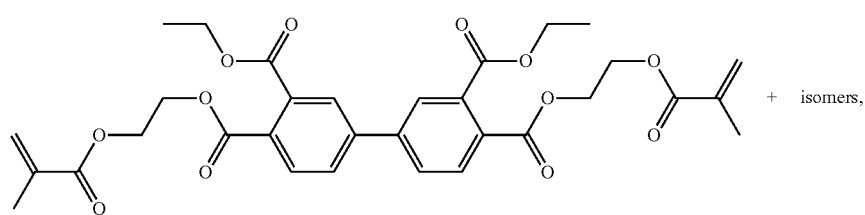 + isomers,

Formula (XV)
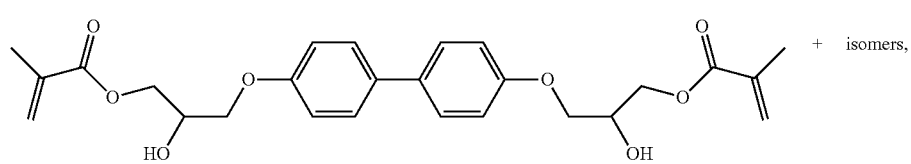 + isomers,

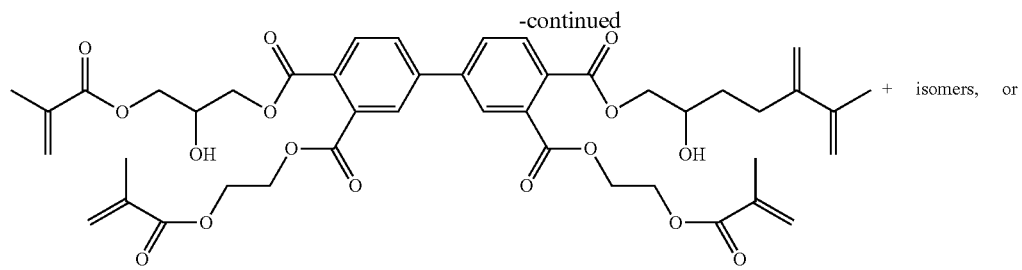 + isomers, or (Formula XVI)

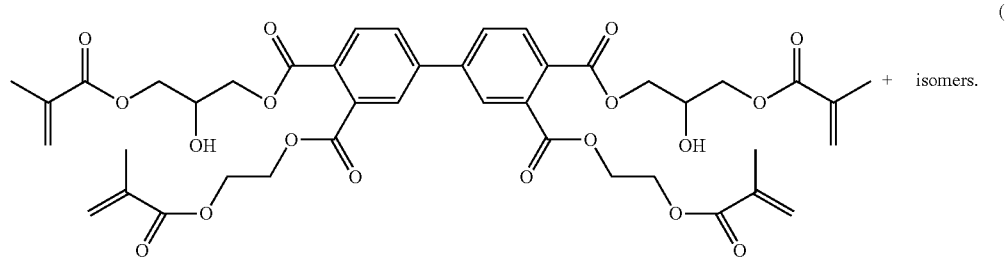 + isomers.

In particular embodiments, the composition comprises a dimethacrylate that is a biphenyldimethacrylate, bisphenyldimethacrylate, biphenol-dimethacrylate, bisphenol-dimethacrylate, or a compound of any of Formulas I-XV. Such dimethacrylates can be referred to interchangeably herein as "BDPM". In some embodiments, BDPM is a compound of any of Formulas II, III, or XI-XV. BDPM can be any compound that comprises a biphenyl or biphenol group and two methacrylate groups. In some embodiments, the BDPM is a compound of Formula III, XII, or both.

The dimethacrylate can, upon formulation, account for 0.01-50% of an invention composition by wt/wt or wt/vol. The dimethacrylate can account for 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% of the composition upon formulation. The dimethacrylate can account for 0.01-0.5%, 0.1-2%, 1-5%, 5-10%, 10-15%, 15-20%, 20-25%, 25-30%, 30-35%, 35-40%, 40-45%, or 45-50% of the composition upon formulation.

Invention compositions can comprise a monomer that is not a dimethacrylate. An invention composition can comprise a dimethacrylate and an additional monomer that is not a dimethacrylate. The monomer that is not a dimethacrylate can be an acrylate or a monomethacrylate. The acrylate can be, e.g., dipentaerythritol pentacrylate phosphate. In some cases, the monomethacrylate comprises a tertiary amine. In some cases, the monomethacrylate is methyl methacrylate, hydroxyethyl methacrylate (HEMA), N-tolylglycine-glycidylmethacrylate (NTG-GMA, including the carboxylic acid form or salts thereof). NTG-GMA salts include, by way of example only, Na-NTG-GMA, Mg-di-NTG-GMA, HOMg-monoNTGGMA). In some embodiments, the composition does not further comprise an acrylate or monomethacrylate.

In particular embodiments, the acrylate or monomethacrylate is N-tolylglycine-glycidylmethacrylate (NTG-GMA), or a carboxylic acid form or salt thereof. For example, in some cases the monomethacrylate is

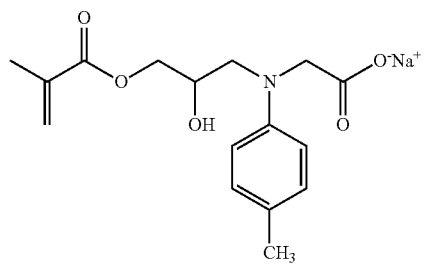

NTG-GMA-sodium salt/n-tolyglycine glycidylmethacrylate or

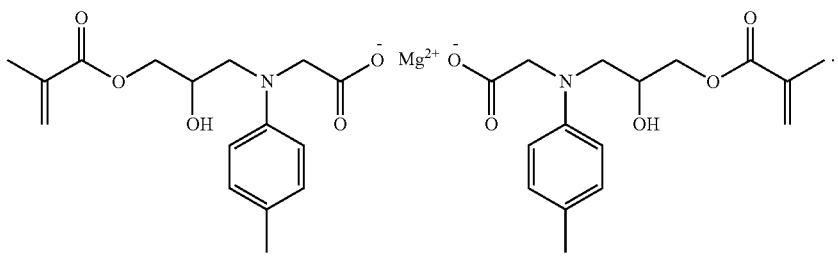

NTG-GMA-magnesium salt

In some embodiments, the acrylate or monomethacrylate is methyl methacrylate. The methyl methacrylate can have the following structure:

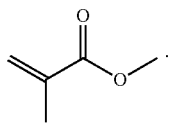

The acrylate or monomethacrylate can account for 0%, 0.1-25%, 0.2-10%, 0.5-2%, 1-5%, or 2-10% of the composition upon formulation. The acrylate or monomethacrylate can, upon formulation account for 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% of the composition upon formulation.

Exemplary Solvents

A wide range of solvents is contemplated for use in the coating compositions of the invention. In some embodiments, a solvent is chosen such that the monomer component is soluble in the solvent. Exemplary solvents include, but are not limited to acetone, water, acetone and water, alcohol (such as, e.g., methanol, ethanol, isopropyl alcohol, butyl alcohol, amyl alcohol, cetyl alcohol, polyhydric alcohols such as ethylene glycol, propylene glycol, glycerol, erythritol, xylitol, mannitol, volemitol, allyl alcohol, geraniol, propargyl alcohol, inositol, menthol, among others), alcohol in water, methylene chloride, trichloromethane, carbon tetrachloride, tetrahydrofuran, acetonitrile benzene, benzene, halogenated benzenes (such as, e.g., chlorobenzene, dichlorobenzene (such as, e.g., o-dichlorobenzene, m-dichlorobenzene), bromobenzene (such as, e.g., o-dibromobenzene, m-dibromobenzene), additionally any mix of halogen groups may be substituted), toluene, hexane, hexane(s), xylene, ethyl acetate, and mixtures thereof (e.g., acetone and alcohol and water). In particular embodiments, the solvent comprises acetone, ethanol, water, dichlorobenzene, or any combination thereof. In some embodiments, the solvent is acetone, water, or a combination thereof. In some cases, the solvent comprises dichloromethane. In some cases, the solvent comprises benzene. In some cases, the solvent comprises dichlorobenzene.

The solvent can be present in an amount that is at least 50-99.9% by wt/wt or wt/vol of the composition upon formulation. For example, the solvent can account for 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9%, of the composition upon formulation. The solvent can account for 50-70%, 60-80%, 75-90%, 85-95%, or 90-99.9% of the composition upon formulation.

Exemplary Polymerization Initiators

The composition can in some cases further comprise a polymerization initiator. The polymerization initiator can be, e.g., a photoinitiator, a chemical initiator, or other polymerization initiator. The polymerization initiator can be present in an amount sufficient to reduce the time required to form the polymerization product (as compared to the rate of polymerization in the absence thereof). In some cases, the amount of polymerization initiator accounts for 0.01-6% of the composition upon formulation. The amount of polymerization initiator can account for 0.05%, 0.1%, 0.2%, 0.3%, 0.4%, 0.5%, 0.6%, 0.7%, 0.8%, 0.9%, 1%, 1.5%, 2%, 3%, 4%, 5%, or 6% of the composition upon formulation. In some embodiments, the polymerization initiator accounts for 0.05-0.2% of the composition upon formulation, for 0.1-0.7% of the composition upon formulation, for 0.5-1%, or for 1-6% of the composition upon formulation. It is understood by those of skill in the art that the amount of polymerization initiator used in the composition will vary depending upon the type of polymerization initiator used, volatility of the one or more solvents used, and the conditions under which the composition is applied to a substrate.

In some cases, the polymerization initiator is a chemical initiator. Exemplary chemical initiators include free radical initiators, e.g., peroxides, azo-initiators, and C—C initiators. In some cases, the polymerization initiator is a photoinitiator. Photoinitiators can include any compounds which release free radicals when exposed to light. Photoinitiators can comprise chemical bonds that are cleavable by photolysis. The photoinitiator can be a Type I or Type II photoinitiator. Type I photoinitiators can undergo a unimolecular bond cleavage upon exposure to light to yield free radicals. Type II photoinitiators can undergo a bimolecular reaction wherein an excited state of the photoinitiator interacts with a second molecule (e.g., a co-initiator) to generate free radicals. The photoinitiators can be induced by light. Exemplary photoinitiators include, e.g., benzoin ethers, benzyl ketals, α-Dialkoxy-aceto-phenones, α-hydroxy-alkyl-phenones, α-amino-alkyl-phenones, acyl-phosphine oxides, benzo-phonenes/amines, thio-xanthones/amines, hydroxy-acetophenones, alkylamino-acetophenones, alpha-haloacetophenones, titanocenes, and other specialty molecules. Photoinitiators suitable in the compositions of the invention include, by way of non-limiting example, Acetophenone, Anisoin, Anthraquinone, Anthraquinone-2-sulfonic acid, sodium salt monohydrate, (Benzene) tricarbonylchromium, Benzil, Benzoin, sublimed, Benzoin ethyl ether, Benzoin isobutyl ether, tech., Benzoin methyl ether, Benzophenone, Benzophenone/1-Hydroxycyclohexyl phenyl ketone, 50/50 blend, 3,3',4,4'-Benzophenonetetracarboxylic dianhydride, sublimed, 4-Benzoylbiphenyl, 2-Benzyl-2-(dimethylamino)-4'-morpholinobutyrophenone, 4,4'-Bis(diethylamino)benzophenone, 4,4'-Bis(dimethylamino)benzophenone, Camphorquinone, 2-Chlorothioxanthen-9-one, (Cumene)cyclopentadienyliron(II) hexafluorophosphate, Dibenzosuberenone, 2,2-Diethoxyacetophenone, 4,4'-Dihydroxybenzophenone, Cat. No. Photoinitiator, 2,2-Dimethoxy-2-phenylacetophenone, 4-(Dimethylamino)benzophenone, 4,4'-Dimethylbenzil, 2,5-Dimethylbenzophenone, tech., 3,4-Dimethylbenzophenone, Diphenyl(2,4,6-trimethylbenzoyl)phosphine oxide/2-Hydroxy-2-methylpropiophenone, 50/50 blend, 4'-Ethoxyacetophenone, 2-Ethylanthraquinone, Ferrocene, 3'-Hydroxyacetophenone, 4'-Hydroxyacetophenone, 3-Hydroxybenzophenone, 4-Hydroxybenzophenone, 1-Hydroxycyclohexyl phenyl ketone, 2-Hydroxy-2-methylpropiophenone, 2-Methylbenzophenone, 3-Methylbenzophenone, Methybenzoylformate, 2-Methyl-4'-(methylthio)-2-morpholinopropiophenone, Phenanthrenequinone, 4'-Phenoxyacetophenone, Thioxanthen-9-one, Triarylsulfonium hexafluoroantimonate salts (mixed), Triarylsulfonium hexafluorophosphate salts (mixed).

The photoinitiator can be a cationic photoinitiator. Cationic photoinitiators can produce a Brönsted or Lewis acid, and can initiate polymerization of cationically polymerizing materials (e.g., epoxies) or resins capable of undergoing crosslinking via polycondensation reactions.

The photoinitiator can be activatable by light having wavelengths in the UV range. The photoinitiator can be activated by light having wavelengths in the UV-A range (e.g., 320-400 nm). The photoinitiator can be activated by light having wavelengths in the UV-B range (e.g., 280-320 nm). The photoinitiator can be activated by light having visible and/or infrared wavelengths. The photoinitiator can be an acetone soluble photoinitiator. Exemplary acetone soluble photoinitiators include Irgacure® 2959; Lucirin® TPO (2,4,6-Trimethylbenzoyldiphenylphosphine oxide); Lucirin® TPO-L (Ethyl-2,4,6-Trimethylbenzoylphenylphosphinate); camphorquinone, and Lucirin® BAPO (Phenyl-bis(2,4,6-trimethylbenzoyl)phosphine oxide). The acetone soluble photoinitiator can be activated in the presence of light having wavelengths above, e.g., 325 nm. Such acetone soluble photoinitiators include those already described herein. A skilled artisan will understand that the compositions of the invention can comprise any combination of polymerization initiators. In some embodiments, the polymerization initiator is camphorquinone. In some embodiments, the camphorquinone accounts for 0.1-3% wt/wt or wt/vol of the composition upon formulation. In particular embodiments, the camphorquinone accounts for 0.1% by wt/vol or vol/vol of the composition upon formulation. In some cases, the photoinitiator is 2-hydroxy-1-[4-(2-hydroxyethoxyl)phenyl]-2-methyl-1-propanone (Igracure 2959), phenylbis(2,4,6-trimethylbenzoyl)phosphine oxide (PTPO, Lucirin® BAPO), or diphenyl(2,4,6-trimethylbenzoyl)phosphine oxide. In particular cases, the photoinitiator is 2-hydroxy-1-[4-(2-hydroxyethoxyl)phenyl]-2-methyl-1-propanone. In some embodiments, the photoinitiator is not phenylbis(2,4,6-trimethylbenzyl)phosphine oxide (PTPO, Lucirin® BAPO).

and a solvent. Exemplary dimethacrylates are described herein. An invention composition can comprise a dimethacrylate and an acrylate or monomethacrylate. Exemplary dimethacrylates are described herein. In such cases, the ratio of dimethacrylate to the acrylate or monomethacrylate in the composition can be 50:1-1:5. The ratio of dimethacrylate to acrylate or monomethacrylate in the composition can be, e.g., 50:1, 45:1, 40:1, 35:1, 30:1, 25:1, 20:1, 19:1, 18:1, 17:1, 16:1, 15:1, 14:1, 13:1, 12:1, 11:1, 10:1, 9:1, 8:1, 7:1, 6:1, 5:1, 4:1. 3:1, 2:1, 1:1, 1:2, 1:3, 1:4, or 1:5. The ratio of aromatic dimethacrylate to acrylate or monomethacrylate in the composition can be 20:1-10:1, 15:1-5:1, 10:1-2:1, 3:1-1:1, 2:1-1:2, or 1:1-1:5.

For example, an invention composition for preparing a polymerized coating can comprise, upon formulation, 1-50% dimethacrylate, 0-25% monomethacrylate, 50-99% solvent, 0.01-5% polymerization initiator. In some embodiments, the coating composition comprises, upon formulation, 4-20% dimethacrylate, 0-20% monomethacrylate, 60-99% solvent, 0.01-5% polymerization initiator. In some embodiments, the coating composition comprises, upon formulation, 5-15% dimethacrylate, 0-10% monomethacrylate, 60-99% solvent, 0.01-5% photoinitiator. In some cases, the composition comprises, upon formulation, 16% dimethacrylate, 1-2% monomethacrylate, 86-87% solvent, 0.2% photoinitiator. In some embodiments, the coating composition comprises, upon formulation, 8% dimethacrylate, 0.5-1% monomethacrylate, 91-92% solvent, 0.1% photoinitiator.

In some embodiments of the composition, the aromatic dimethacrylate is a compound of Formula II:

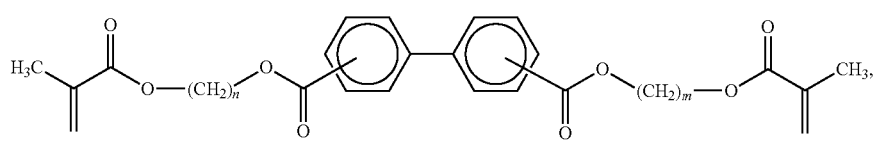

(Formula II)

wherein each n and m are independently 1-10. Each n and m can be independently 1, 2, 3, 4, 5, 6, 7, 8, 9, of 10. Each n and m can be a number between 2-10, 2-6, 2-5, 2-4, or 2-3. In particular embodiments, at least one of n and m is 2. Each n and m can be, e.g., 2.

The compound of Formula II can be:

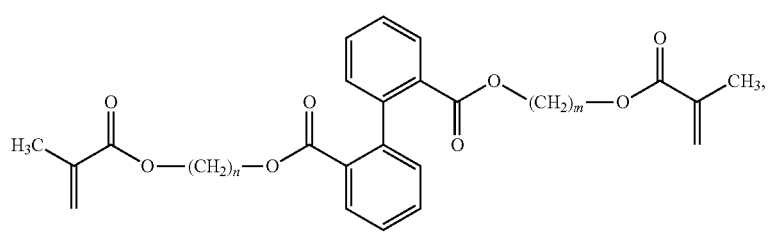

(Formula XIII)

Exemplary Compositions

A skilled artisan will understand that an invention coating can comprise any combination of monomers, solvents, and/or polymerization initiators described herein. Particular embodiments are described below. An invention composition can comprise, for example, an aromatic dimethacrylate wherein n and m are each independently 1-10. In some embodiments, n and m are each independently 2, 3, 4, 5, or 6. In particular embodiments, at least one of n and m is 2. In more particular embodiments, both n and m are 2. For example, the compound can be of Formula XI:

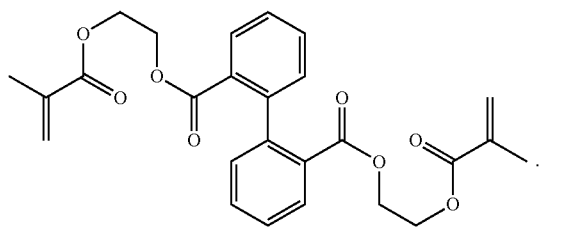

(Formula XI)

Compounds of Formula II, XI, or XIII can be referred to herein as "DMC" compounds. Invention compositions comprising a compound of Formula II, XI, or XIII can be referred to herein as "DMC" compositions. DMC compositions can further comprise a solvent. Exemplary solvents are described herein. The solvent can be, e.g., acetone, dichloromethane, toluene, xylenes, tetrahydrofuran, ethanol, ethyl acetate, and any combination thereof. For example, the solvent of the DMC compositions can be acetone, dichloromethane, or a combination thereof. In some embodiments, the solvent is acetone. In some embodiments, the solvent is dichloromethane.

In some embodiments, the DMC composition further comprises an additional methacrylate. The additional methacrylate can be a monomethacrylate. The monomethacrylate can be, e.g., methyl methacrylate, hydroxyethyl methacrylate (HEMA), N-tolylglycine-glycidylmethacrylate (NTG-GMA, including the carboxylic acid form or salts thereof). NTG-GMA salts include, by way of example only, Na-NTG-GMA, Mg-di-NTG-GMA, HOMg-monoNTGGMA). In some cases, the monomethacrylate is methyl methacrylate. In some cases, the monomethacrylate is NTG-GMA or a carboxylic acid form or salt thereof. For DMC compositions comprising a DMC compound and an additional methacrylate, the ratio of DMC to the additional methacrylate can be, e.g., 50:1, 45:1, 40:1, 35:1, 30:1, 25:1, 20:1, 19:1, 18:1, 17:1, 16:1, 15:1, 14:1, 13:1, 12:1, 11:1, 10:1, 9:1, 8:1, 7:1, 6:1, 5:1, 4:1. 3:1, 2:1, 3:2, 1:1, 2:3, 1:2, 1:3, 1:4, or 1:5. The ratio of DMC to the additional methacrylate in the composition can be 20:1-10:1, 15:1-5:1, 10:1-2:1, 3:1-1:1, 2:1-1:2, 1:1-1:5, 10:1-1:10, or 5:1-1:5. The ratio of DMC to the additional methacrylate can be, e.g., 1:1. In some cases, the DMC compound and additional methacrylate altogether account for 5%, 10%, 15%, 20%, 25%, 30% of the DMC composition by wt/wt or wt/vol upon formulation.

In some embodiments, the DMC composition does not further comprise an acrylate or monomethacrylate. For example, in some embodiments of a DMC composition, a DMC compound (e.g., a compound of Formula II, XI, and/or XIII) accounts for substantially all of the monomer component of the composition. In such embodiments, the DMC compound can account for 5%, 10%, 15%, 20%, 25%, 30% of the DMC composition by wt/wt or wt/vol upon formulation.

DMC compositions can further comprise a polymerization initiator. Exemplary polymerization initiators are described herein. In some cases, the polymerization initiator is 2-hydroxy-1-[4-(2-hydroxyethoxyl)phenyl]-2-methyl-1-propanone.

DMC compositions can comprise upon formulation, by way of example only: 0.1%-50% of a DMC compound, 50-99.9% of a solvent, and 0.001-10% of a polymerization initiator. A DMC composition can comprise upon formulation, by weight: 1%-20% of a DMC compound, 75%-99.9% of a solvent, and 0.01%-5% of a polymerization initiator. A DMC composition can comprise upon formulation, by weight: 15%-15% of a DMC compound, 80%-95% of a solvent, and 0.05%-1% of a polymerization initiator. A DMC composition can comprise upon formulation, by weight: 9%-11% of a DMC compound, 88%-92% of a solvent, and 0.08%-2% of a polymerization initiator. A DMC composition can comprise upon formulation, by weight: 10% of a DMC compound, 89-90% of a solvent, and 0.1-1% of a polymerization initiator. In some cases, the DMC compound is a compound of Formula II. In some cases, the DMC compound is a compound of Formula XI. In some cases, the DMC compound is a compound of Formula XIII. In some cases, the polymerization initiator is 2-hydroxy-1-[4-(2-hydroxyethoxyl)phenyl]-2-methyl-1-propanone. In some cases, the solvent is acetone. In some cases, the solvent is dichloromethane.

DMC compositions that comprise an additional methacrylate can comprise upon formulation, by weight: 1-15% of a DMC compound; 0.01-15% of the additional methacrylate; 50-99% of the solvent; and 0.01-10% of the polymerization initiator. DMC compositions that comprise an additional methacrylate can comprise upon formulation, by weight: 2-10% of a DMC compound; 0.1-10% of the additional methacrylate; 80-99% of the solvent; and 0.01-10% of the polymerization initiator. DMC compositions that comprise an additional methacrylate can comprise upon formulation, by weight: 3-7% of a DMC compound; 1-7% of the additional methacrylate; 84-99% of the solvent; and 0.01-10% of the polymerization initiator. DMC compositions that comprise an additional methacrylate can comprise upon formulation, by weight: 5% of a DMC compound; 5% of the additional methacrylate; 89% of the solvent; and 1% of the polymerization initiator. In some cases, the DMC compound is a compound of Formula II. In some cases, the DMC compound is a compound of Formula XI. In some cases, the DMC compound is a compound of Formula XIII. In some cases, the additional methacrylate is a monomethacrylate. In some cases, the monomethacrylate is methyl methacrylate. In some cases, the polymerization initiator is 2-hydroxy-1-[4-(2-hydroxyethoxyl)phenyl]-2-methyl-1-propanone. In some cases, the solvent is acetone. In some cases, the solvent is dichloromethane.

The DMC compositions can be prepared by any means known in the art. DMC compositions can be prepared by dissolving a DMC compound as described herein and optionally a polymerization initiator as described herein in a solvent. Preparation of a DMC composition can further comprise adding one or more therapeutic agents and/or odorants to the solvent.

An invention composition can comprise BDPM and a monomethacrylate. In such cases, the monomethacrylate can be methyl methacrylate, NTG-GMA, a carboxylic acid form or a salt of NTG-GMA, or any combination thereof. The ratio of BDPM to the monomethacrylate can be 50:1-1:5. In such embodiments, the ratio of BDPM to the monomethacrylate is 50:1, 45:1, 40:1, 35:1, 30:1, 25:1, 20:1, 16:1, 12:1, 10:1, 8:1, 4:1, 3:1, 2:1, 1:1, 1:2, 1:3, 1:4, or 1:5. The ratio of BDPM to NTG-GMA or methyl methacrylate can be 3:1-1:3, can be 2:1-1:2, can be 3:2-2:3, or can be 1:1. In some cases, the composition comprising a BDPM does not further comprise an additional monomer. In some cases, the composition comprising a BDPM does not further comprise an additional monomethacrylate.

In some embodiments of the composition, the BDPM is a compound of Formula III or XII. Such compositions can be referred to herein as "BDPM" compositions or formulations. In some cases, the monomethacrylate of a BDPM composition is:

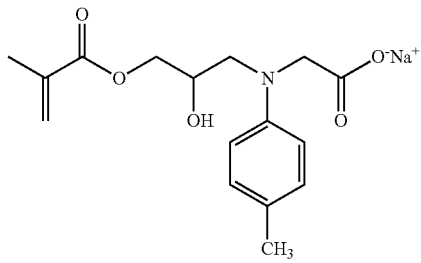

NTG-GMA-sodium salt/n-tolglycine glycidylmethacrylate, or

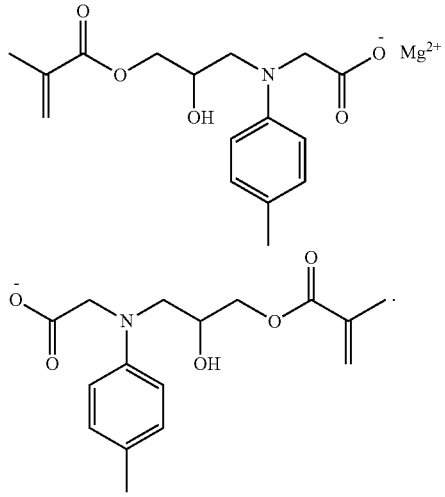

NTG-GMA-magnesium salt

In such embodiments, the ratio of BDPM to the monomethacrylate can be 50:1, 45:1, 40:1, 35:1, 30:1, 25:1, 20:1, 16:1, 12:1, 10:1, 8:1, 4:1, 3:1, 3:2, 2:1, 1:1, 2:3, 1:2, 1:3, 1:4, 1:5, 1:6, 1:7, 1:8, 1:9, or 1:10. In particular embodiments, the ratio of BDPM to the monomethacrylate is 50:1-20:1, 20:1-10:1, 16:1-4:1, or 12:1-2:1.

A BDPM composition can comprise, by way of example only, 8% BDPM, 1% NTG-GMA or salt thereof, and a polymerization initiator in a solvent. For instance, the composition can comprise 8% BDPM, 1% NTF-GMA or a salt thereof, 0.1% camphorquinone, in a solvent. The solvent can comprise benzene, chlorobenzene, acetone, ethanol, water, or mixtures thereof (e.g., 80:20 chlorobenzene/acetone). An exemplary BDPM composition is 8% BDPM, 1% NTG-GMA or a salt thereof, 0.1% camphorquinone, in benzene. Alternatively, the composition can comprise 12% BDPM, 1% NTG-GMA or salt thereof, less than 1% camphorquinone, in a solvent. Also contemplated is a composition comprising 7% BDPM, 0.5-1% NTG-GMA or salt thereof, less than 1% camphorquinone, in a solvent. In some embodiments, the composition comprises 8% BDPM, 0.5% NTG-GMA or salt thereof, and a polymerization initiator in a solvent. In some embodiments the polymerization initiator is camphorquinone. For example, a composition can comprise 8% BDPM, 0.5% NTG-GMA or salt thereof, 0.1% camphorquinone, in a solvent that comprises water, ethanol and acetone. Further contemplated is a composition comprising 8% BDPM, 0.5% NTG-GMA or salt thereof, 0.1% camphorquinone, in a solvent that comprises dichlorobenzene. In some embodiments, the dichlorobenzene is 1,2-dichlorobenzene. The BDPM compound can be a compound of Formula III. The BDPM compound can be a compound of Formula XII.

The invention also provides methods of making a composition for preparing a polymerized coating. In some cases, wherein the coating comprises BDPM, the method comprises combining (a) a first solution comprising a dimethacrylate (e.g., a BDPM dimethacrylate) in a solvent and (b) a second solution comprising a monomethacryate. The first solution, the second solution, or both, can comprise one or more therapeutic agents and/or odorants. Exemplary therapeutic agents and odorants are described herein. The first solution, the second solution, or both, can comprise a polymerization initiator. The first solution can be prepared by dissolving a BDPM dimethacrylate component in a solvent, thereby preparing the first solution. The second solution can be prepared by dissolving a monomethacrylate component in a solvent, thereby preparing the second solution. The first solution, second solution, or both, may then be stably stored in a container prior to the combining. Either the first solution, second solution, or both may be stable stored at room temperature (e.g., at 20-30° C.) for any length of time prior to the combining. In other embodiments, the method comprises mixing a BDPM compound and a monomethacrylate into a solvent to prepare one solution. The one solution can further comprise a polymerization initiator. The one solution can further comprise one or more therapeutic agents and/or odorants. The solution may be heated during the mixing. The solution may be heated, by way of example only, to 40-60° C. A polymerization initiator and/or therapeutic agent (or odorant) can be added to the one solution. The one solution may be stably stored in a container prior to curing. The one solution may be stably stored at room temperature for at least 2-3 days.

In practicing the invention, any of the coating compositions described herein can further comprise one or more additives. Suitable additives may include, by way of non-limiting example only, dyes, pigments, surfactants, adhesives, catalysts, radiopaque materials, radiation absorptive materials, pharmaceutically acceptable salts, pharmaceutically acceptable excipients, polysaccharides, peptides, proteins, amino acids, synthetic polymers, natural polymers, and/or surfactants. Additives which help in reducing or preventing the adhesion of surrounding tissue and organs to the surgical implant (e.g., anti-adhesion compounds) may be particularly useful in the compositions described herein. Non-limiting examples of anti-adhesion molecules include, for example, chemically modified sodium hyaluronate and carboxymethylcellulose (modified with the activating agent 1-(3-dimethylaminopropyl)-3-ethylcarbodimide hydrochloride (EDC) and available commercially as SEPRAFILM® adhesion barrier (Genzyme Corp., Cambridge, Mass.), hyaluronic acid, and collagen.

Therapeutic Agents

In practicing the invention, any of the compositions as described herein can also comprise a therapeutic agent. The therapeutic agent may be soluble in one or more solvents used in preparing the coating. It is contemplated that any therapeutic agent can be incorporated into the coating. Exemplary therapeutic agents include, by way of non-limiting example only, antiplatelets, antithrombins, anti-adhesion agents, cytostatic agents, antiproliferative agents, vasodilators, alkylating agents, antimicrobials, antibiotics, antimitotics, anti-infective agents, antisecretory agents, anti-inflammatory agents, immunosuppressive agents, antimetabolite agents, growth factor antagonists, free radical scavengers, antioxidants, radiotherapeutic agents, anesthetic agents, radiopaque agents, radiolabeled agents, nucleotides, cells, proteins, glycoproteins, hormones, protein receptor agonists or antagonists, anti-stenosis agents, isolates, enzymes, monoclonal antibodies, ribonucleases, nutraceutical agents (e.g. vitamins, minerals, etc.), labeling agents (e.g., contrast agents, radionuclides, fluorescent agents, luminescent agents, magnetic agents), and any combinations thereof. Further, other vasoreactive agents such as nitric oxide releasing agents could also be used.

Exemplary antiplatelets include, e.g., irreversible cyclooxygenase inhibitors, Aspirin, Adenosine diphosphate (ADP) receptor inhibitors, Clopidogrel (Plavix), Prasugrel (Effient), Ticagrelor (Brilinta), Elinogrel, Ticlopidine (Ticlid), Phosphodiesterase inhibitors, Cilostazol (Pletal), Glycoprotein IIB/IIIA inhibitors (intravenous use only), Abciximab (ReoPro), Eptifibatide (Integrilin), Tirofiban (Aggrastat), Adenosine reuptake inhibitors, PAR-1 or PAR-4 antagonists, GPVI antagonists, Dipyridamole (Persantine), Thromboxane inhibitors, Thromboxane synthase inhibitors, Thromboxane receptor antagonists, Terutroban, and mixtures thereof.

Exemplary antithrombins include, e.g., heparin, aspirin, hirudin, dabigatran, Enoxaparin, anti-Xa, anti-XIIa, anti-IXa agents, GPIIb/IIIa receptor inhibitor as tirofiban, eptifibatide, cilostazol, plavix, Ticlid, urokinase, and PPack (dextrophenylalanine proline arginine chloromethylketone. Suitable anti-cancer agents include methotrexate, purine, pyridine, and botanical (e.g. paclitaxel, colchicines and triptolide), epothilone, antibiotics, and antibodies.

Anti-adhesion agents can include any agent that blocks and/or inhibits an adhesion molecule such as, e.g., cell adhesion molecules (CAM), intercellular adhesion molecules (ICAM), vascular cell adhesion molecules (VCAM), and others. Agents that block such adhesion molecules can include, e.g., antibodies, RNAi agents. Exemplary anti-adhesion agents include, by way of example only, ocriplasmin.

Cytostatic agents (e.g., alkylating agents and other agents) are described herein. Exemplary vasodilators include, e.g., Hydralazine, Minoxidil. Exemplary antimicrobials include, e.g., chlorhexidine diacetate, silver carbonate, and antimicrobial peptides (AMPs).

Exemplary anti-inflammatory agents include, e.g., steroids, non-steroidal anti-inflammatory drugs (NSAIDs), and Immune Selective Anti-Inflammatory Derivatives (ImSAIDs). Exemplary steroids include glucocorticoids and corticosteroids, such as, e.g., hydrocortisone, hydrocortisone acetate, cortisone acetate, tixocortol pivalate, prednisolone, methylprednisolone, and prednisone, meprednisone, triamcinolone, paramethasone, fluprednisolone, betamethasone, dexamethasone, fludrocortisone, desoxycorticosterone, Triamcinolone acetonide, triamcinolone alcohol, mometasone, amcinonide, budesonide, desonide, fluocinonide, fluocinolone acetonide, and halcinonide, betamethasone, betamethasone sodium phosphate, dexamethasone sodium phosphate, and fluocortolone, Hydrocortisone-17-valerate, halometasone, alclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate, Hydrocortisone-17-butyrate, hydrocortisone-17-aceponate, hydrocortisone-17-buteprate, and prednicarbate. Exemplary NSAIDs include, e.g., Aspirin (acetylsalicylic acid), Diflunisal, Salsalate, Ibuprofen, Dexibuprofen, Naproxen, Fenoprofen, Ketoprofen, Dexketoprofen, Flurbiprofen, Oxaprozin, Loxoprofen, Indomethacin, Tolmetin, Sulindac, Etodolac, Ketorolac, Diclofenac, Nabumetone, Piroxicam, Meloxicam, Tenoxicam, Droxicam, Lornoxicam, Isoxicam, Mefenamic acid, Meclofenamic acid, Flufenamic acid, Tolfenamic acid, Celecoxib, Rofecoxib, Valdecoxib, Parecoxib, Lumiracoxib, Etoricoxib, Firocoxib, Paracetamol, Nimesulide, Licofelone acts, H-harpagide, Lysine clonixinate, and mixtures thereof. Exemplary ImSAIDs include, e.g., submandibular gland peptide-T, tripeptide FEG (Phe-Glu-Gly) and its D-isomer feG. Illustrative anti-inflammatory agents also include COX-2 inhibitors, such as nimesulide, NS-398, flosulid, L-745337, celecoxib, rofecoxib, SC-57666, DuP-697, parecoxib sodium, JTE-522, valdecoxib, SC-58125, etoricoxib, RS-57067, L-748780, L-761066, APHS, etodolac, meloxicam, S-2474, and mixtures thereof; glucocorticoids, such as and mixtures thereof; the anti-inflammatory agent rapamycin; and mixtures thereof.

Exemplary immunosuppressive agents include, e.g., Azathioprine, cyclosporine, interferon, opioids, TNF-binding proteins, infliximab (Remicade), etanercept (Enbrel), or adalimumab, Mycophenolic acid, Fingolimod, Myriocin.

Exemplary antibiotics include, e.g., amoxicillin, ampicillin, aminoglycosides such as gentamycin or neomycin, azithromycin, aztreonam, aclarubicin, actinomycin D, actinoplanone, adriamycin, aeroplysinin derivative, amrubicin, anthracycline, azinomycin-A, bisucaberin, bleomycin sulfate, bryostatin-1, cefepime, cefixime, ceftriaxone, cephalosporin C, cephazolin, cephamandol, chloramphenicol, ciprofloxacin, clindamycin, calichemycin, chromoximycin, dactinomycin, daunorubicin, ditrisarubicin B, doxorubicin, doxorubicin-fibrinogen, doxycycline, erythromycin, imipenem, meropenem, metronidazole, netilmycin, rifampicin, spectinomycin, penicillins such as oxacillin or mezlocillin, streptomycin, tetracycline, tobramycin, trimethoprim, TYGACIL® (tigecycline; Wyeth, Madison, N.J.), elsamicin-A, epirubicin, erbstatin, esorubicin, esperamicin-Al, esperamicin-Alb, fostriecin, glidobactin, gregatin-A, grincamycin, herbimycin, idarubicin, illudins, kazusamycin, kesarirhodins, menogaril, mitomycin, neoenactin, oxalysine, oxaunomycin, peplomycin, pilatin, pirarubicin, porothramycin, pyrindanycin A, rapamycin (e.g., sirolimus), rapamycin derivatives or analogs such as temsirolimus, umirolimus, zotarolimus, everolimus, deforolimus, rhizoxin, rodorubicin, sibanomicin, siwenimycin, sorangicin-A, sparsomycin, talisomycin, terpentecin, thrazine, tricrozarin A, and zorubicin.

Anti-infective agents useful in the invention include, e.g., pyrimidine analogs. A "pyrimidine analog", as used herein, generally refers to a compound with a pyrimidine ring structure (1,3-diazine) substituted with one or more atoms or chemical groups or oxidized at one or more carbons in the pyrimidine ring structure.

In certain embodiments, the pyrimidine analog contains a halogen substituent, such as F, Cl, Br, or I, at a carbon in the pyrimidine ring structure. In certain embodiments, the pyrimidine analog contains at least one F substituent at a carbon of its pyrimidine ring structure and is referred to as a "fluoropyrimidine." Exemplary fluoropyrimidines include, but are not limited to, 5-FU, 5-FUdR (5-fluoro-deoxyuridine; floxuridine), fluorouridine triphosphate (5-FUTP), fluorodeoxyuridine monophosphate (5-dFUMP), 5-fluorocytosine, 5-fluorothymidine, capecitabine, trifluridine, and trifluorothymidine. Other halogenated pyrimidine analogs include, but are not limited to, 5-bromodeoxyuridine (5-BudR), 5-bromouracil, 5-chlorodeoxyuridine, 5-chlorouracil, 5-iododeoxyuridine (5-IudR), 5-iodouracil, 5-bromocytosine, 5-chlorocytosine, and 5-iodocytosine.

In certain embodiments, the pyrimidine analog is a uracil analog. A "uracil analog" refers to a compound that contains a uracil ring structure substituted with one or more atoms or chemical groups. In certain embodiments, the uracil analog contains a halogen substituent, such as F, Cl, Br, or I. In certain embodiments, the uracil analog contains an F substituent, and is referred to as a "fluorouracil analog." Exemplary fluorouracil analogs include, but are not limited to, 5-FU, carmofur, doxifluridine, emitefur, tegafur, and floxuridine.

Other anti-infectives which may be useful in the invention include, e.g., chlorhexidine, silver compounds, silver ions, silver particles, or other metallic compounds, ions or particles (such as gold).

Chemotherapeutic agents may also serve as anti-infective agents. Exemplary classes of chemotherapeutics useful in combination with pyrimidine analogs are uracil analogs, anthracyclins, folic acid antagonists, podophyllotoxins, camptothecins, hydroxyureas, and platinum complexes.

Exemplary anthracyclines include but are not limited to doxorubicin, daunorubicin, idarubicin, epirubicin, pirarubicin, zorubicin, and carubicin. Other suitable anthracyclines are anthramycin, mitoxantrone, menogaril, nogalamycin, aclacinomycin A, olivomycin A, chromomycin A3, and plicamycin.

Exemplary folic acid antagonists include but are not limited to methotrexate or derivatives or analogs thereof, such as edatrexate, trimetrexate, raltitrexed, piritrexim, denopterin, tomudex, and pteropterin.

Exemplary platinum complexes are described in U.S. Pat. Nos. 5,409,915 and 5,380,897, hereby incorporated by reference. Platinum complexes such as cisplatin, carboplatin, oxaliplatin, and miboplatin are contemplated in the present invention.

Other anti-infective agents include, e.g., silver compounds (e.g., silver chloride, silver nitrate, silver oxide), silver ions, silver particles, gold compounds (such as gold chloride, auranofin), gold ions, gold particles, iodine, povidone/iodine, chlorhexidine, 2-p-sulfanilyanilinoethanol, 4,4'-sulfinyldianiline, 4-sulfanilamidosalicylic acid, acediasulfone, acetosulfone, amikacin, amoxicillin, amphotericin B, ampicillin, apalcillin, apicycline, apramycin, arbekacin, aspoxicillin, azidamfenicol, azithromycin, aztreonam, bacitracin, bambermycin(s), biapenem, brodimoprim, butirosin, capreomycin, carbenicillin, carbomycin, carumonam, cefadroxil, cefamandole, cefatrizine, cefbuperazone, cefclidin, cefdinir, cefditoren, cefepime, cefetamet, cefixime, cefmenoxime, cefminox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, chloramphenicol, chlortetracycline, ciprofloxacin, clarithromycin, clinafloxacin, clindamycin, clomocycline, colistin, cyclacillin, dapsone, demeclocycline, diathymosulfone, dibekacin, dihydrostreptomycin, dirithromycin, doxycycline, enoxacin, enviomycin, epicillin, erythromycin, flomoxef, fortimicin(s), gentamicin(s), glucosulfone solasulfone, gramicidin S, gramicidin(s), grepafloxacin, guamecycline, hetacillin, imipenem, isepamicin, josamycin, kanamycin(s), leucomycin(s), lincomycin, lomefloxacin, lucensomycin, lymecycline, meclocycline, meropenem, methacycline, micronomicin, midecamycin(s), minocycline, moxalactam, mupirocin, nadifloxacin, natamycin, neomycin, netilmicin, norfloxacin, oleandomycin, oxytetracycline, p-sulfanilylbenzylamine, panipenem, paromomycin, pazufloxacin, penicillin N, pipacycline, pipemidic acid, polymyxin, primycin, quinacillin, ribostamycin, rifamide, rifampin, rifamycin SV, rifapentine, rifaximin, ristocetin, ritipenem, rokitamycin, rolitetracycline, rosaramycin, roxithromycin, salazosulfadimidine, sancycline, sisomicin, sparfloxacin, spectinomycin, spiramycin, streptomycin, succisulfone, sulfachrysoidine, sulfaloxic acid, sulfamidochrysoidine, sulfanilic acid, sulfoxone, teicoplanin, temafloxacin, temocillin, tetracycline, tetroxoprim, thiamphenicol, thiazolsulfone, thiostrepton, ticarcillin, tigemonam, tobramycin, tosufloxacin, trimethoprim, trospectomycin, trovafloxacin, tuberactinomycin, vancomycin, azaserine, candicidin(s), chlorphenesin, dermostatin(s), filipin, fungichromin, mepartricin, nystatin, oligomycin(s), ciproflaxacin, norfloxacin, ofloxacin, pefloxacin, enoxacin, rosoxacin, amifloxacin, fleroxacin, temafloaxcin, lomefloxacin, perimycin A or tubercidin, and the like.

Exemplary anti-proliferative (e.g., anti-neoplastic) agents include, but are not limited to tubulin interacting agents, topoisomerase inhibitors and agents, acitretin, alstonine, amonafide, amphethinile, amsacrine, ankinomycin, antineoplaston, aphidicolin glycinate, asparaginase, angiopeptin, acetylsalicylic acid, baccharin, batracylin, benfluoron, benzotript, bromofosfamide, caracemide, carmethizole hydrochloride, chlorsulfaquinoxalone, clanfenur, claviridenone, crisnatol, curaderm, cytarabine, cytocytin, dacarbazine, datelliptinium, dihaematoporphyrin ether, dihydrolenperone, dinaline, distamycin, docetaxel, elliprabin, elliptinium acetate, enoxaprin, epothilones, ergotamine, etoposide, etretinate, fenretinide, gallium nitrate, genkwadaphnin, hexadecylphosphocholine, hirudin, HDAC inhibitors, homoharringtonine, hydroxyurea, ilmofosine, isoglutamine, isotretinoin, leukoregulin, lonidamine, merbarone, merocyanlne derivatives, methylanilinoacridine, minactivin, mitonafide, mitoquidone, mitoxantrone, mopidamol, motretinide, N-(retinoyl)amino acids, N-acylated-dehydroalanines, nafazatrom, nocodazole derivative, octreotide, oquizanocine, paclitaxel, pancratistatin, pazelliptine, piroxantrone, polyhaematoporphyrin, polypreic acid, probimane, procarbazine, proglumide, razoxane, retelliptine, spatol, spirocyclopropane derivatives, spirogermanium, strypoldinone, superoxide dismutase, teniposide, thaliblastine, tocotrienol, topotecan, ukrain, vinblastine sulfate, vincristine, vindesine, vinestramide, vinorelbine, vintriptol, vinzolidine, withanolides, and monoclonal antibodies capable of blocking smooth muscle cell proliferation.

Exemplary antimetabolite agents include, e.g., 5-FU-fibrinogen, acanthifolic acid, aminothiadiazole, brequinar sodium, carmofur, cyclopentyl cytosine, cytarabine phosphate stearate, cytarabine conjugates, dezaguanine, dideoxycytidine, dideoxyguanosine, didox, doxifluridine, fazarabine, floxuridine, fludarabine phosphate, 5-fluorouracil, N-(2'-furanidyl)-5-fluorouracil, inhibitors of essential amino acids, isopropyl pyrrolizine, methobenzaprim, methotrexate, norspermidine, ornithine decarboxylantion inhibitors, pentostatin, piritrexim, plicamycin, thioguanine, tiazofurin, trimetrexate, tyrosine kinase inhibitors, and uricytin.

Exemplary alkylating agents include, e.g., aldo-phosphamide analogues, altretamine, anaxirone, bestrabucil, budotitane, carboplatin, carmustine, chlorambucil, cisplatin, cyclophosphamide, cyplatate, diphenylspiromustine, diplatinum cytostatic, elmustine, estramustine phosphate sodium, fotemustine, hepsul-fam, ifosfamide, iproplatin, lomustine, mafosfamide, mitolactol, oxaliplatin, prednimustine, ranimustine, semustine, spiromustine, tauromustine, temozolomide, teroxirone, tetraplatin and trimelamol.

Non-limiting examples of monoclonal antibodies include rituximab, trastuzumab, gemtuzumab, ozogamicin, alemtuzumab, ibritumomab, tiuxetan, tositumomab, cetuximab, bevacizumab, panitumumab, and ofatumumab.

Exemplary anesthetic agents include, e.g., procaine, amethocaine, cocaine, lidocaine (also known as Lignocaine), prilocaine, bupivacaine, levobupivacaine, ropivacaine, mepivacaine, dibucaine, Barbiturates, Amobarbital, Methohexital, Thiamylal, Thiopental, Benzodiazepines, Diazepam, Lorazepam, Midazolam, Etomidate, Ketamine, Propofol, Alfentanil, Fentanyl, Remifentanil, Sufentanil, Buprenorphine, Butorphanol, diacetyl morphine, Hydromorphone, Levorphanol, Meperidine, Methadone, Morphine, Nalbuphine, Oxycodone, Oxymorphone, Pentazocine, and mixtures thereof.

Other suitable therapeutic agents include, e.g., Methotrexate, Azathioprine, vincristine, VinBlastine, Fluorouracil, Adriamycin, and Mutamycin. The therapeutic agent can be an anticoagulant. Exemplary anticoagulant drugs include Heparin, Coumadin, Protamine, and Hirudin.

The therapeutic agent can be an antifungal agent. Illustrative anti-fungal agents include polyene antifungals, such as amphotericin B, candicidin, filipin, hamycin, natamycin, nystatin, rimocidin, imidaxole, triazole and thiazole antifungals. Imidazole antifungal agents include bifonazole, butoconazole, blotrimazole, econazole, fenticonazole, isoconazole, ketoconazole, miconazole, omoconazole, oxiconazole, sertaconazole, sulconazole and tioconazole. Triazole based antifungal agents include albaconazole, fluconazole, isavuconazole, itraconazole, posaconazole, ravuconazole, terconazole and voriconazole. Thiazole antifungal agents include abafungin. Allylamine antifungal agents may also be used in the protective coating of the invention. Non-limiting examples of allylamine antifungal agents include amorolfin, butenafine, naftifine and terbinafine. The coating composition may also employ echinocandins fungal agents such as, e.g., anidulafungin, caspofungin and micafungin. Other antifungal agents that may be used with the polymeric composition of the present invention include benzoic acid, ciclopirox, flucytosine or 5-fluorocytosine, griseofulvin, haloprogin, polygodial, crystal violet, tolnaftate and undecylenic acid essential oils possessing antifungal properties may also be used in the polymeric composition of the current invention. Non-limiting examples of such essential oils include oregano, allicin, citronella oil, coconut oil, lugol's iodine, lemon myrtle, neem seed oil, olive leaf, orange oil, palmarosa oil, patchouli, selenium, and tea tree oil.

The coating may also comprise an anti-viral agent. Antiviral agents that may be used in the coatings of the current invention include aciclovir, amantadine, antiviral proteins, alovudine, arbidol, brivudine, 5-bromouridine, cidofovir, daclatasvir, template:DNA antivirals, docosanol, double-stranded RNA (ds RNA) activated caspase oligomerizer (DRACO), famciclovir, FGI-104, fialuridine, fomivirsen, foscarnet, FV-100, ganciclovir, ibacitabine, idoxuridine, imiquimod, inosine, inosine pranobex, interferon, interferon alfa-2b, interferon alfacon-1, interferon alpha-n3, interferon type I, interferon type II, interferon type III, interferon-gamma, maribavir, methisazone, moroxydine, nucleoside analogue, oragen, peginterferon alfa-2a, pegylated interferon, penciclovir, pleconaril, podophyllotoxin, prosetta, PSI-6130, reciGen, resiquimod, ribavirin, rintatolimod, template:RNA antivirals, semapimod, setrobuvir, simeprevir, sofosbuvir, sorivudine, tecovirimat, taribavirin, telbivudine, tenofovir alafenamide fumarate, theaflavin, tilorone, trifluridine, tromantadine, valaciclovir, valganciclovir and vidarabine.

Antiseptics could also be used as therapeutic agents with the coatings of the present disclosure. Some common antiseptics that may be use include alcohols (like ethanol, 1-propanol, 2-propanol), quaternary ammonium salts also known as quats or QAC's (For example benzalkonium chloride (BAC), cetyl trimethylammonium bromide (CTMB), cetylpyridinium chloride (Cetrim, CPC) and benzethonium chloride (BZT)), boric acid, brilliant green, chlorhexidine gluconate, hydrogen peroxide, iodine (for example providone-iodine and Lugol's iodine), mercurochrome, manuka money, octenidine dihydrochloride, phenol (carbolic acid) compounds, polyhexanide (polyhexamethylene biguanide, PHMB), sodium chloride, sodium hyposhlorite, calcium hypochlorite and sodium bicarbonate.

The invention coatings may also be formulated to include one or more disinfectants. Non-limiting examples of the disinfectants that may be used in the polymeric composition of the present invention include alcohols (like ethanol and propanol), aldehydes (such as formaldehyde, ortho-phthaldehyde and glutataldehyde), oxidizing agents (for example Sodium hypochlorite, calcium hypochlorite, chloramine, chloramine-T, chlorine dioxide, hydrogen peroxide, hydrogen peroxide vapor, iodine, peracetic acid, performic acid, potassium permanganate, potassium peroxymonosulfate), phenolics (for example phenol, o-Phenylphenol, chloroxylenol, hexachlorophene, thymol, amylmetacresol, and 2,4-dichlorobenzyl alcohol), Quats (such as benzalkonium chloride), silver, lactic acid, and sodium bicarbonate.

The therapeutic agent can be a gene therapy formulation, such as, e.g., Keratin 8, VEGF, and EGF, PTEN, Pro-UK, NOS, or C-myc.

The coating compositions described herein can comprise a plurality of therapeutic agents. It is understood that any combination of the therapeutic agents described herein are contemplated in the invention.

The compositions described herein can comprise one or more odorants. An odorant can be any chemical entity having an odor. The chemical can be sufficiently volatile to enable contact with an olfactory system of a subject. Odorants can be found in, e.g., food, wine, spices, perfumes, essential oils, fragrance oils, substances that are secreted from an animal, plants, and other species. The odorant can, for example, be found in substances (e.g., urine) secreted from a predator. The odorant can be found in, without limitation, coyote urine, fox urine, bobcat urine, raccoon urine, mountain lion urine, cougar urine, panther urine, wolf urine, bear urine, whitetail deer urine, whitetail doe in heat urine, whitetail buck in rut urine, and/or moose urine.

The coating compositions described herein can comprise any amount of therapeutic agent(s) and/or odorants. For example, the coating compositions described herein can comprise 1 pg, 5 pg, 10 pg, 20 pg, 30 pg, 40 pg, 50 pg, 60 pg, 70 pg, 80 pg, 90 pg, 100 pg, 200 pg, 300 pg, 400 pg, 500 pg, 600 pg, 700 pg, 800 pg, 900 pg, 1000 pg (1 ng), 5 ng, 10 ng, 20 ng, 30 ng, 40 ng, 50 ng, 60 ng, 70 ng, 80 ng, 90 ng, 100 ng, 200 ng, 300 ng, 400 ng, 500 ng, 600 ng, 700 ng, 800 ng, 900 ng, 1000 ng (1 µg), 5 µg, 10 µg, 20 µg, 30 µg, 40 µg, 50 µg, 60 µg, 70 µg, 80 µg, 90 µg, 100 µg, 200 µg, 300 µg, 400 µg, 500 µg, 600 µg, 700 µg, 800 µg, 900 µg, 1000 µg (1 mg), 5 mg, 10 mg, 20 mg, 30 mg, 40 mg, 50 mg, 60 mg, 70 mg, 80 mg, 90 mg, 100 mg, 200 mg, 300 mg, 400 mg, 500 mg, 600 mg, 700 mg, 800 mg, 900 mg, 1000 mg (1 g), 5 g 10 g, 20 g, 30 g, 40 g, 50 g, 60 g, 70 g, 80 g, 90 g, or 100 g of the therapeutic agent(s). The coating compositions described herein can comprise 1 pg-100 pg, 50 pg-1 ng, 0.5 ng-500 ng, 100 ng-5 µg, 1 µg-50 µg, 20 µg-500 µg, 100 µg-1 mg, 0.5 mg-100 mg, 50 mg-1 g, 0.5 g-10 g, 1-100 g of the therapeutic agent(s) and/or odorant(s). A therapeutic agent and/or odorant may be present in the coating composition at a concentration of 1 pg/ml, 5 pg/ml, 10 pg/ml, 20 pg/ml, 30 pg/ml, 40 pg/ml, 50 pg/ml, 60 pg/ml, 70 pg/ml, 80 pg/ml, 90 pg/ml, 100 pg/ml, 200 pg/ml, 300 pg/ml, 400 pg/ml, 500 pg/ml, 600 pg/ml, 700 pg/ml, 800 pg/ml, 900 pg/ml, 1000 pg/ml (1 ng/ml), 5 ng/ml, 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 200 ng/ml, 300 ng/ml, 400 ng/ml, 500 ng/ml, 600 ng/ml, 700 ng/ml, 800 ng/ml, 900 ng/ml, 1000 ng/ml (1 μg/ml), 5 μg/ml, 10 μg/ml, 20 μg/ml, 30 μg/ml, 40 μg/ml, 50 μg/ml, 60 μg/ml, 70 μg/ml, 80 μg/ml, 90 μg/ml, 100 μg/ml, 200 μg/ml, 300 μg/ml, 400 μg/ml, 500 μg/ml, 600 μg/ml, 700 pg/ml, 800 μg/ml, 900 μg/ml, 1000 μg/ml (1 mg/ml), 5 mg/ml, 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 200 mg/ml, 300 mg/ml, 400 mg/ml, 500 mg/ml, 600 mg/ml, 700 mg/ml, 800 mg/ml, 900 mg/ml, 1000 mg/ml. A therapeutic agent and/or odorant may be present in the coating composition at a concentration of 1 pg/ml-1 ng/ml, 1 ng/ml-1 mg/ml, 1 mg/ml-1000 mg/ml. A therapeutic agent and/or odorant may be present in the coating composition at a concentration of 0.01-1000 mg/ml, 0.1-100 mg/ml, or 0.4-40 mg/ml. The amount or concentration of a therapeutic agent and/or odorant in a polymerized coating can be determined by any means known in the art. For example, the amount or concentration of a therapeutic and/or odorant in a polymerized coating can be determined by extraction of the therapeutic agent and/or odorant from the polymerized coating and analysis of the extracted therapeutic agent. Analysis can be by any means known in the art, for example, by chromatography, e.g., high performance liquid chromatography.

The therapeutic agent and/or odorant may be added to the coating compositions by any means known in the art. For example, the therapeutic agent and/or odorants may be added to an invention composition upon formulation. The therapeutic agent and/or odorants may be added to the composition prior to polymerizing the composition. In some cases, the therapeutic agent and/or odorants are added directly to the invention composition upon formulation. In some cases, the therapeutic agent and/or odorant is added to a solution that is used in the preparation of an invention composition. The therapeutic agent and/or odorant can be added to an invention composition comprising a solvent, prior to evaporation of the solvent. In some cases, the therapeutic agent and/or odorant is added after polymerization of an invention composition. For example, the coating composition can be polymerized onto a surface, providing a surface coated with an invention coating. The coated surface can then be contacted with a solution comprising the therapeutic agent or odorant to be added. The solution can comprise the drug dissolved in a solvent. The solvent can be any of the solvents described herein. In some embodiments, the solvent comprises methanol. The method of contacting can comprise, e.g., immersion of the surface in the solution. The coated surface can be in contact with the solution for a duration of time. The duration of time can be of any length sufficient to allow the therapeutic agent to diffuse from the solution into the coated surface at any point of contact with the solution. The duration of time can be, e.g., 0.5 hours or more, 1 hour or more, 2 hours or more, 3 hours or more, 4 hours or more, 5 hours or more, 6 hours or more, 7 hours or more, 8 hours or more, 9 hours or more, 10 hours or more, 11 hours or more, 12 hours or more, 13 hours or more, 14 hours or more, 15 hours or more, 16 hours or more, 17 hours or more, 18 hours or more, 19 hours or more, 20 hours or more, 21 hours or more, 22 hours or more, 23 hours or more, 24 hours or more, 2 days or more, 4 days or more, 7 days (1 week) or more, 2 weeks or more. The duration of time can be 0.5-6 hours, 4-10 hours, 8-16 hours, 12-24 hours, 0.5-2 days, 1-7 days, or 1-2 weeks. After diffusion of the therapeutic agent into the polymerized coating, the coated surface can be removed from contact with the solution. The coated surface can then be rinsed. Rinsing of the coated surface can remove excess therapeutic agent and/or any other unwanted materials from the polymerized coating.

The formulation of the coating and the amount of therapeutic agent(s) can be manipulated to result in a controlled elution of the therapeutic agent(s). For example, the concentration of the monomer units of the composition and the amount of solvent in the composition upon formulation can be adjusted to result in the formation of a porous polymer matrix comprising the therapeutic agent(s). The density and/or dimensions of the pores in the porous matrix can affect the elution kinetics of the coating composition. The density and/or dimensions of the pores in the porous matrix can be adjusted to manipulate the density and/or dimensions of the pores in the porous matrix, thereby manipulating the elution kinetics of the coating.

The coatings of the invention can be configured to elute the therapeutic agent(s) for a period of time. The coatings can elute the therapeutic agent for 1 day, 2 days, 3 days, 4 days, 5 days, 6 days, 7 days (1 week), 1.5 weeks, 2 weeks, 2.5 weeks, 3 weeks, 3.5 weeks, 4 weeks, 1 month, 1.5 months, 2 months, 2.5 months, 3 months, 3.5 months, 4 months, 4.5 months, 5 months, 5.5 months, 6 months, 7 months, 8 months 9 months, 10 months, 11 months, 12 months (1 year), 1.5 years, 2 years, or more than 2 years. The coated product can elute the one or more therapeutic agents for an unlimited duration. The coated product can elute the one or more therapeutic agents for as long as the product remains implanted in the subject.

The polymerized coatings of the invention can be configured to elute the therapeutic agent at a controlled rate. The elution of the one or more therapeutic agents can follow zero order kinetics, e.g., the coating can release the one or more therapeutic agents at a steady rate until the agent(s) are depleted. The elution kinetics of the polymerized coatings can be determined by any means known in the art. The elution kinetics can be determine by, e.g., HPLC sampling.

In some embodiments, a product is coated with a plurality of layers of an invention coating. The number of layers and formulation of the layers can be adjusted to control the amount and elution rate of the therapeutic agent(s). In some cases, the coating composition for each layer can be prepared formulated to result in each layer comprising a porous structure that is substantially similar. In other cases, the coating composition for each layer can be prepared in distinct methods such that each layer has a distinct porous structure. For example, envisioned is a product comprising a first layer of coating with pores of a certain size and density, such that a large amount of the therapeutic agent is encapsulated in the pores of the layer. The product can further comprise a second layer of coating having pores of a different size and density such as to limit the rate of elution to a desired rate.

In some cases, the invention coatings can be configured so as not to elute the therapeutic agents. For example, the invention coatings may be configured as to retain the therapeutic agent. In some cases, the invention coating are configured to retain the therapeutic agent by comprising a cross-linking agent. In some cases, the therapeutic agent may be cross-linked to the invention coating.

Coated Products

In practicing the invention, the coating compositions can be applied to a variety of products. The product to be coated can be a man-made product, e.g., a product that is not naturally occurring.

A product to be coated can comprise a surface, e.g., a substrate, for coating. The substrate can comprise a material. The material can be, for example, metallic, polymeric, plastics, elastomers, ceramic, carbon, glass materials, or silicon materials. Suitable metals include stainless steel, nickel, titanium, tantalum, platinum, cobalt, chromium, nitinol and combinations or alloys of these materials. Suitable polymeric materials may include thermoset or thermoplastic polymers, including polyurethane, polypropylene, polyethylene and other suitable polymers. Suitable polymers include natural polymers for example cellulose. Specific materials include polyvinylchlorides (PVC), polycarbonates (PC), polyurethanes (PU), polypropylenes (PP), polyethylenes (PE), silicones, polyesters, polymethylmethacrylate (PMMA), hydroxyethylmethacrylate, N-vinyl pyrrolidones, fluorinated polymers (e.g., fluoropolymers). Fluoropolymers can be prepared from a monomer. For example the fluoropolymer can be prepared from: Ethylene (E), Propylene (P), Vinyl fluoride (VF1), Vinylidene fluoride (VDF or VF2), Tetrafluoroethylene (TFE), Hexafluoropropylene (HFP), Perfluoropropylvinylether (PPVE), Perfluoromethylvinylether (PMVE), or Chlorotrifluoroethylene (CTFE). The fluoropolymer can be, for example, PVF (polyvinylfluoride), PVDF (polyvinylidene fluoride), PTFE (polytetrafluoroethylene), including expanded PTFE (ePTFE), highly porous ePTFE, low-porosity ePTFE, compressed PTFE, PCTFE (polychlorotrifluoroethylene), PFA (perfluoroalkoxy polymer), FEP (fluorinated ethylene-propylene), ETFE (polyethylenetetrafluoroethylene), ECTFE (polyethylenechlorotrifluoroethylene), FFPM/FFKM (Perfluorinated Elastomer [Perfluoroelastomer]), FPM/FKM (Fluorocarbon [Chlorotrifluoroethylenevinylidene fluoride]), PFPE (Perfluoropolyether), or PFSA (Perfluorosulfonic acid). The fluoropolymer can be prepared through chemical-, thermal-, and/or mechanical-induced consolidation of polymerized resin particles. The fluoropolymer can be treated to improve its properties associated with the invention. For example improve adhesion strength can in some embodiments be achieved by incorporating use of high-energy vis/UV radiation treatment to create a reactive ePTFE surface.

Suitable plastics include, e.g., polystyrenes (PS), polyethylenes, polyethylene terephthalate, polypropylene (PP), polyvinyl chloride (PVC), nylon, rubber (synthetic and natural), Polyvinylidene chloride (PVDC), Low-density polyethylene (LDPE), Polyamides (PA), Acrylonitrile butadiene styrene (ABS), Polyethylene/Acrylonitrile Butadiene Styrene (PE/ABS), Polycarbonate (PC) Polycarbonate/Acrylonitrile Butadiene Styrene (PC/ABS) and Polyurethanes (PU).

Exemplary glass materials include, e.g., silicate glass such as fused silica glass, soda-lime-silica glass, sodium borosilicate glass, lead-oxide glass, aluminosilicate glass, oxide glass, recycled glass, network glass, colloidal glass, glass-ceramics or polymer glass (for example acrylic glass, polycarbonate, polyethylene terephthalate).

The product to be coated may also comprise materials such as, e.g., carbon-fiber reinforced plastics or glasses containing filler materials.

The material of the substrate can be porous. Porosity can be measured as a fraction or percentage of the empty space/total volume of the substrate. The porous material can be highly porous. A highly porous material can have a porosity of over 50%, 55%, 60%, 65%, 70%, 75%, 80%, 85%, 90%, 95%, 99%, or over 99%. A highly porous material (e.g., a highly porous ePTFE material) can have a porosity of 50-60%, 60-75%, 75-90%, 90-99%, or over 99%. The porous material can have a low porosity. The low-porosity material (such as, e.g., a low-porosity ePTFE material), can have a porosity of less than 50%, less than 45%, less than 40%, less than 35%, less than 30%, less than 25%, less than 20%, less than 15%, less than 10%, less than 5%, less than 2.5%, less than 1%, less than 0.5%, less than 0.1%, or substantially 0%. The low-porosity material (e.g., a low-porosity ePTFE) can have a porosity of 0-5%, 2-10%, 5-20%, 15-30%, 20-40%, or 30-50%. The pores of the porous material, whether highly porous or of low porosity, can have an average diameter. The average diameter of the pores can be 0.001, 0.005, 0.01, 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 3, 4, 5, 6, 7, 8, 9, 10, 15, 20, 25, 30, 40, 50, 60, 70, 80, 90, or 100 microns. The average diameter of the pores can be 0.001-0.01 microns, 0.01-0.1 microns, 0.1-0.3 microns, 0.3-1 microns, 2-10 microns, 3-22 microns, 10-50 microns, or 40-100 microns.

The product to be coated may also comprise materials such as paper, paper laminates, non-woven materials, non-woven laminates, and other similar substrates. The coatings of the invention can be applied to, e.g., surgical gowns and drapes, examining table paper, hospital bed pads, hospital bed inserts and sheeting, gloves, routine fixtures, and surgical masks.

The product to be coated can be a medical device. The term 'medical device' is used herein to encompass all medical apparatuses which are used in the treatment of, and come in contact with, a human or animal body or its blood, fluids or other biological membranes. Exemplary medical devices include, e.g., a mesh, a suture mesh, a wound dressing, a stent, a skin patch, a bandage, a prosthetic, a suture anchor, a screw, a pin, a cannula, a tack, a rod, an angioplastic plug, a plate, a clip, a ring, a needle, a tube, an orthopedic implant, a guided tissue matrix, an aortic aneurysm graft device, a shunt (e.g., an atrioventricular shunt), a catheter, a valve (e.g., a heart valve), a pump, an artificial joint, hemodialysis catheter, a marker, a bone-fracture healing device, a bone replacement device, a joint replacement device, a tissue regeneration device, a tumor targeting and destruction device, a periodontal device, a hernia repair device, a hemodialysis graft, an indwelling arterial catheter, an indwelling venous catheter, a pacemaker casing, a pacemaker lead, a pacemaker, a patent foramen ovale septal closure device, a vascular stent, a tracheal stent, an esophageal stent, a urethral stent, a rectal stent, a stent graft, a synthetic vascular graft, a vascular aneurysm occluder, a vascular clip, a vascular prosthetic filter, a vascular sheath, a drug delivery port and a venous valve.

Coated Stent

Coatings of the invention can be applied to a stent. Accordingly, the invention provides a stent coated with one or more layers of the compositions described herein. The term "stent" herein means any device which when placed into contact with a site in the wall of a lumen to be treated, will also place fibrin at the lumen wall and retain it at the lumen wall. This can include especially devices delivered percutaneously to treat coronary artery occlusions and to seal dissections or aneurysms of splenic, carotid, iliac and popliteal vessels. Any stent known in the art can be coated with an invention coating. For example, the stent can be as described in U.S. Pat. No. 4,886,062, hereby incorporated by reference. The stent can be a self-expanding stent. The self-expanding stent can be made of a resilient polymeric material such as that disclosed in published international patent application WO 91/12779, hereby incorporated by reference.

Coated Soft Tissue Mesh

In some embodiments, the coated product is a coated soft tissue mesh. The term "mesh", as used herein, can refer to a semi-permeable structure. Soft tissue meshes generally comprise a flexible material. The material of the soft tissue mesh can be any of the materials described herein. Exemplary materials include ePTFE, polypropylene, expanded polypropylene. A soft tissue mesh can comprise pores. The pores may be closely spaced. In some cases, the soft tissue mesh comprises filaments. The filaments may be of a synthetic material. In some cases, the soft tissue mesh has a first surface and a second surface. The first and second surfaces may be on opposite sides of the mesh, e.g., the ventral and dorsal side. In some cases, one surface is a smooth surface and the opposite surface is a textured surface. Exemplary meshes include, e.g., Gore® Dual Mesh® (Gore Medical), VENTRIO™ Hernia Patch (Davol), Ventralex™ Hernia Patch (Bard), PROCEED™ Ventral Patch (Ethicon). Such meshes can be used in a variety of medical applications, for example, meshes can be used as surgical implant for hernia repair, e.g., a hernia patch. A mesh, according to the present embodiments, can be formed by weaving, interlacing, interweaving, knotting, knitting, winding, braiding and/or entangling the elongated elements so they come in contact to form a network of nodes or hubs separated by holes or openings. Alternatively, a mesh can be formed by punching, drilling, cutting or otherwise forming the holes in a sheet of the mesh material.

A three-dimensional mesh is formed by either forming a sheet, staking several mesh sheets or by bending a mesh sheet into a hollow or tubular object. Exemplary meshes include, without limitation, gauze, a screen, a strainer, a filter, a stent, a wound-dressing and the likes. For example, a stent, such as the widely used medical device in angioplasty, bronchoscopy, colonoscopy, esophagogastroduodenoscopy and to treat restenosis and other cardiovascular conditions, is an example of a three-dimensional mesh of struts which are interconnected in a orderly fashion and shaped into a cylindrical tube. Hence, according to embodiments of the present invention, the mesh can take the form or be shaped so as to have a form such as a sheet, a tube, a sphere, a box and a cylinder.

The coating of an entire pre-fabricated core structure such as a mesh as presented herein, is realized in the nodes, junctions, intercrossing, hubs or otherwise the points of contact where individual sub-structural elements meet (referred to herein and encompassed under the phrase "intercrossing junctions"). For example, in the case where the core structure is a mesh, when a mesh is woven from pre-coated fibers, two intercrossing fibrous core elements do not come in contact with each other when they form a junction since they are separated with at least two coat layers sheathing each thereof. In the coated pre-fabricated meshes presented herein, the core elements touch each other via direct physical contact and the entire junction which is formed therebetween is coated as a whole without having a coat material separating the elements. In practice, this feature expresses itself mainly in the way the mesh experiences the gradual degradation of the coat layer. In a mesh which is weaved from pre-coated fibers, the mesh may loosen and even come apart when the coating layers thins and dwindles as a result of its capacity to biodegrade, or in other cases the polymeric coat may swell and cause the element to distance each other causing a deformation of the core structure to some extent, while the coated pre-fabricated meshes do not experience any change due to the erosion or swelling of the coat and thus the mesh or other similar core structure maintains its structural integrity and stability throughout the process of degradation or swelling of the coat.

Meshes that can be employed as surgical implants include, for example, polypropylene mesh (PPM) which has been used extensively in hernia repair to provide the necessary strength and support for tissue growth for the repair of abdominal defects in hernia. Other examples include expanded polytetraflouroethylene (ePTFE), highly porous ePTFE, low porosity ePTFE, compressed PTFE, sepramesh biosurgical composite, compressed sepramesh biosurgical composit, polyethylene terephthalate (PET), compressed PET, and titanium.

Implants may have a dorsal surface and a ventral surface. The dorsal surface is the portion of the implant which faces outward away from a fascia defect and the ventral surface is the portion which faces inward towards the defect. Prior to implantation, some of the implants described herein may, in an unstressed state, assume a flat or planar shape, or may assume a concave and/or convex shape on one or more surfaces. Implants may comprise surface modifications.

The hernia patch can comprise a material as described in U.S. Pat. No. 6,780,497, which is hereby incorporated by reference. For example, the hernia patch can comprise an ePTFE composition, wherein the ePTFE composition comprises a macro-roughened surface characterized by ridges and valleys, and further wherein the ePTFE composition is microporous or macroporous. The ePTFE composition can be as described in U.S. Pat. No. 7,666,496, hereby incorporated by reference.

The mesh can be in the form of a sponge. The sponge can either be made from a synthetic material, such as polyvinyl alcohol, or from a bioabsorbable material, such as collagen, gelatin, keratin, laminin, fibrin, or fibronectin. Examples include HELISTAT®, HELITENE®, and VITAGUARD® (Integra Life Sciences, Plainsboro, N.J.), and ULTRAFOAM® (Davol, Inc., Cranston, R.I.). In certain instances, the sponge can be a bioabsorbable sponge that is only temporarily present in the body of a subject. Meshes and sponges described herein may also be referred to by other terms, such as for example, a pad or a gauze, etc.

A mesh may be sufficiently flexible to allow a surgeon to manipulate the implant to conform to the surgical site and/or ease delivery during a laparoscopic procedure. However, in some circumstances, a stiffer arrangement that limits compression and/or expansion of the mesh may be preferred. In certain embodiments, a mesh is be collapsible, such as by folding, rolling, or otherwise, into a slender configuration, so that it may be delivered through a narrow lumen of a laparascopic device. Flexibility of the implant is influenced by many factors, including, the materials from which the implant is made, treatments applied to the implant or any other features of the body of the implant. A mesh may either include a single mesh or be formed from two or more mesh segments that are joined or overlap.

Various methods of hernia repair and implants suitable for use in hernia repair are known and described, for example, in U.S. Pat. Nos. 5,176,692; 5,569,273; 6,800,0825,824,082; 6,166,286; 5,290,217; and 5,356,432. Generally, such devices include (a) a mesh-like member configured for repairing a fascia defect in a subject; and optionally (b) a means for securing the mesh-like member to the site of the fascia.

Coated Catheter

In some embodiments, the coated product is a coated catheter. Catheters can be configured for, e.g., intravenous, arterial, peritoneal, pleural, intrathecal, subdural, urological, synovial, gynecological, percutaneous, gastrointestinal, abscess drains, and subcutaneous applications. Catheters can be used for short-term, intermediate, and long-term applications. Types of catheters include standard IV, peripherally inserted central catheters (PICC)/midline, central venous catheters (CVC), angiographic catheters, urinary catheters, guide catheters, feeding tubes, endoscopy catheters, Foley catheters, drainage catheters, external catheter (e.g., condom catheter), and needles.

The catheter can be a venous catheter. Central venous catheters and peripheral venous catheters are contemplated in the invention. The central venous catheter can be a non-tunneled catheter or a tunneled catheter. Non-tunneled catheters can be fixed in place at the site of insertion, with the catheter and attachments protruding directly. Commonly used non-tunneled catheters include Quinton catheters. Tunneled catheters can be passed under the skin from the insertion site to a separate exit site, where the catheter and its attachments emerge from underneath the skin. The exit site can be typically located in the chest, making the access ports less visible than if they were to directly protrude from the neck. Passing the catheter under the skin helps to prevent infection and provides stability. Commonly used tunneled catheters include Hickman catheters and Groshong catheters. The peripheral venous catheter can be configured for insertion into a peripheral vein.

The catheter can be a dialysis catheter. The dialysis catheter can be configured to exchange blood to and from a hemodialysis machine to a subject, e.g., a human patient. The dialysis catheter can be a tunneled dialysis catheter or a non-tunneled dialysis catheter.

In some embodiments, in addition to a coating of the invention, the coated catheter can further comprise a hydrophilic surface coating. When immersed in water the hydrophilic surface coating can swell to a smooth, slippery film. The smooth, slippery film can render the catheter safer and more comfortable to insert.

The invention coatings may be applied to an electronic device. The electronic device may or may not be a hand-held device. Accordingly, the invention also provides an electronic device coated with a coating composition described herein. Electronic devices may be electronic equipment intended for everyday use (consumer electronic). An electronic device may be a device for entertainment, communications and office productivity. Examples of consumer electronic that may be coated with the protective coating of the invention include personal computers, telephones, MP3 players, audio equipment, televisions, calculators, GPS automotive electronics, digital sphygmomanometers, digital glucose meters, digital cameras and players and recorders using video media such as DVDs, VCRs or camcorders. More specifically the protective coatings of the present invention may be used on mobile devises for example on mobile phones including touchscreen phones, iPods, iPads and other tablet personal computers. The protective coating form the present invention may also be used on electronic devices intended for community use, for examples personal computers, key boards, mouse or televisions in public libraries.

In further embodiments, the invention coatings may be used on other house hold objects that exhibit microorganism and/or viral contamination. Non-limiting examples of such objects include buttons, handles, knobs, steering controls, toilets, etc. In further embodiments, the protective coatings of the present disclosure may be used on items that are both communal in nature and are intended for physical contact for example in public toilets and payphones.

Coating Methods

The products or product surface as mentioned herein can be coated by any means known in the art. For example, the products can be coated by dipping, spraying, flowing, casting, wicking, pouring, pumping, brushing, or wiping with the coating compositions. Spray coating can involve atomizing the coating composition into a mist and directing the mist to the product (e.g., aerosol spraying). Spray coating may afford more rapid vaporization of one or more solvents present in the coating composition upon formulation, allowing the coating composition to harden upon the product surface upon spraying.

The product or product surface can be pre-wetted with a solvent prior to application of a coating composition. The solvent can be the same solvent that is used in the coating composition. In some cases, the product is not pre-wetted with a solvent prior to application of a coating composition.

Other coating techniques, however, are also deemed to be within the scope of this invention. For example, common coating techniques that are contemplated include reverse roll, rod, and gravure coating methods. Roll coating methods further include kiss coating, single roll coating, and double roll coating, among others.

The coating composition can be applied to the product or product surface in one or more layers. The one or more layers can have a thickness. The thickness can be a substantially uniform thickness or may be a non-uniform thickness. The thickness of the coating layer can be 0.01-10 microns. The thickness can be, e.g., 0.01, 0.02, 0.03, 0.04, 0.05, 0.06, 0.07, 0.08, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6. 5.7, 5.8, 5.9, 6, 6.1, 6.2, 6.3, 6.4, 6.5, 6.6. 6.7, 6.8, 6.9, 7, 7.1, 7.2, 7.3, 7.4, 7.5, 7.7, 7.8, 7.9, 8, 8.1, 8.2, 8.3, 8.4, 8.5, 8.8, 8.7, 8.8, 8.9, 9, 9.1, 9.2, 9.3, 9.4, 9.5, 9.6, 9.7, 9.8, 9.9, or 10 microns. The thickness can be, e.g., 0.01-0.1 micron, 0.05-0.5 microns, 0.1-1 microns, 0.5-2 microns, 1-3 microns, 2-6 microns, or 5-10 microns.

Solvent(s) can be evaporated from the coating composition after the coating composition is applied to a product or product surface. Solvent can be evaporated from the coating composition prior to polymerization of the coating onto the product or product surface. In some cases, at least 10%, 25%, 30%, 35%, 40%, 45%, 50%, 55%, 60%, 65%, 70%, 75%, 80%, 90%, 95%, 96%, 97%, 98%, 99%, or 100% of the solvent is evaporated from the coating composition prior to polymerization on the product or product surface. For example, 10-40%, 20-50%, 30-70%, 40-90%, or 70-100% of the solvent may be evaporated from the coating composition prior to polymerization on the product of the product surface. Evaporation of the solvent can be achieved by any means known in the art, including exposing the coated surface to air currents, heating, vacuum (e.g., reduced pressure), or by an evaporation device.

Polymerization of the Coating Compositions

The coating compositions may be polymerized before or after it is applied to a product surface. In some embodiments, the coating is polymerized after it is applied to the product surface. The coating may be polymerized by a curing process. The curing process may involve curing by light, curing by heat, air curing, or any other curing process known to a skilled artisan. Curing by light may be by LED light, by UV light, by visible light, by laser light (e.g., helium, xenon, etc.), or by fluorescent light. The curing may, in some instances, occur in a chamber. The chamber may be a degassing chamber. An exemplary curing chamber is depicted in FIG. 1.

In some embodiments, curing can be achieved using a commercially available curing apparatus. Exemplary curing apparatuses include microwave powered UV curing apparatuses (e.g., Heraeus Noblelight Fusion UV curing system, spot UV curing apparatuses (e.g., the Rocket LP apparatus (www.americanultraviolet.com)), the CureJet™ apparatus/light source. An exemplary curing apparatus is described in WO2012012865, hereby incorporated by reference.

The curing apparatus can comprise a light source. The light source can be a visible light source, can be a laser light source, can be a UV light source, can be a fluorescent light source, can be an LED light source, or any combination thereof. The light source can produce a light having an energy output. The energy output of the light can be less than or equal to 20 W/cm$^2$. The energy output can be, e.g., 20 W/cm$^2$, 19 W/cm$^2$, 18 W/cm$^2$, 17 W/cm$^2$, 16 W/cm$^2$, 15 W/cm$^2$, 14 W/cm$^2$, 13 W/cm$^2$, 12 W/cm$^2$, 11 W/cm$^2$, 10 W/cm$^2$, 9 W/cm$^2$, 8 W/cm$^2$, 7 W/cm$^2$, 6 W/cm$^2$, 5 W/cm$^2$, 4 W/cm$^2$, 3 W/cm$^2$, 2 W/cm$^2$, or 1 W/cm$^2$. The energy output can be 1-20 W/cm$^2$, 3-15 W/cm$^2$, or 7-10 W/cm$^2$.

The curing apparatus may comprise a light filter. The light filter may be placed in the light path from the light source to the location of the polymerization reaction. The light filter can be used to control the spectral parameters of the light reaching the polymerization site. The light filter can prevent light of certain wavelengths from reaching the polymerization site. The light filter can, for example, prevent light having wavelengths of 400 nm or above from reaching the polymerization site. The light filter can allow light of specific wavelengths to reach the polymerization site. The light filter can, for example, be configured to allow light of wavelengths between 280-480 nm to reach the polymerization site. The light filter can, for example, be configured to allow light of wavelengths between 280-405 nm to reach the polymerization site. The light filter can, for example, be configured to allow light of wavelengths greater than 325 nm to reach the polymerization site.

The curing apparatus can comprise a site for placing a product to be coated. The location of the site can be adjusted to provide a distance between the light source and the location where polymerization occurs (e.g., polymerization site). The distance can be, e.g., 0.5, 1, 2, 3, 4, 5, 6, 7, 8, 9, 10 cm. The distance can be 0.5-3 cm, 2-5 cm, 4-7 cm, or 6-10 cm.

The distance between the polymerization site (taken to be the same as the base of the Rocket LP apparatus) and light source, the spectral properties of the light reaching the polymerization site, and intensity of the source can be adjusted to deliver a range of activation energies to the polymerization site. For example, since intensity and distance are both related to energy delivered per area, an increase in distance can be compensated for by increasing the intensity and vice versa.

The coated products can be further processed after polymerization of the coating. For example, the coated products can be sterilized after polymerization of the coating. Sterilization can be achieved by any means known in the art. Any appropriate sterilization process can be used, including the conventional physical or chemical methods or treatment with ionizing radiation such as, for example, gamma or beta rays. The coated products can be placed in a sterile packaging.

The invention also provides kits. A kit may include a coated product in a sterile packaging, and instructions for use. In some cases, a kit may include one or more components for preparing a coating composition of the invention, and instructions for preparing the coating composition using the one or more components.

The invention also provides systems for preparing a coated product of the invention. Systems may comprise a coating composition, a product to be coated, and a curing apparatus. Exemplary compositions, exemplary products, and exemplary curing apparatuses are described herein.

EXAMPLES

Example 1

Compounds

Synthesis of Formula XI:

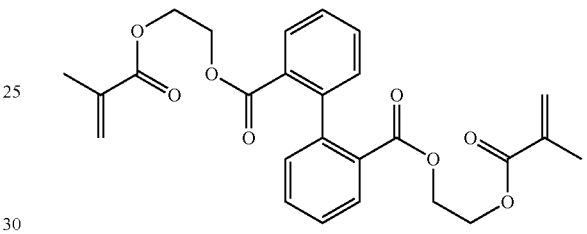

The following were mixed together and then heated at 50° C. for 6 hours: 150 g Diphenic acid, 506 g Thionyl Chloride, 0.5 g Dimethylformamide. The mixture was allowed to cool at room temperature for 12 hours. The thionyl chloride was then roto-evaporated at reduced pressure at 80° C. When thionyl chloride had fully evaporated, the liquid was allowed to reach room temperature. 275 g of methylene chloride was added and all solids were dissolved. Then, the following was added slowly: 120 g Methylene chloride, 118 g pyridine (in the 120 g methylene chloride), 186 g 2-hydroxyethyl methacrylate. Temperature was held at 45° C. for 3 hours with continual stirring, until the solution became thick with salts. Salts were filtered off and then rinsed with 180 g methylene chloride three times. All of the washes from the salts were combined with the first filtrate into a separatory funnel. 1 L of 0.1M HCl in water was then admixed with the mixture. When the emulsion separated, the oil layer (on bottom) was collected. The oil layer was dried with magnesium sulfate. The magnesium sulfate was filtered off and the solution was brought to half its volume by roto-evaporation at reduced pressure and 25° C. The reduced volume solution (about 300 mL) was then loaded onto a column with 200 g of basic alumina on top of 700 g of silica and eluted with MeCl$_2$. A spectrophotometer was used to collect the first major product to come off the column. The solution from the column was evaporated to remove the MeCl2, resulting in the compound of Formula XI.

Example 2

Testing of Various Coating Compositions

Various formulations for preparing a polymerized coating comprising a homopolymer of a compound of Formula XI were tested. The effects of monomer weight percentage in casting solution, allowing acetone to evaporate prior to curing, and increasing the power of the energy source were studied. For the purposes of the experiments described below, "DMC" refers to a compound of Formula XI:

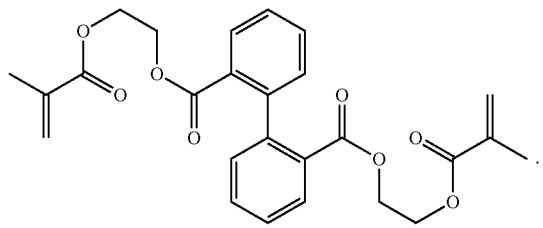 [SMILES: C=C(C)C(=O)OCCOC(=O)c1ccccc1-c1ccccc1C(=O)OCCOC(=O)C(=C)C]

(XI)

Methods

Four DMC coatings were polymerized on 6 mm straight Impra vascular grafts. DMC coatings consisted of DMC monomer in acetone at either 10% or 20% by wt/wt. The photoinitiator Irgacure 2959 (BASF; Ludwigshafen, Germany) was added to the monomer casting solution at 1 wt % of the monomer solution used. 1 cm terminal ends of grafts were coated using ¼" glass rods and 100 µl of monomer/solvent/initiator casting solution. Curing was conducted immediately after casting or after approximately two minutes of passing air across the graft, still positioned onto the glass rod. Curing was conducted with the Lesco Rocket positioned 2" from the support base providing 7.2 W of energy as measured by a The Power Wizard 250 (Synrad; Mulkilteo, Wash.) positioned on base and centered in emitted energy. Graft and glass rod assemble were spun along the length axis in the center of the emitted energy for two minutes at the distance denoted in the table below. A short pause in exposure was performed after one minute of curing to allow cooling of the graft.

The casting and curing conditions tested in this experiment are described in Table 1:

TABLE 1

Casting and Curing conditions

| Specimen name | DMC (wt %) | Distance form waveguide (in) | Acetone evaporated |
|---|---|---|---|
| A | 10 | 1.5 | No |
| B | 10 | 1.5 | Yes |
| C | 20 | 1.5 | No |
| D | 20 | 0.75 | No |

The "acetone evaporated" column refers to whether acetone was evaporated from the coating formulation prior to curing.

SEM Microscopy

Figure 2:
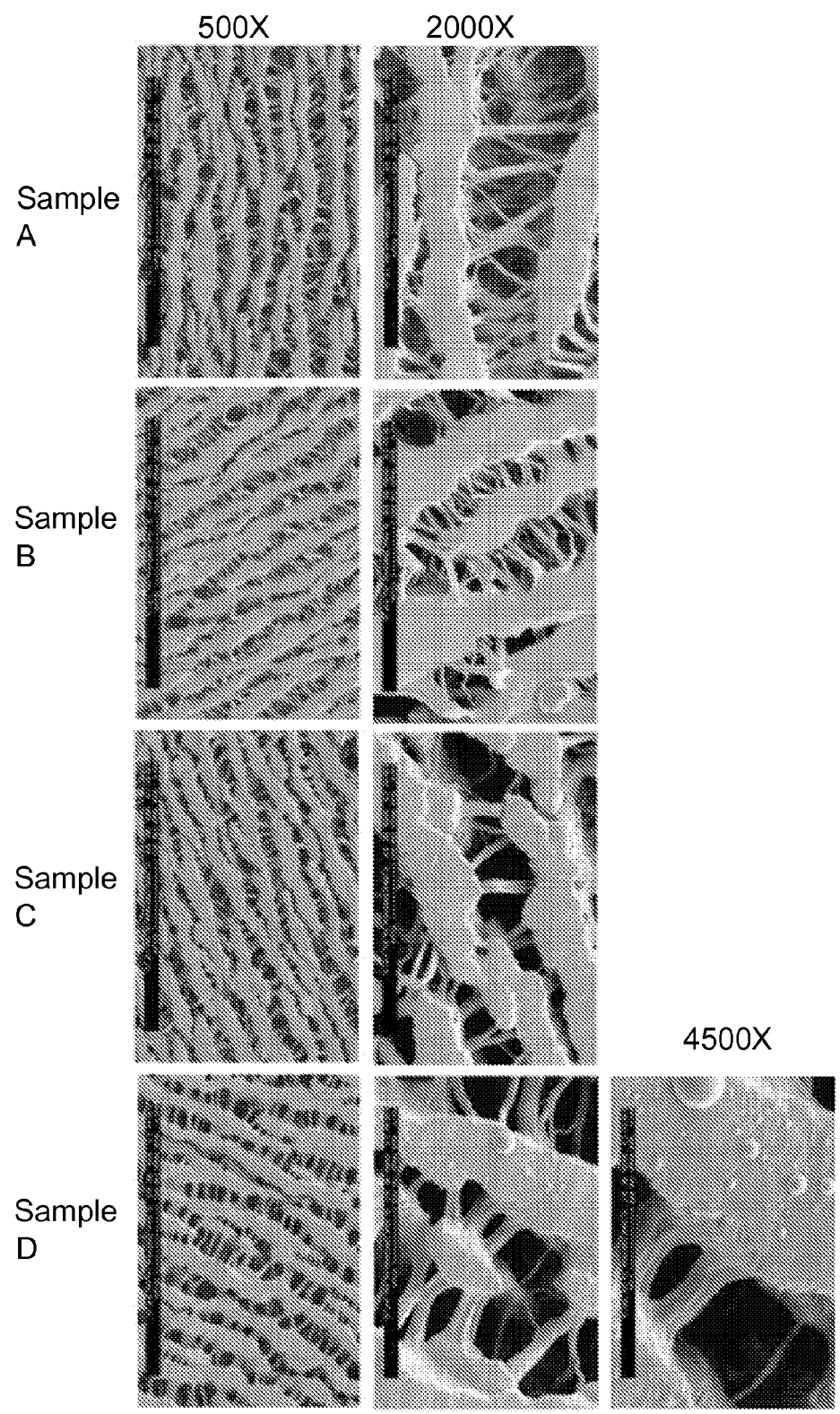
FIG. 2 depicts SEM micrographs of ePTFE mesh inner lumens coated with a polymerized coating of the invention.
Figure 3:
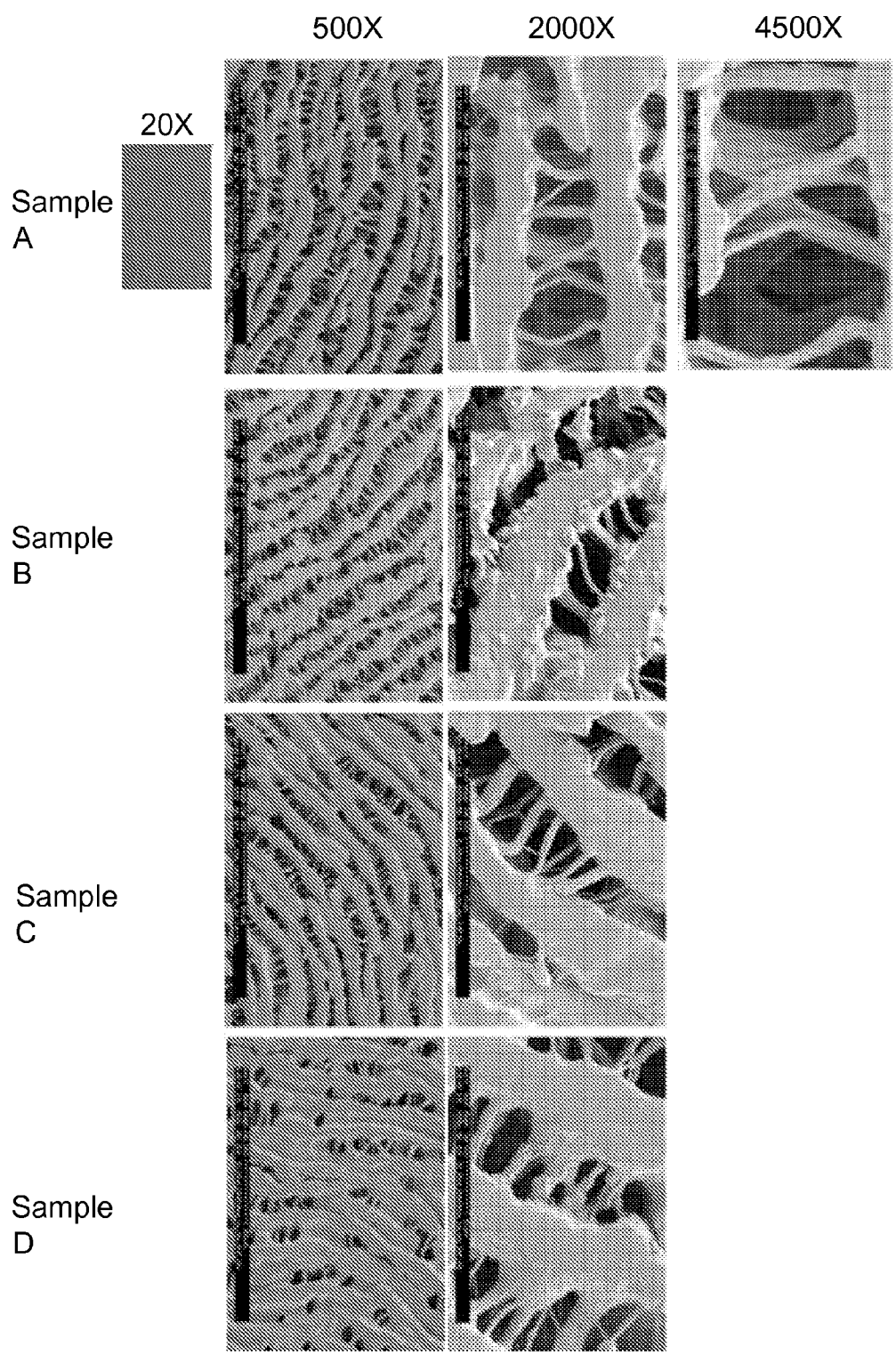
FIG. 3 depicts SEM micrographs of ePTFE mesh outer lumens coated with a polymerized coating of the invention.

Specimens were sectioned lengthwise, and sections samples were mounted onto SEM stubs using double sided carbon adhesive tabs (Electron Microscopy Sciences (EMS); Hatfield, Pa.; P/N 77825-12). A thin border of graphite was run along the perimeter of at least one side of each sample using graphite colloidal adhesive (EMS; P/N 12691-30). Two sections were cut from each sample and mounted on a common stub with different lumen sides facing up for imaging. A 13 nm thick gold/palladium (80:20) layer was applied to mounted samples using a sputter coater (EMS; Model EMS550X) and controller (EMS; Model EMS150X). Imaging was performed using an SEM microscope (FEI; Hillsboro, Oreg.; Model XL30). 20×, 500×, 2,000×, and 4,500×OM images were acquired at approximately 7-10 mm working distance using an excitation beam of 5 kV and secondary electron beam detection. SEM photomicrographs of the inner lumen of the grafts are shown in FIG. 2. SEM photomicrographs of the outer lumen of the grafts are shown in FIG. 3.

The results indicate that the DMC formulations generally provide an even and uniform layer of coating on the graft inner and outer surfaces. Curing at the 0.75" distance resulted in excessive heating that lead to the formation of bubbles and shrinking of the grafts. This shrinking is either the result of improved degree of polymerization, as methacrylates are known to shrink upon curing, or ePTFE loosing mechanical strength at the higher temperature and allowing deformation due to methacrylate cure shrinking force that was not seen previously. It is also possible that both of these occurrences led to the shrunken condition. The shrinking was visible to the naked eye in terms of length of the coated graft region, initially coated 1 cm but was only 0.7 cm after cure.

Example 3

Testing of Compositions Comprising a DMC Compound

Pure DMC homopolymers or copolymers comprising a 1:1 weight ratio of a DMC compound:methyl methacrylate were created and tested. Monomer solutions at either 10 wt % or 20 wt % DMC were polymerized using acetone, dichloromethane, toluene, xylenes, tetrahydrofuran, and ethyl acetate as solvents, independently. Irgacure-2959® (2-hydroxy-1-[4-(2-hydroxyethoxy)phenyl]-2-methyl-1-propanone) was used as the photoinitiator. Irgacure-2959® was added to the monomer/solvent systems at 0.1, 0.5, and 1 wt %. A Rocket LP energy source was used to activate the photoinitiator.

Table 2 below depicts selected DMC formulations, substrates for coating, and curing conditions tested in this experiment.

TABLE 2

Summary of DMC formulations

| | Formulation ID | | | | |
|---|---|---|---|---|---|
| | 1 | 2 | 3 | 4 | 5 |
| DMC wt % | 20 | 20 | 10 | 10 | 5 |
| MMA wt % | 0 | 0 | 0 | 0 | 5 |
| Solvent | acetone | acetone | dichloromethane | acetone | acetone |
| Irgacure wt % | 0.1 | 0.5 | 1 | 1 | 1 |
| Rocket Filter (nm) | 280-480 | 280-480 | 280-400 | 280-400 | 280-400 |
| Output Energy (W)[1] | NA | NA | 7.1 | 7.2 | 10.4 |
| Distance (cm) | 2 | 2 | 5.1 | 5.1 | 5.1 |
| Cure Time (sec) | 60 | 25 | 120 | 120 | 2 × 60 sec with cooling between |
| Substrate | glass slide | glass slide | roughened polypropylene mesh | 6 mm Bard vascular graft | treated perforated polypropylene sheet |

Polypropylene mesh specimens were coated with the DMC formulations according to the following steps: (1) 1×2 cm specimens of polypropylene mesh were cut with scissors from a larger sample supplied by the manufacturer. (2) Specimens were rolled back in forth between fingertips several times to roughen the surfaces of the monofilaments. (3) Using forceps, the strips were lowered into assigned test solutions for dip coating. (4) Strips were removed from the uncured monomer/solvent/initiator solutions using forceps. (5) Holding monomer cast strips with forceps, excess solution was removed with a few quick shakes. The strip remained suspended in air the entire time during this process, only contacting forceps. (6) Polymerization was conducted with strips placed on Rocket LP base using the parameters described in Table 1 under Formulation 3. (7) Qualitative assessment of coating integrity before and after flexing specimens was conducted by eye and at 40× using an inverted microscope. Note: In addition to the dichloromethane of Formulation 3, other test formulations looked at acetone, tetrahydrofuran (THF), and toluene solvent systems. Additionally, dip coating the as received mesh (without roughening) was also attempted with all solvents. Complete mesh surfaces were coated with DMC polymer using Formulation 3 (Table 1), but some flaws persisted in the coating. Necking and agglomeration were seen at monofilament junctures and within knots, respectively. Bending of the polymer-coated polypropylene meshes resulted in cracking of the coating, delamination from the monofilament surfaces, and particulate release.

ePTFE vascular graft specimens were coated with DMC formulations and assessed by SEM microscopy according to following steps: (1) Vascular grafts specimens were cut to 1.5 cm lengths from a 6 mm Impra graft and mounted onto a ⅛" glass rod with 1 cm sitting proud of the glass rod tip. (2) 100 µL of various DMC formulations monomer/solvent/initiator solution was passively wicked into the terminal 1 cm of the graft. (3) The graft was held at approximately a 450 angle with the Rocket LP energy source path and positioned pointing upward, using the glass rod as an extender jig, allowing exposure to both inner and outer graft surfaces. (4) The glass rod was slowly spun along its length, rotating the graft during the entire cure such than an even exposure was delivered to both the inner and outer lumen surfaces. (5) Coated grafts were sectioned, positioned on stubs using double-sided conductive tape and colloidal graphite, and coated with 13 nm of Au/Pd. Specimens for both inner and outer lumen imaging were produced. (6) SEM imaging was conducted at 20×, 500×, 2,000×, and 4,500×. SEM settings include the following: secondary electron mode, ~10 mm working distance, and 5 kV beam acceleration voltage.

Perforated polypropylene sheet specimens were coated with the DMC formulations according to the following steps: (1) Section of perforated polypropylene sheet were cut from bulk material and treated through either surface roughening with sandpaper or surface roughening with sandpaper followed by flame treatment. Flame treatment was performed through quickly running the flame of a cigarette lighter over the surface of the polypropylene once. (2) Sections were dip coated in DMC formulations using forceps. (3) Curing was conducted on one side only by laying the coated section on the Rocket LP base directly under the incident wave. (4) Cured surfaces were transferred face down onto glass slides and imaged at 40× with digital image acquisition. Note: In addition to the two surface treatments used with Formulation 5, others were attempted on the perforated polypropylene using identical cure parameters for the Rocket LP. As received surfaces were dip coated and cured with the monomer/solvent/initiator solution of Formulation 5 and pure DMC polymer formulations were attempted. Flame treatment and the combination of sandpaper roughening followed by flame treatment were also utilized to evaluate pure DMC systems as well.

Figure 4:
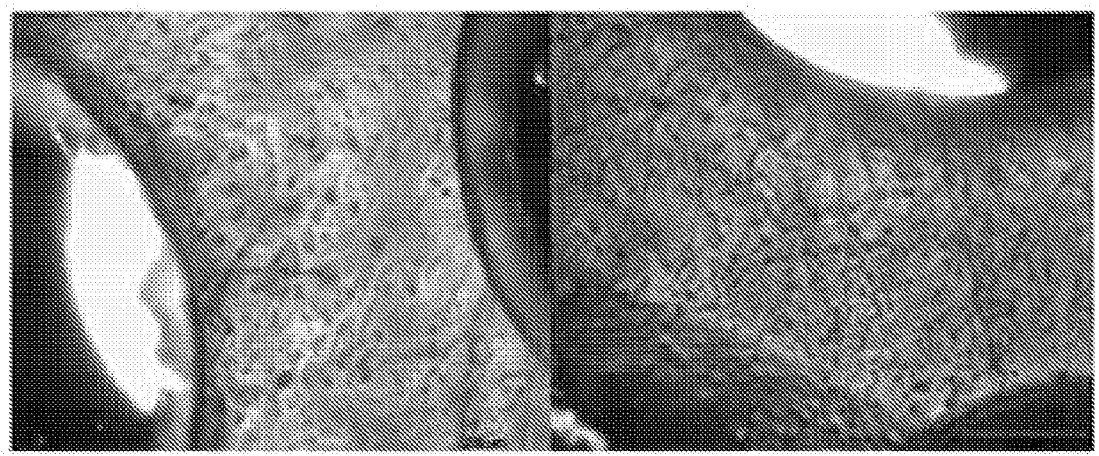
FIG. 4 depicts photomicrographs of perforated polypropylene sheets coated with a polymerized coating of the invention.

FIG. 4 depicts light microscopy images of the coatings obtained with Formulation 5 (as described in Table 2) on the surface treated polypropylene sheet. It was noted that combination of sandpaper roughening followed by flame treatment resulted in surface that was less scratch resistant than sandpaper roughening alone, but the appearance of the resulting coatings were indistinguishable. Note: The following trends were noted in the other experimental coating formulations mentioned above: coating as received surfaces with pure DMC and comonomer blend of Formulation 5 resulted in uneven coatings which easily flaked off, coating as received surfaces with the comonomer blend of Formulation 5 improved coverage while flaking persisted, flame treated only and sandpaper roughened followed by flame treatment with pure DMC monomer systems resulted in coating which easily flaked off, and sandpaper roughened followed by flame treatment with pure DMC monomer systems improved coverage and adhesion but to a much lower degree than the comonomer blends.

Example 4

Protection of Therapeutic Agents from Light Degradation by DMC Coatings

Figure 5A:
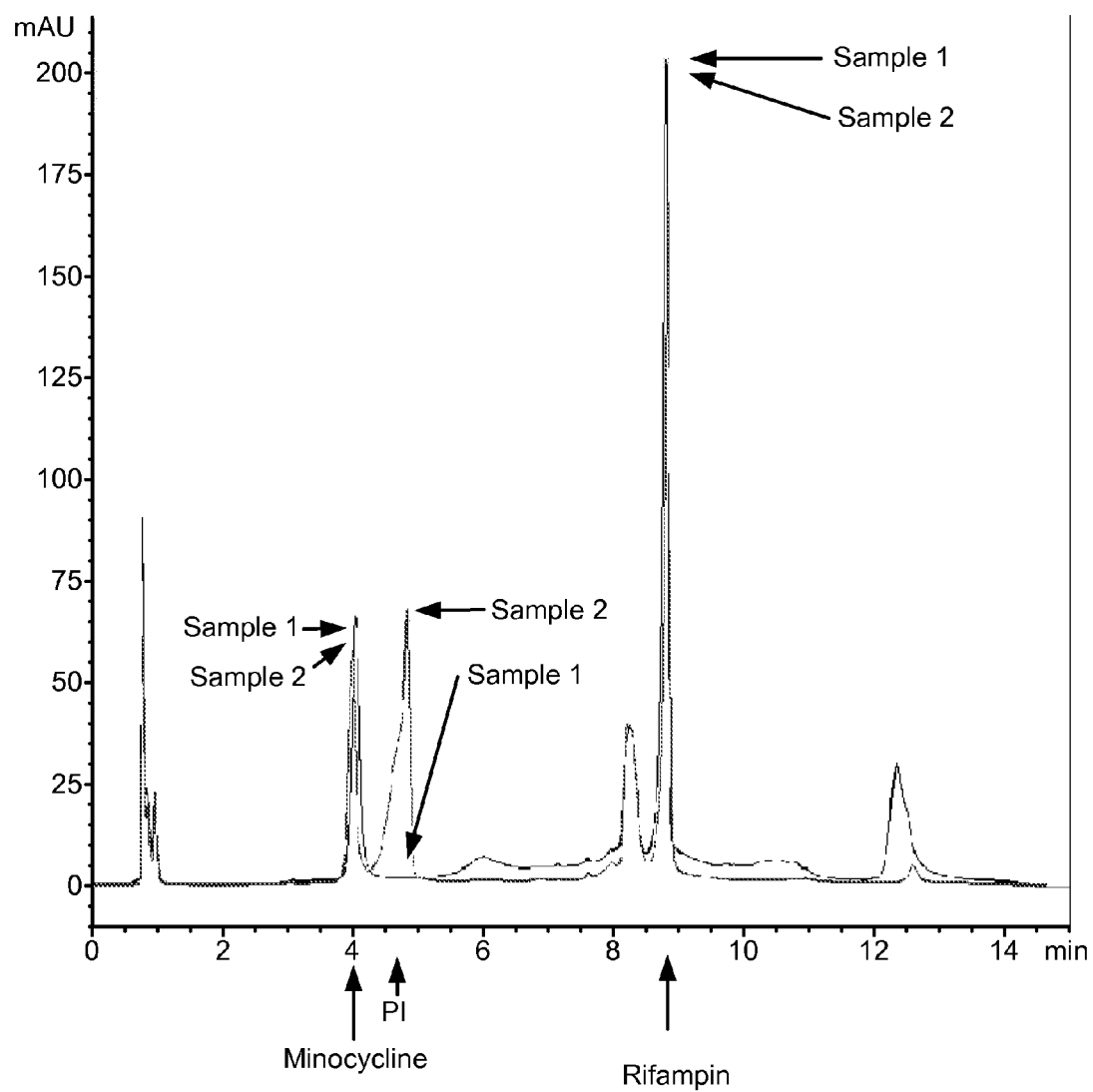
FIGS. 5A-D depict HPLC chromatograms demonstrating that coating formulations of the invention protect therapeutic agents from degradation by light.
Figure 5B:
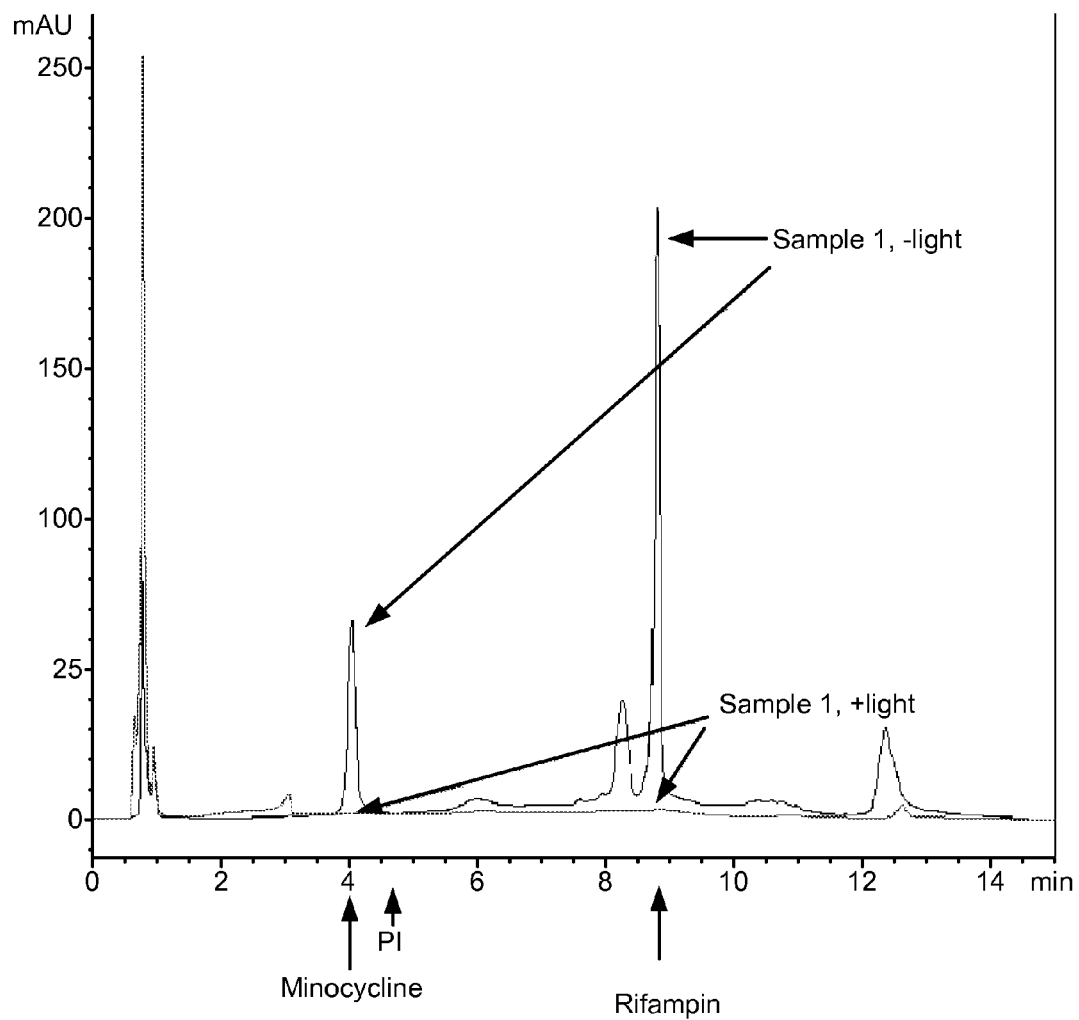
Figure 5C:
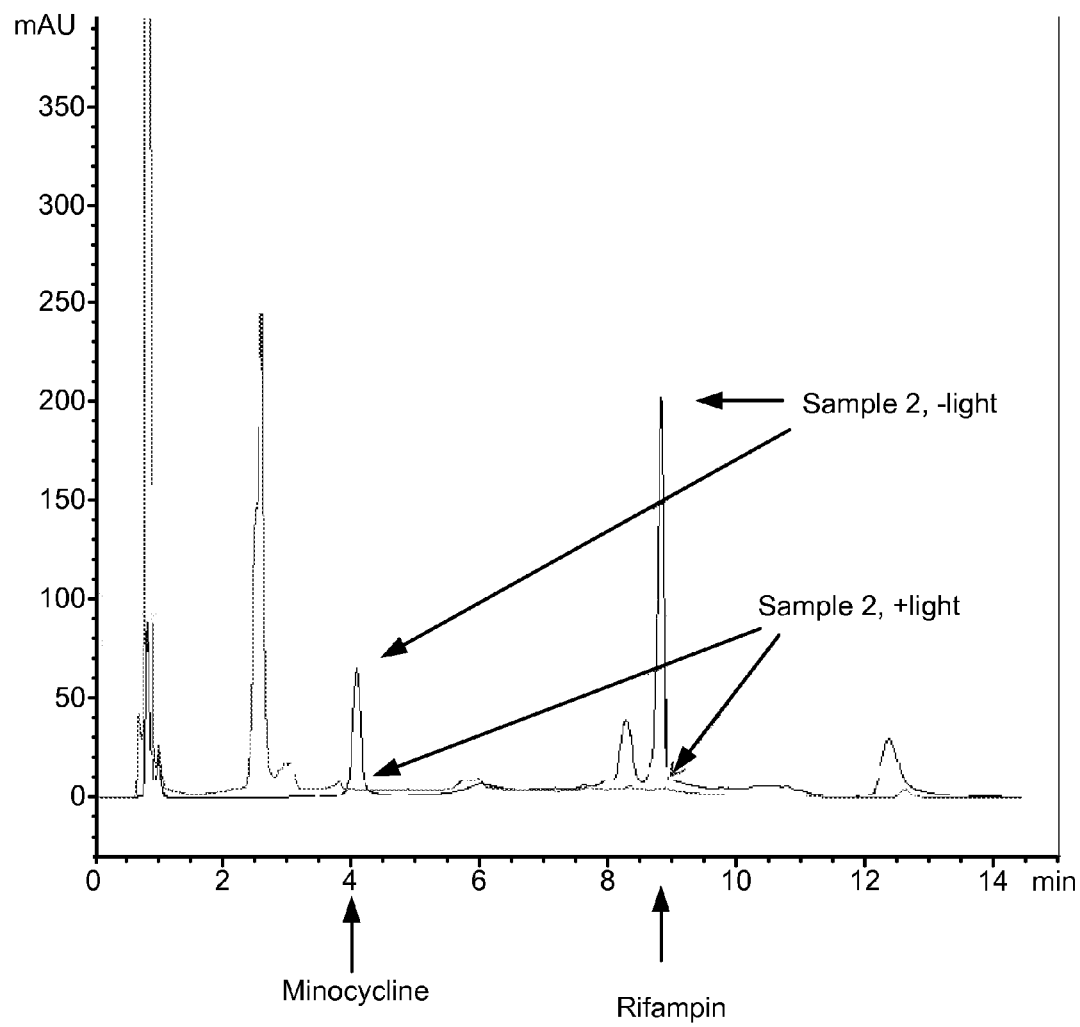
Figure 5D:
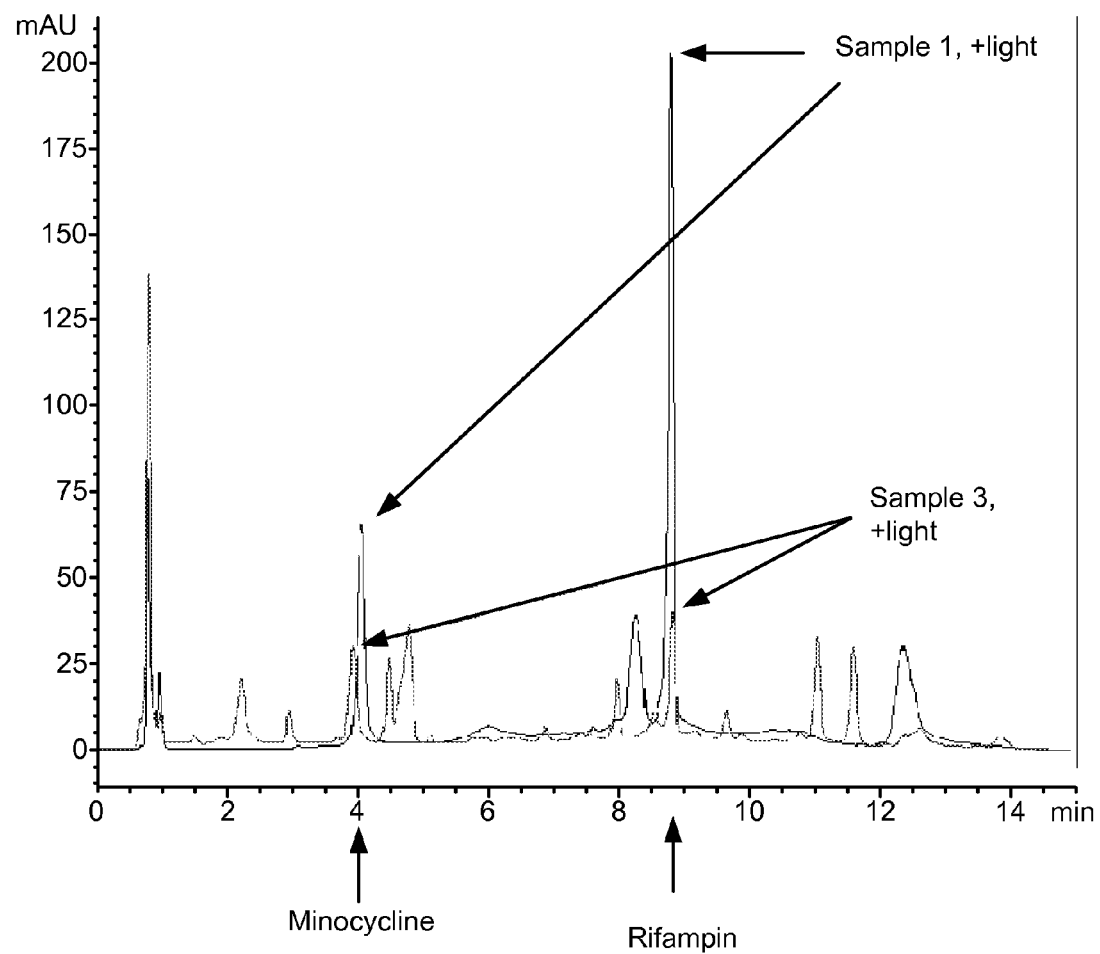

HPLC tests were performed to assess the effects of various components of the coating composition on drug stability. HPLC analysis was run on the starting 50 µg/ml drug solution as a control. HPLC parameters were as follows: Channel A=>35 mM sodium phosphate pH=7.5 w/1 v % TEA; Channel B=>acetonitrile; 0-50% B 0-10 min, 50% B 10-13 min, 50-0% B 13-15 min, 0% B 6 min post time; 20 µl injections; 1 ml/min; 30° C.; 335 nm. Note: 280 nm is now known to be a much improved wavelength for solutions with equal amounts of minocycline and rifampin. Samples tested included: (1) Solvent+Drug; (2) Solvent+Photoinitiator (PI)+Drug; and (3) Solvent+Monomer Component+PI+Drug. The Solvent+Drug samples (Sample 1) were prepared as follows: 1 ml/ml rifampin in acetone and 1 mg/ml minocycline in 9:1 v/v water:acetone were used to make a single 50 µg/ml solution of each drug in acetone. The Solvent+PI+Drug (Sample 2) samples were prepared as follows: 1% wt/wt IrgaCure® 2959 was added to the 50 µg/ml drug solution solutions and cured according to the parameters described for Formulation 5 in Table 2. The Solvent+Monomer Component+PI+Drug+Drug (Sample 3) were prepared as follows: ~3 ml Formulation 5 (Table 2) inspired solution with exception of using the 50 µg/ml drug solution and 20 wt % comonomer as the solvent was created and exposed to cure parameters detailed for Formulation 5 (Table 2) followed by HPLC analysis upon blending 1:1 with methanol, to terminate polymerization reaction/free-radicals. Note: polymerization of small volumes of Formulation 5 results in evaporation of the acetone solvent, thereby concentrating the monomers. This does not happen at the 3 ml large volume, justifying use of a higher comonomer wt %. Results are depicted in FIGS. 5A-5D. FIG. 5A depicts HPLC chromatograms from the Sample 1 (dark gray line) and Sample 2 (light gray line) without exposure to light. FIG. 5A demonstrates that the drugs were stable when not exposed to light (as shown by the near complete overlap of the Solvent+drug chromatogram and Solvent+Photoinitiator+Drug chromatogram). FIG. 5B depicts chromatograms from the Sample 1 samples without light exposure and with light exposure. Panel B demonstrates that in solvent alone, the drugs were degraded by light exposure, as demonstrated by the absence of drug peaks in the + light chromatogram. FIG. 5C depicts chromatograms from Sample 2 without light exposure and with light exposure. FIG. 5C demonstrates that the presence of the photoinitiator did not protect the drugs from light-induced degradation, as demonstrated by the absence of drug peaks in the + light chromatogram. FIG. 5D depicts chromatograms from Sample 1 and Sample 3 after exposure to light. FIG. 5D demonstrates that Formulation 5 protected the drugs from complete light-induced degradation.

Example 5

Coating of ePTFE Hernia Patch ePTFE hernia patches were coated as follows: Specimens having 1 cm diameter were cut from a ePTFE hernia mesh having a thickness of one mm (Gore Medical DualMesh® P/N 1DLMC02). Specimens were then coated with either one or three layers according to the following process: (a) 55 µl of 0.1 wt % Irgacure 2959 (BASF; P/N 55047962) in 10 wt % DMC acetone solution was applied and wicked into the DualMesh from the roughened/corduroy side of the material; (b) Monomer solution coated specimens were held upright with using clamps with minimal contact of specimen surface area and transferred to a nitrogen flushed curing chamber; (c) Acetone and absorbed oxygen were allowed to evaporate and degas, respectively, under nitrogen for 20 minutes prior to turning on lamps; (d) Polymerization of the DMC monomer on the DualMesh was conducted through UV-C ultraviolet energy exposure using three PL9W lamps under nitrogen for 2 hours (see FIG. 1); (e) a portion of the specimens were recoated and exposed to the degassing and curing process two additional times for a total three applications of the polymer coating. After polymerization (or 1 or 3 coatings), coatings were loaded with drugs (minocycline and rifampin). Coated meshes were soaked for ~17 hours at 4° C. in a solution comprising 10 mg/ml minocycline hydrochloride (Hovione; P/N NY01) and 10 mg/ml rifampin (Fisher; P/N BP2679-1) in methanol. Specimens were then removed from drug solution and dried in air. Following air-drying, specimens were rinsed in either methanol) or water. For the methanol rinse, specimens were suspended using forceps and agitated by hand in two consecutive 15 ml methanol rinses for 15 seconds, then allowed to air dry. For the water rinse, specimens were transferred to 10 ml of deionized water in conical tubes and aggressively vortexed for 2 minutes. Specimens were then allowed to air dry. The above steps resulting in the following four conditions: (a) 1 coat—water rinse; (b) 3 coats—water rinse; (c) 1 coat—methanol rinse; and (d) 3 coat—methanol rinse. Specimens retained flexibility after coating and coatings did not flake when the samples were bent.
HPLC Analysis Dried specimens were individually extracted in 1 ml of methanol at 4° C. for 64 or 76 hours. 20 µl of each extract were run on HPLC to assess the effects of rinse method and number of coating cycles on drug loading of the coatings. HPLC conditions were as follows: 30° C.; 250×3 mm C-18 with 5 µm packing; 280 nm absorbance; Channel A—35 mM Na2HPO4 with 1 vol % triethylamine, pH=8.1 w/phosphoric acid; Channel B—acetonitrile/Running parameters at 1 ml/min: (i) 0-10 minutes—gradient 0-50 vol % Channel B; (ii) 10-20 minutes—50 vol % Channel B; (iii) 20-25 minutes—20-0 vol % Channel B.

Figure 6:
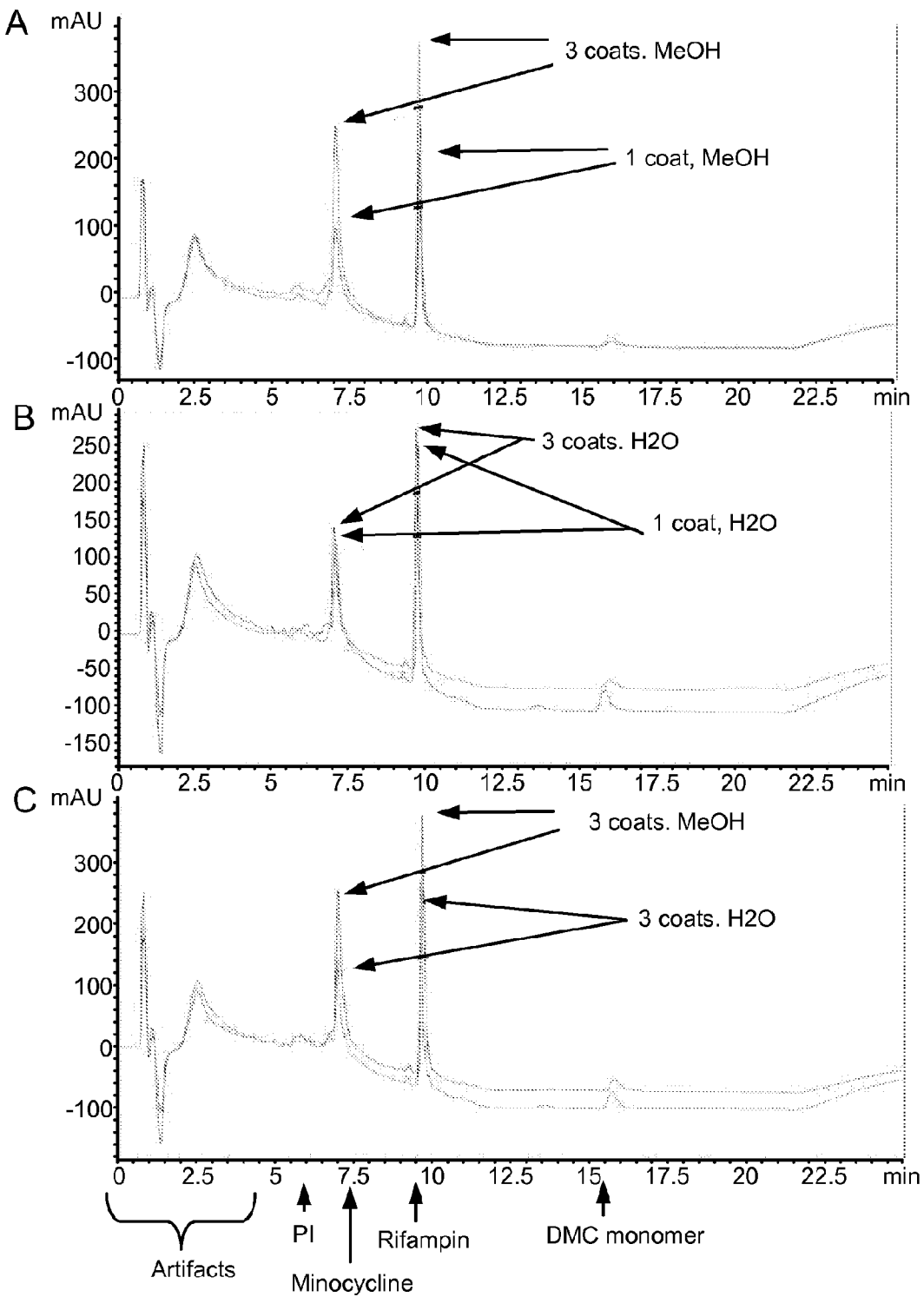
FIGS. 6A-6C depict HPLC chromatograms of coatings prepared according to methods of the invention.

FIG. 6 depicts HPLC results from methanol-rinsed samples coated with one or three layers of coating (A), water-rinsed samples coated with one or three layers of coating (B), three-layer coated samples rinsed with water or methanol (C). Results indicate that therapeutic agents can be loaded into the invention polymerized coatings after polymerization. Minocycline and rifampin were both absorbed into the methacrylate coating matrix. For the methanol-rinsed samples, three coating cycles increased the amount of drugs absorbed from approximately 0.2 mg/cm$^2$ for 1 coating to approximately 0.4 mg/cm$^2$ (FIG. 6A). For the water-rinsed samples, there was little benefit for drug uptake as a result of increased coating cycles (FIG. 6B). The methanol rinsing procedure allowed for retention of the largest amount of absorbed drugs (FIG. 6C). In addition to allowing for drug absorption, loading of therapeutic agents into the polymerized coating after polymerization has occurred confers additional benefits. For example, such methods allow polymerization to commence without the inhibitory effect of the presence of the therapeutic agents. Without wishing to be bound by theory, inhibition of polymerization can result from proton abstraction between radicals generated by the activated polymerization initiator and the amine groups of some therapeutic agents. Furthermore, such methods obviate the possibility of degradation of the therapeutic agents during the polymerization process. Furthermore, it is contemplated that the drug adsorption step and the rinsing steps also wash out the majority of any leftover monomer and initiator.

Example 6

Extraction/Drug Recovery Studies

HPLC studies were conducted to determine the impact of the coating formulations and curing process on drug recovery and degree of polymerization. DMC formulations were prepared as described herein, using 1% vs. 0.1% photoinitiator. One cm terminal ends of vascular grafts, sitting proud of a ¼" glass rod, were coated with 100 uL of 10 wt % DMC in acetone at the two photoinitiator called out above and with minocycline hydrochloride and rifampin loaded in the coating solution such that 0.2 mg/cm$^2$ of each drug was loaded. Acetone evaporation and oxygen degassing were performed for 10 minutes under nitrogen in the curing chamber (FIG. 1). Polymerization was then induced through UV-C exposure for 30 minutes under nitrogen. 24-72 hour extractions of the coated products were conducted in methanol.

Figure 7:
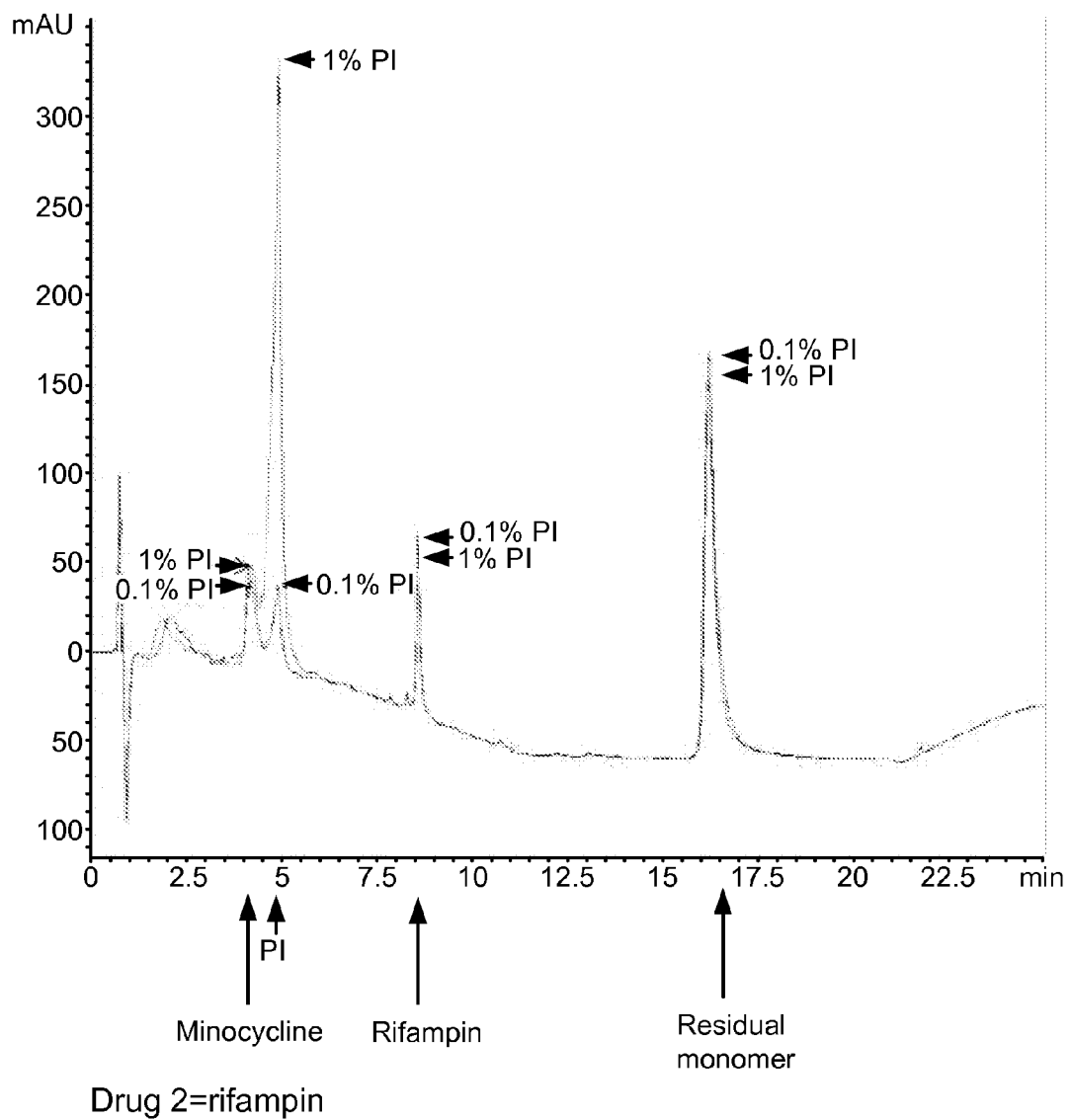
FIG. 7 depicts HPLC chromatograms of coatings prepared according to methods of the invention.

FIG. 7 depicts chromatographs of the DMC formulation with 1% photoinitiator and of the DMC formulation with 0.1% photoinitiator. Note that the monomer peaks are equivalent among the 0.1% photoinitiator and 1% photoinitiator chromatograms, indicating that similar degrees of polymerization can be achieved with a minimal (0.1%) concentration of photoinitiator. In addition, the Drug 1 and Drug 2 peaks are equivalent among the 0.1% and 1% photoinitiator chromatograms.

Example 7

Antimicrobial Studies

Zone of inhibition studies using the Kirby-Bauer Assay were conducted on grafts coated with the coating 1 or coating 2 formulations. Coating 1 is composed of 100 μl of polymer resulting from a mix of isomers as described in Formula I, an NTG-GMA salt, and an acetone/ethanol/water blend. Coating 2 is described in Example 6 utilizing 1 wt % photoinitiator, a 10 minute degas, and 10 minute UV-C cure. Drug loadings were held constant 0.2 mg/cm$^2$ for each drug used (minocycline hydrochloride alone or, both, minocycline hydrochloride and rifampin. as described in Examples 1 and 2. Zone of inhibition studies were conducted according to the following steps: (1) Grow S. aureus UAMS-1 (staph) and E. coli ATCC 25922 overnight in TSB at 37° C. (2) Dilute overnight growth of S. aureus 1:10 in TSB and add 100 μl to TSB agar, dilute E. coli 1:50 in TSB and add 100 μl to TSB agar. (this provides ~1×106 CFU per plate). (3) Place experimental samples on the agar plates containing the lawn of bacteria and incubate for 24 hours at 37° C. (4) Photograph the plates after the 24 hour incubation and measure the diameters of the zone of inhibition. If the zone of inhibition is oblong then the shortest distance was measured. Experimental groups tested are depicted in Table 3.

TABLE 3

Groups tested.

| Sample ID | Description |
| --- | --- |
| A | Coating 1 |
| AM | Coating 1 loaded with minocycline hydrochloride |
| AMR | Coating 1 loaded with minocycline hydrochloride and rifampin |
| D | Coating 2 |
| DM | Coating 2 loaded with minocycline hydrochloride |
| DMR | Coating 2 loaded with minocycline hydrochloride and rifampin |

Figure 8:
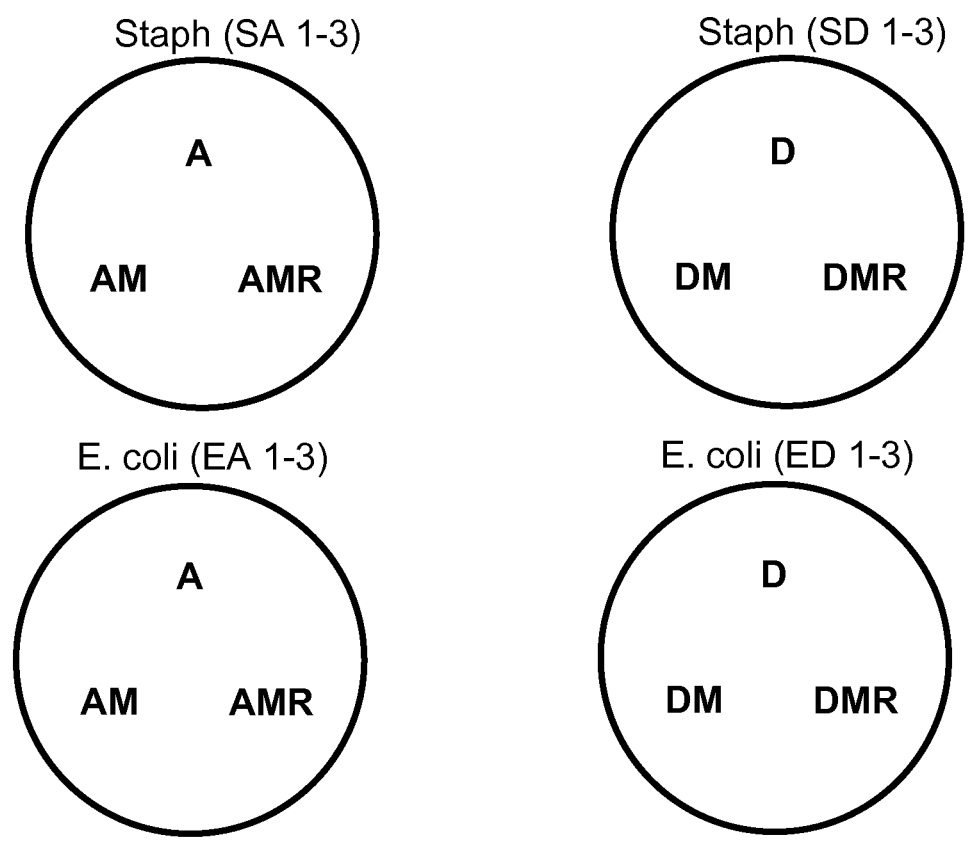
FIG. 8 depicts plate layouts for zone of inhibition experiments testing coated vascular grafts using the Kirby-Bauer assay.
Figure 9:
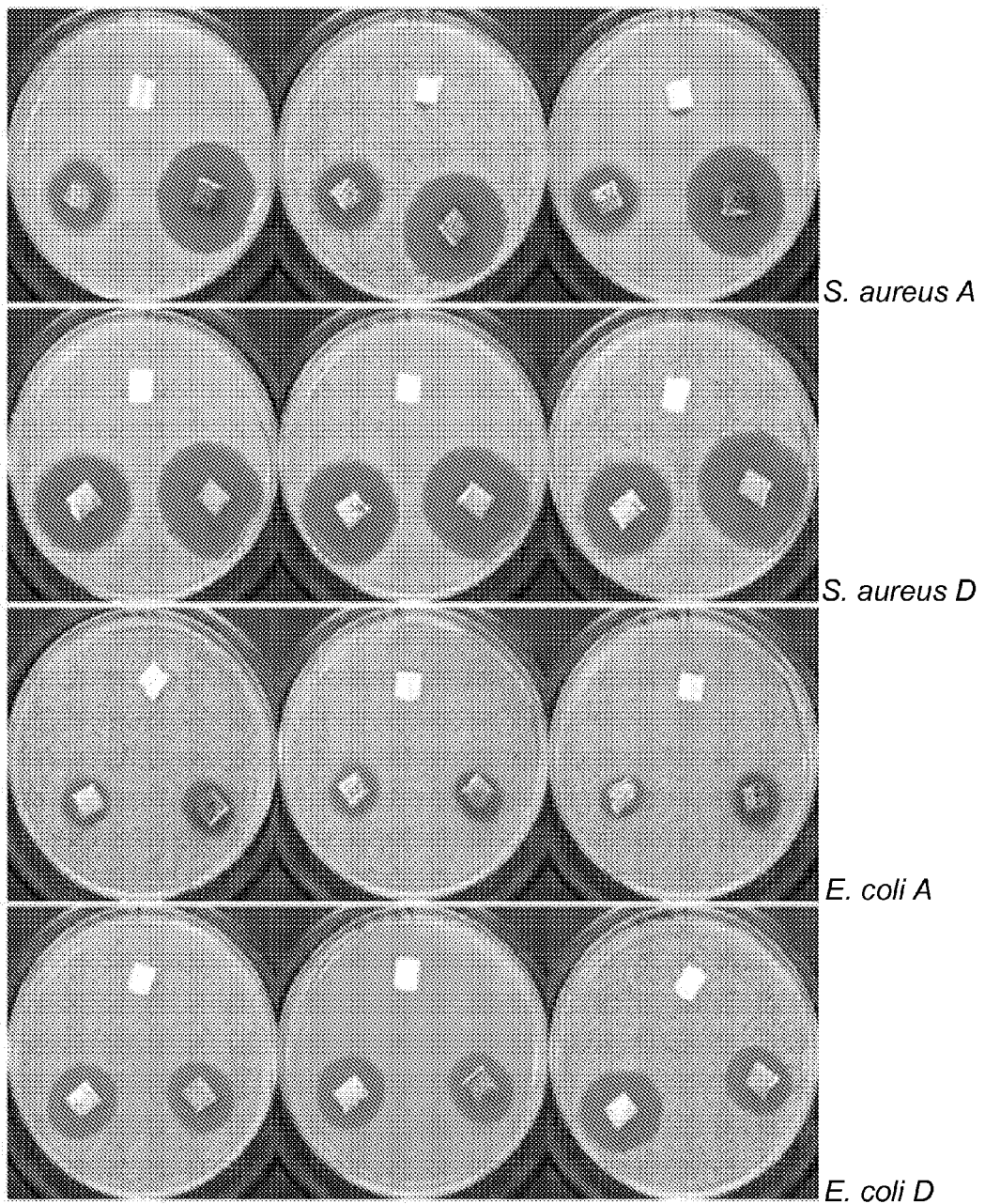
FIG. 9 depicts photographs of plates from the Kirby-Bauer experiment.

A total of 12 plates were run for Zone of Inhibition testing. Six plates were inoculated with S. aureus, and the remaining half were inoculated with E. coli. Each plate contained three samples which covered all variations of a single coating (1 or 2). The layout of the plates are shown in FIG. 8 as indicated by the first letter of the sample IDs. Photographs of the plates after the 24 hour incubation are depicted in FIG. 9. The measured diameters obtained from the zone of inhibition study are depicted in Table 4:

TABLE 4

Zone of inhibition study results

| Sample | Diameter of ZOI (mean ± SD) |
| --- | --- |
| S. aureus A | 0, 0, 1 (0.3 ± 0.5) |
| S. aureus AM | 20, 21, 22 (21 ± 1.0) |
| S. aureus AMR | 33, 32, 33 (32.6 ± 0.5) |
| S. aureus D | 0, 0, 0 (0) |
| S. aureus DM | 30, 31, 29 (30 ± 1.0) |
| S. aureus DMR | 35, 34, 35 (34.6 ± 0.5) |
| E. coli A | 0, 0, 0 (0) |
| E. coli AM | 15, 17, 13 (15 ± 2.0) |
| E. coli AMR | 16, 16, 16 (16 ± 0) |
| E. coli D | 0, 0, 0 (0) |
| E. coli DM | 21, 22, 24 (22.3 ± 1.5) |
| E. coli DMR | 21, 20, 20 (20.3 ± 0.5) |

Figure 10:
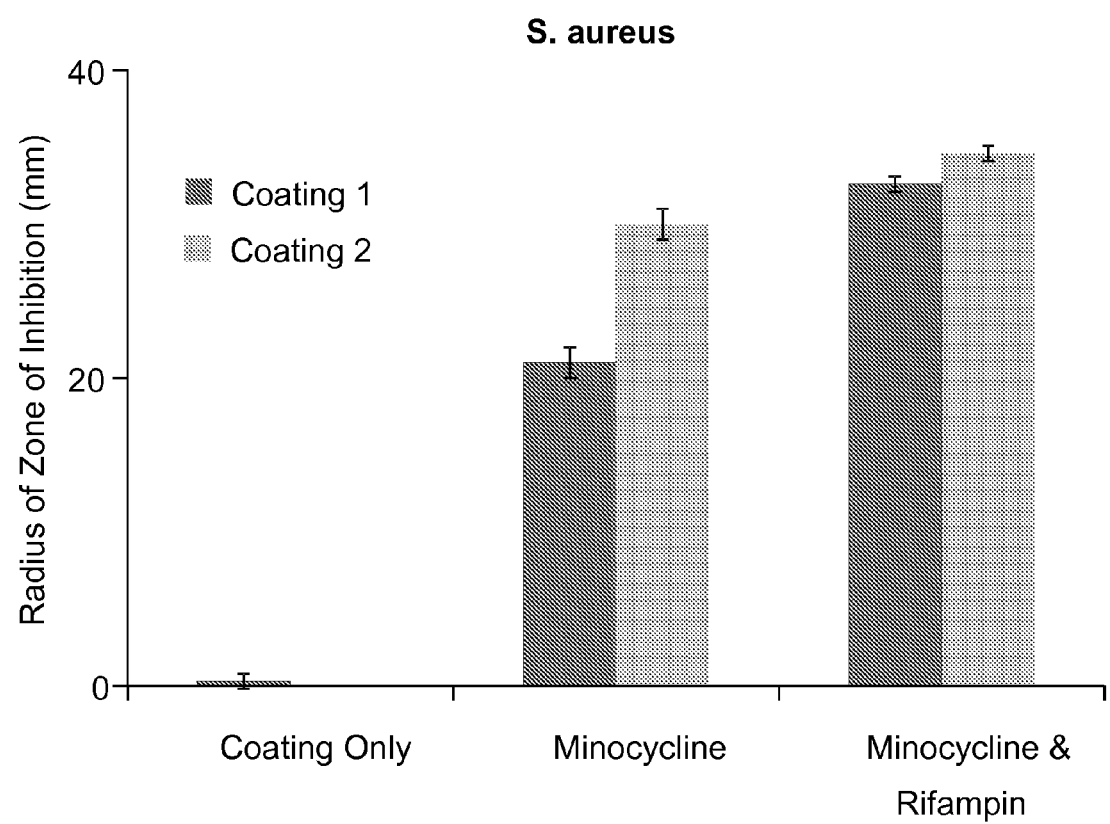
FIG. 10 depicts antimicrobial efficacy of vascular grafts coated with coating compositions of the invention against *S. aureus*.

FIG. 10 depicts results from the S. aureus zone of inhibition study. The coatings without the antibacterial drugs exhibited minimal inhibition of bacterial growth. For coatings loaded with minocycline only, the coating 2 formulation exhibited increased minocycline activity over coating 1. For coatings loaded with minocycline and rifampin, both coating 1 and 2 exhibited high bacterial growth inhibition.

Figure 11:
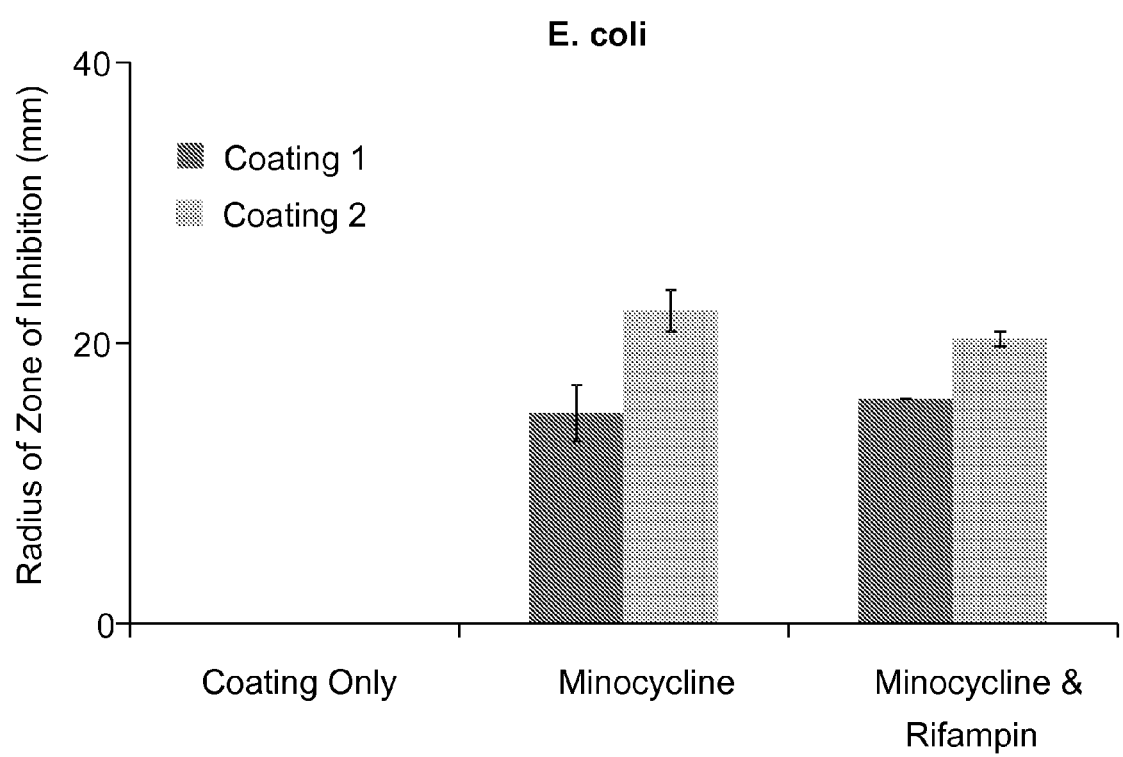
FIG. 11 depicts antimicrobial efficacy of vascular grafts coated with coating compositions of the invention against *E. coli*.

FIG. 11 depicts results from the E. coli zone of inhibition study. The coatings without the antibacterial drugs exhibited minimal inhibition of bacterial growth. For coatings loaded with minocycline only or with minocycline and rifampin, the coating 2 formulation exhibited increased minocycline activity over coating 1.

Example 8

Elution Kinetics Study

Using coating 1 from Example 7 and a rapamycin loading of 500 μg, a commercially available graft (Bard Impra 6 mm graft) was coated with as described in herein. Accelerated elution was performed in 50 ml drinks of 0.4 wt % sodium docecyl sulfate in phosphate buffered saline. At 1, 6, 12, and 24 hours drinks were retained and refreshed. Drinks were analyzed for rapamycin quantity via HPLC. Elution kinetics were compared between the coated graft and a commercially available drug eluting stent (Johnson and Johnson Cordis Cypher® stent, as described in Merciadez et al. Dissolution Technologies 2011, hereby incorporated by reference).

Figure 12:
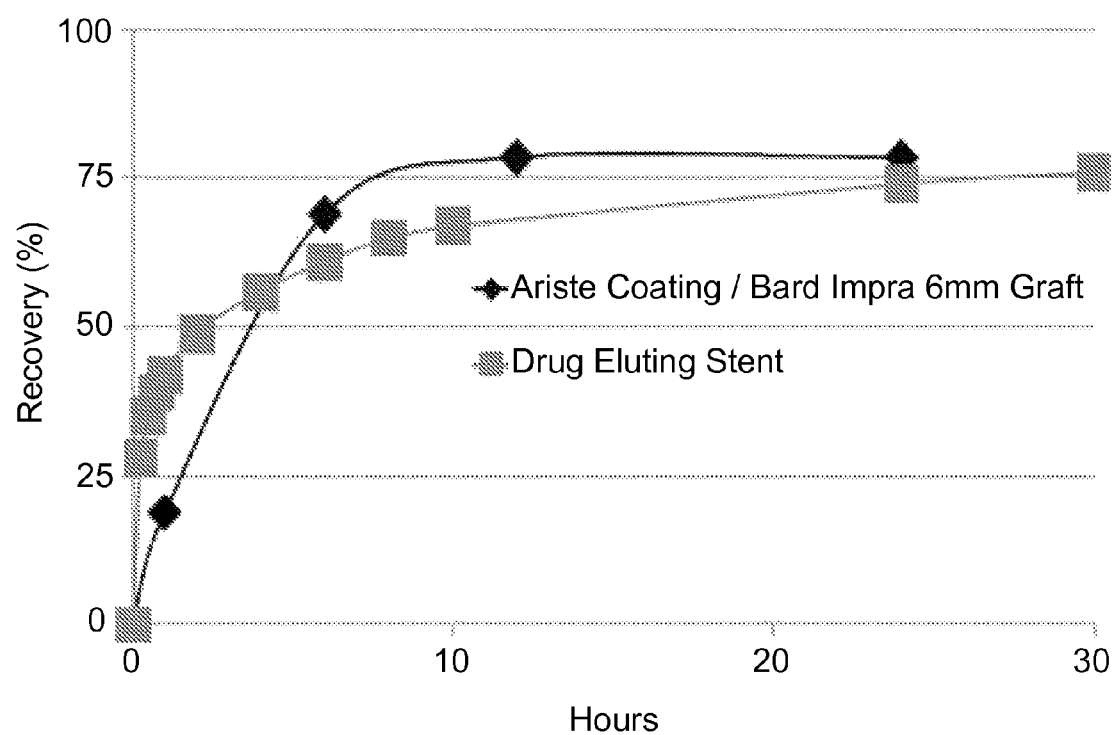
FIG. 12 depicts rapamycin elution from a commercially available drug eluting stent and a graft coated with a composition of the invention.

FIG. 12 depicts results from the elution study. The drug eluting stent exhibited a burst release of rapamycin followed by a slowed rate of elution. By contrast, the coated graft eluted rapamycin at a linear rate before hitting a plateau associated with depleted rapamycin stores. The linear elution profile is expected to result in a more efficient and efficacious delivery of rapamycin to adjacent tissue. A skilled artisan will understand that about 24 hours of an accelerated elution study as described herein corresponds to about 30 days of an in vivo, unaccelerated elution in, e.g., pigs.

Example 9

Preparation of Ariste-BDPM Coatings

Coatings on 6 mm Impra vascular grafts using a 1:1 weight ratio of Formula XII and methyl methacrylate (MMA). Both coatings use the same formulation but are applied through two different application methods and are identified as coatings G and M. Both application methods utilize a two-step coat and cure process. The composition of each application solution is shown below in Table 5.

TABLE 5

Application solutions for coatings G and M

| Solution 1 | Solution 2 |
| --- | --- |
| 4.99 wt % Formula XII | 99.80 wt % dichlorobenzene |
| 4.99 wt % MMA | 0.20 wt % Irgacure 819 |
| 89.82 wt % dichlorobenzene | (Lucirin BAPO) |
| 0.20 wt % Irgacure 819 | |
| (Lucirin BAPO) | |

Both coatings utilize similar process flow steps which are achieved with different pieces of equipment. Table 6 provides a generalized step by step procedure for producing the coating G and M on the vascular grafts.

TABLE 6

Process flow steps for coatings G and M
Workflow for Producing Coatings Sample G and Sample M

| Chronological step number | Task |
| --- | --- |
| 1 | Build graft/rod assembly and put in oven |
| 2 | Prepare Coat 1 working solution |
| 3 | Build Coat 1 curing jig |
| 4 | Retrieve graft/rod assembly from jig |
| 5 | Prepare Coat 2 solution |
| 6 | Prepare Coat 1 solution |
| 7 | Apply Coat 1 |
| 8 | Return graft/rod assembly to jig |
| 9 | Cure Coat 1 |
| 10 | Remove graft/rod assembly from jig |
| 11 | Build Coat 2 curing jig |
| 12 | Retrieve graft/rod assembly from jig |
| 13 | Apply Coat 2 |
| 14 | Remove PTFE thread seal |
| 15 | Return graft/rod assembly to jig |
| 16 | Cure Coat 2 |
| 17 | Retrieve graft/rod assembly from jig |
| 18 | Remove graft from rod |
| 19 | Dry overnight |

Specific to coating G, vascular grafts are positioned on ¼" glass rod such that 1 cm of the graft is sitting proud of the rod tip. Polytetrafluoroethylene pipe thread tape is then tightly wrapped around that portion of the graft which is in contact with the glass rod (this excludes the 1 cm portion sitting proud of tip). Using a ring stand and clamp, position graft/rod assembly such that it is facing down, creating a 20° angle with the work surface and perpendicular to the line of incident of a 405 nm CureJet energy source (Loctite). This angle assures that both the inner and outer lumen surfaces are exposed to 405 nm light. Position the center of the open terminal end of graft such that it is aligned with the center of the 405 nm CureJet's line of incident at a distance of 6" form the CureJet's lens. The rod should run perpendicular to the gun lens and face away from the gun. The jig will now have been created for utilization in the curing process. Remove graft and rod assembly from jig and warm along with second ¼" glass rod to 50° C. in a preheated convection oven. In a timely manner, remove the graft/rod assembly from oven and apply 75 µl of 50° C. Solution 1 (Table 5) to the inner lumen area of the graft. Assist solution uptake into graft wall microstructure using the second 50° C. by compressing and expanding graft multiple times, pulling Solution 1 solution into the wall microstructure; this step is performed through inserting the second rod into the terminal end of the graft. At this point one end of the graft will be affixed to the first glass rod via the pipe thread tape, and the other end will have the second glass rod positioned at the terminal end. The entire assembly may need to be inverted or held sideways to assure an even coating. The needed positioning will be apparent to the operator as solution build-up is easily visualized and can be corrected using gravity and reorientation to relocate the excess solution. The vascular graft is then expanded and compressed, forcing Solution 1 throughout the microstructure of the graft. Once all of Solution 1 has been evenly distributed throughout the microstructure of the terminal 1 cm of the graft, remove the second (non-wrapped) rod from the assembly. Carefully expand graft completely using forceps to assure porosity is open. Forceps are used by only contacting a minimal amount of the graft at the open end and pulling graft. This is act of expanding the graft should be conducted at several points along the terminal circumference. Return graft/rod assembly to ring stand set-up in the position established prior. Cure under 405 nm light for five minutes, spinning graft/rod assembly 90° every 30 seconds. Spinning is performed along the length of the graft/rod assembly and is accomplished by twisting rod between thumb and index finger. Care should be taken to maintain alignment of graft/rod assembly with light source when spinning. Remove graft/rod assembly from jig and add 75 µl of 50° C. Solution 2 (Table 5) to inner lumen. Work Solution 2 into graft microstructure using compression and extension of graft length which is performed with forceps only (as opposed to the second glass rod, unlike prior). Graft should be left in the extended position after Solution 2 solution is applied. Solution 2 will be more easily incorporated and does not require second glass rod as with Solution 1. Remove pipe thread tape and slide graft from glass rod, contacting uncoated end only (opposite side than that coated). Fix graft into forceps and clamps such that the coated end remains undisturbed. Perform five more minutes of curing under 405 nm light at 6" distance from CureJet lens and maintaining 20° angle with perpendicular line of CureJet lens. Rotate assembly 180° every 30 seconds throughout cure. 180° rotation is performed such that the front (CureJet facing) lumen opening is centered with the CureJet lens and the graft is suspended in air. Basically, the forceps/clamp assembly is flipped from one side of the light beam to the other. Allow solvent to dry and curing to complete by suspending graft in air overnight on a thin wire which minimally occludes the inner lumen area.

Specific to coating M, build graft/rod assembly with polytetrafluoroethylene pipe thread seal as described above for coating G. Using a ring stand and clamp, position the graft/rod assembly such that it is facing up at a 200 with the work surface and perpendicular line of a 375 nm CureJet lens. The CureJet will need to be elevated from the work surface. This angle assures that both the inner and outer lumen surfaces are exposed to 375 nm light. Position the center of the open terminal end of graft is aligned with the center of the 375 nm CureJet gun and at a distance of 9". The glass rod should face away from the gun and lie in a plane with the perpendicular line of the CureJet lens (line of incident). Using a second ring stand clamp, position an S10 Elipar gun (3M ESPE) such that it faces the front of the graft (CureJet facing side) at a 45° angle. The surface of the Elipar light guide is positioned ¾" from the front circumference of the graft and out of the direct path of light from the CureJet; the Elipar gun and light guide are to be located just to the side of the plane which contains the CureJets line of incident and is perpendicular with the work surface. Remove graft/rod assembly from jig and add Solution 1 at 50° C. to graft as described above for Sample G. Cure in jig using both the 375 nm CureJet and S10 Elipar gun (in continuous mode) for five minutes, rotating 90° every 30 seconds. The Elipar will need to be restarted throughout cure as it automatically turns off after two minutes in continuous mode. Remove graft/rod assembly from jig and remove pipe thread seal tape. Partially slide graft off of rod 0.3 cm by pushing uncoated portion along rod length. Add 75 µl of Solution 2 at 50° C. coat to graft lumen (now 1.3 cm length) as described above for Sample G. Return the coated graft to the jig and repeat five minute cure using a working distance of 4", both light sources (375 nm CureJet and Elipar gun). Spin assembly 90° every 30 seconds as done previously. Slide grafts completely off of rod using uncoated end and allow curing and drying to complete overnight suspended in air jon wire as described above for Sample G.

Example 10

Coated Mesh Implants

Coating formulations are prepared as described in Example 2-3 and Example 9. The coating formulations comprise an antibiotic and an analgesic. Soft tissue meshes (e.g., hernia patches) are coated as described herein. The coated hernia patches are surgically implanted into human patients suffering from a ventral hernia. Incidence of nosocomial infection is reduced in patients implanted with the coated patches as compared to patients implanted with uncoated patches. Subjective pain is evaluated in the patients by questionnaire, and is determined to be significantly reduced in patients implanted with the coated patches as compared to patients implanted with uncoated patches.

Example 11

Coated Dialysis Catheter Implants

Coating formulations are prepared as described in Example 2-3 and Example 9. The coating formulations comprise an antibiotic Dialysis catheters are coated as described herein. Human patients are catheterized with the coated dialysis catheters. Incidence of nosocomial infection is reduced in patients catheterized with the coated catheters as compared to patients catheterized with uncoated catheters.

Example 12

Neointimal Formation

In one animal study, drug eluting coatings were able to reduce neointimal formation (scar tissue) by 68%.

Example 13

Bacterial Colonization

In one animal study, drug eluting coatings were able to reduce bacterial colonization by 99.9%.

Example 14

Drug Eluting Vascular Graft

BDPM coating compositions are formulated as described herein. The coating composition comprises an anti-proliferative agent and an anti-thrombotic agent. The coating is applied to a vascular graft using a method as described herein. The coated vascular graft is implanted into a human subject in need thereof. Scar tissue formation is assessed in the patient receiving the drug-eluting graft and compared to a control patient implanted with a non-coated graft. Thrombosis is assessed in the patient receiving the drug-eluting graft and compared to a control patient implanted with a non-coated graft. Patients implanted with the coated vascular graft exhibit reduced scar tissue formation and reduced thrombosis as compared to patients implanted with corresponding non-coated grafts.

Example 15

Inhibition of Restenosis

A study is performed to deliver a restenosis-inhibiting drug at the terminal venous ends of arteriovenous grafts used for hemodialysis. Manufacturing consistency is improved through the use of the invention coatings. The invention coatings improve coating uniformity and drug loading consistency, and reduce variation in drug elution profiles. Coating integrity and minimal effects on the graft base-material's open three-dimensional network microstructure is confirmed qualitatively using scanning electron microscopy. Three embodiments of the device are developed using the three coating formulations prepared as described herein; each version produces a distinct drug elution profile characteristic and allows for an FDA-required dosing study during later Phase II work. Drug elution profiles and the presence of coating-derived leachables (unreacted monomers) are studied. Curing conditions are optimized to minimize excess leaching of monomer. Using the intermediate elution profile design variant, a preclinical feasibility study is conducted in an arteriovenous pig model, where the carotid artery is brought into communication with the ipsilateral jugular vein to create a venous anastomosis. Pigs are implanted with either uncoated control or drug-coated experimental grafts. At twenty-one days post-implantation, the grafts are harvested. The venous anastomoses are subjected to histomorphometrical evaluation to determine the effect of drug-loaded grafts on the prevalence of associated restenosis. A greater than 20% reduction of restenosis is evident in pigs implanted with the coated experimental grafts as compared to pigs implanted with the control grafts.

Example 16

Application of Coatings to Discrete Portions of a Product

Compositions of the invention will be applied to discrete portions of devices to be coated. In one particular example a coating will be applied at a point where the device is trimmed. In one embodiment a coating will be applied distal to a trimmable portion of the device. This can allow a physician to size the implant to fit the targeted surgical area without losing the drug by trimming.

Example 17

Degradation of Drugs by PTPO Photoinitiator in Some Coatings

Figure 13:
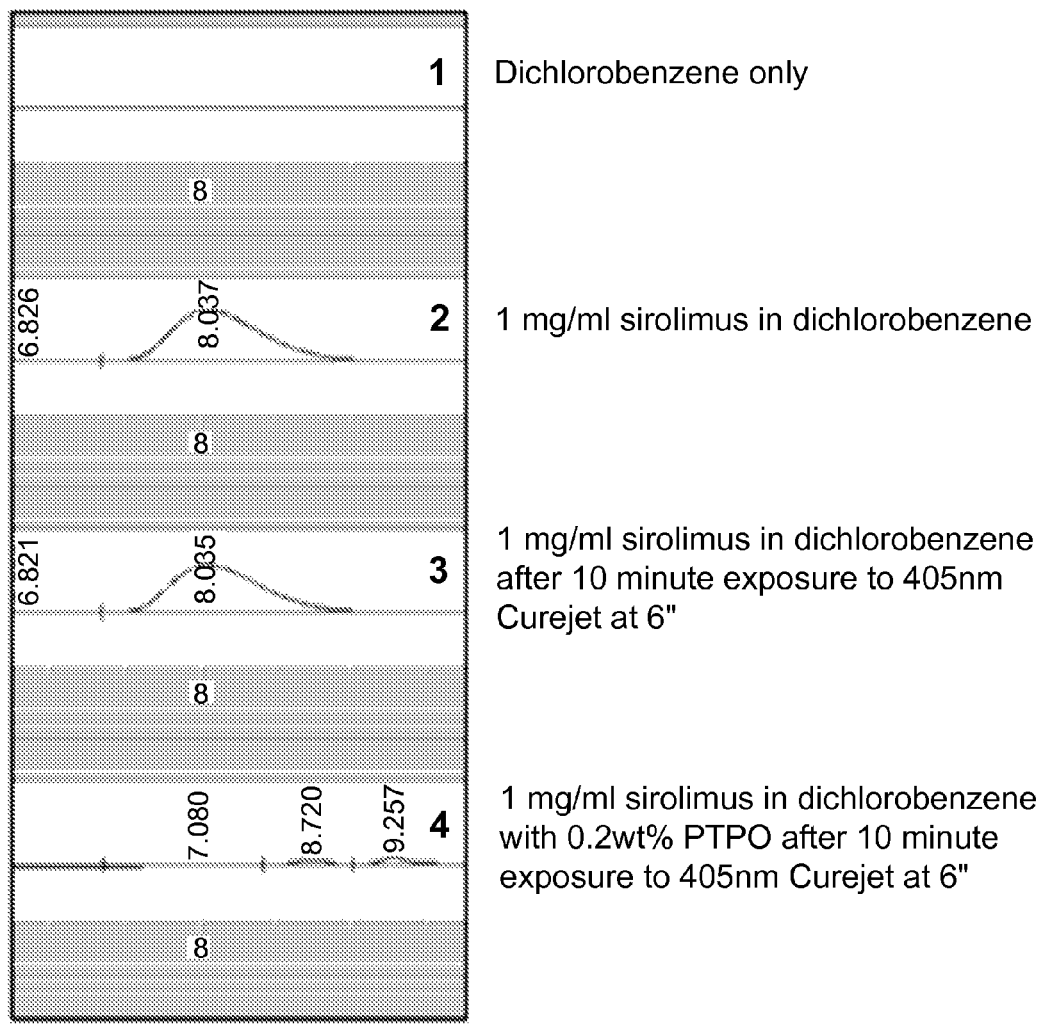
FIG. 13 depicts results from an HPLC experiment testing the effects of a photoinitiator on light-induced drug degradation.

Sirolimus eluting graft samples were coated with a composition comprising 5% BDPM (Formula XII), 5% methyl methacrylate, and 0.2% PTPO in dichlorobenzene. Samples of the composition comprising 500 µg sirolimus were analyzed by HPLC. The elution samples demonstrated low recovery of sirolimus (<10%, typically 3%). To determine the contribution of the PTPO photoinitiator to the sirolimus recovery, 1 mg/ml sirolimus solutions in dichlorobenzene only, in dichlorobenzene comprising 0.2% wt/wt PTPO were tested by HPLC. FIG. 13 depicts chromatograms from the study. Note the absence of the sirolimus peak in chromatogram #4.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A polymerized coating, comprising:
   (a) a polymer of an aromatic dimethacrylate of structural Formula (II):

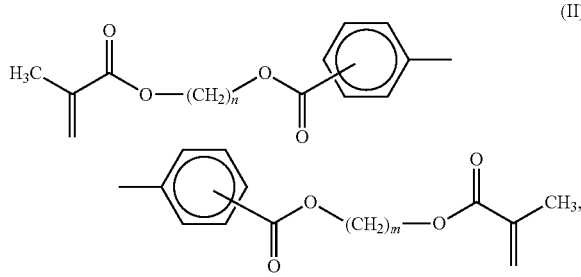
(II)

wherein:
   each n is independently 1-10; and
   each m is independently 1-10; and
   (b) a therapeutic agent.

2. The polymerized coating of claim 1, wherein the aromatic dimethacrylate has the following structural formula:

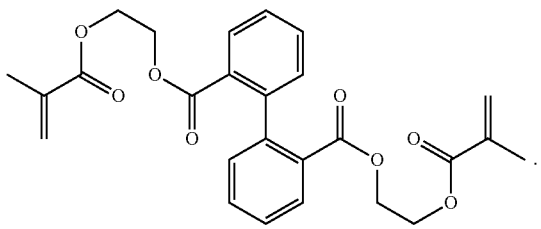

3. The polymerized coating of claim 1, further comprising an odorant.

4. The polymerized coating of claim 1, wherein the polymer further comprises an additional methacrylate.

5. The polymerized coating of claim 1, wherein the aromatic dimethacrylate and the additional methacrylate are present in a ratio that is between 1:10 and 10:1.

6. The polymerized coating of claim 4, wherein the aromatic dimethacrylate and the additional methacrylate are present in a ratio that is between 1:5 and 5:1.

7. The polymerized coating of claim 4, wherein the aromatic dimethacrylate and the additional methacrylate are present in a ratio that is between 1:2 and 2:1.

8. The polymerized coating of claim 4, wherein the aromatic dimethacrylate and the additional methacrylate are present in a 1:1 ratio.

9. The polymerized coating of claim 4, wherein the additional methacrylate is a methyl methacrylate.

10. The polymerized coating of claim 4, wherein the additional methacrylate is of the following structure:

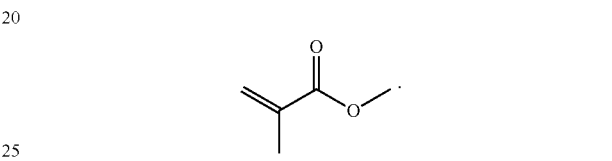

11. The polymerized coating of claim 1, wherein the therapeutic agent is selected from the group consisting of antiplatelets, antithrombins, cytostatic agents, antiproliferative agents, vasodilators, alkylating agents, antimicrobials, antibiotics, antimitotics, anti-infective agents, antisecretory agents, anti-inflammatory agents, immunosuppressive agents, antimetabolite agents, growth factor antagonists, free radical scavengers, antioxidants, radiotherapeutic agents, anesthetic agents, radiopaque agents, radiolabeled agents, nucleotides, proteins, glycoproteins, hormones, odor-emitting agents, anti-stenosis agents, enzymes, monoclonal antibodies, ribonucleases and any combinations thereof.

12. The polymerized coating of claim 1, comprising one or more additional therapeutic agents.

* * * * *

UNITED STATES PATENT AND TRADEMARK OFFICE
CERTIFICATE OF CORRECTION

| | | |
|---|---|---|
| PATENT NO. | : 9,605,175 B2 | Page 1 of 1 |
| APPLICATION NO. | : 14/439650 | |
| DATED | : March 28, 2017 | |
| INVENTOR(S) | : Lisa Jennings et al. | |

It is certified that error appears in the above-identified patent and that said Letters Patent is hereby corrected as shown below:

In the Claims

In Column 74 Line 3 please replace "claim 1" with --Claim 4--.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*